(12) United States Patent
Løset

(10) Patent No.: US 8,735,330 B2
(45) Date of Patent: May 27, 2014

(54) PVII PHAGE DISPLAY

(75) Inventor: Geir Åge Løset, Oslo (NO)

(73) Assignee: Nextera AS, Oslo (NO)

( * ) Notice: Subject to any disclaimer, the term of this patent is extended or adjusted under 35 U.S.C. 154(b) by 743 days.

(21) Appl. No.: 12/673,649

(22) PCT Filed: Aug. 20, 2008

(86) PCT No.: PCT/EP2008/060908
§ 371 (c)(1),
(2), (4) Date: Oct. 12, 2010

(87) PCT Pub. No.: WO2009/024591
PCT Pub. Date: Feb. 26, 2009

(65) Prior Publication Data
US 2011/0251106 A1    Oct. 13, 2011

Related U.S. Application Data

(60) Provisional application No. 60/956,871, filed on Aug. 20, 2007.

(30) Foreign Application Priority Data

Nov. 26, 2007  (DK) .................................. 2007 01673

(51) Int. Cl.
*C40B 40/08*    (2006.01)
(52) U.S. Cl.
USPC .......................................................... 506/17
(58) Field of Classification Search
None
See application file for complete search history.

(56) References Cited

U.S. PATENT DOCUMENTS

| | | |
|---|---|---|
| 7,037,706 B1 | 5/2006 | Barrett et al. |
| 2006/0068421 A1 | 3/2006 | Gray |
| 2011/0301064 A1 | 12/2011 | Løset |

FOREIGN PATENT DOCUMENTS

| | | |
|---|---|---|
| WO | WO 00/71694 A1 | 11/2000 |
| WO | WO 2004/050871 A1 | 6/2004 |
| WO | WO 2006/068421 A1 | 6/2006 |
| WO | WO 2009/024591 A1 | 2/2009 |
| WO | WO 2009/085462 A1 | 7/2009 |

OTHER PUBLICATIONS

Andris-Widhopf et al. (Aug. 2000) Journal of Immunological Methods vol. 242 pp. 159 to 18.*
Simons et al. (Jul. 1, 1981) Proceedings of the National Academy of Sciences USA vol. 78 pp. 4194 to 4198.*
Barbas et al. (Sep. 15, 1991) Proceedings of the National Academy of Sciences USA vol. 88 pp. 7978 to 7982.*
Gao, Changshou et al., "Making artificial antibodies: A format for phage display of combinational heterodimeric arrays" Proc. Natl. Acad. Sci. May 1999, pp. 6025-6030, vol. 96.

(Continued)

*Primary Examiner* — Heather Calamita
*Assistant Examiner* — Christian Boesen
(74) *Attorney, Agent, or Firm* — Knobbe Martens Olson & Bear LLP

(57) ABSTRACT

The present invention provides an alternative scaffold for peptides displayed on filamentous phages through novel fusion proteins primarily originating from pVII. Libraries of filamentous phages can be created from fusion proteins, and a phage display system comprising a phagemid and a helper phage is a part of the invention. An aspect of the invention is a kit containing a phage display system comprising a phagemid and a helper phage that contains a nucleic acid encoding the fusion protein of the invention.

12 Claims, 22 Drawing Sheets

(56) References Cited

OTHER PUBLICATIONS

Kawasnikowski, Piotr et al., "Multivalent display system on filamentous bacteriophage pVII minor coat protein" Journal of Immunological Methods, 2005, pp. 135-143, vol. 307.

Endemann, Heike et al., "Location of Filamentous Phage Minor Coat Proteins in Phage and in Infected Cells" J. Mol. Biol., 1995, pp. 496-506, vol. 250.

Gao, Changshou et al., "A method for the generation of combinatorial antibody libraries using pIX phage display" PNAS, Oct. 1, 2002, pp. 12612-12616, vol. 99, No. 20.

* cited by examiner

SEQUENCE LISTING

```
<160> NUMBER OF SEQ ID NOS: 40

<210> SEQ ID NO 1
<211> LENGTH: 33
<212> TYPE: PRT
<213> ORGANISM: Bacteriophage M13
```

<400> SEQUENCE: 1

Met Glu Gln Val Ala Asp Phe Asp Thr Ile Tyr Gln Ala Met Ile Gln
1               5                   10                  15

Ile Ser Val Val Leu Cys Phe Ala Leu Gly Ile Ile Ala Gly Gly Gln
                20                  25                  30

Arg

<210> SEQ ID NO 2
<211> LENGTH: 424
<212> TYPE: PRT
<213> ORGANISM: Bacteriophage fd

<400> SEQUENCE: 2

Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
                20                  25                  30

Asn Ser Phe Thr Asn Val Trp Lys Asp Asp Lys Thr Leu Asp Arg Tyr
            35                  40                  45

Ala Asn Tyr Glu Gly Cys Leu Trp Asn Ala Thr Gly Val Val Val Cys
    50                  55                  60

Thr Gly Asp Glu Thr Gln Cys Tyr Gly Thr Trp Val Pro Ile Gly Leu
65                  70                  75                  80

Ala Ile Pro Glu Asn Glu Gly Gly Gly Ser Glu Gly Gly Gly Ser Glu
                85                  90                  95

Gly Gly Gly Ser Glu Gly Gly Gly Thr Lys Pro Pro Glu Tyr Gly Asp
            100                 105                 110

Thr Pro Ile Pro Gly Tyr Thr Tyr Ile Asn Pro Leu Asp Gly Thr Tyr
        115                 120                 125

Pro Pro Gly Thr Glu Gln Asn Pro Ala Asn Pro Asn Pro Ser Leu Glu
    130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Pro Val Asn Ala Gly Gly Gly Ser Gly
225                 230                 235                 240

Gly Gly Ser Gly Gly Gly Ser Glu Gly Gly Ser Glu Gly Gly Gly
                245                 250                 255

Ser Glu Gly Gly Gly Ser Glu Gly Gly Gly Ser Gly Gly Ser Gly
            260                 265                 270

Ser Gly Asp Phe Asp Tyr Glu Lys Met Ala Asn Ala Asn Lys Gly Ala
        275                 280                 285

Met Thr Glu Asn Ala Asp Glu Asn Ala Leu Gln Ser Asp Ala Lys Gly
    290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
                325                 330                 335

```
Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
            355                 360                 365

Ser Val Glu Cys Arg Pro Tyr Val Phe Gly Ala Gly Lys Pro Tyr Glu
        370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
            420

<210> SEQ ID NO 3
<211> LENGTH: 73
<212> TYPE: PRT
<213> ORGANISM: Bacteriophage M13

<400> SEQUENCE: 3

Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asp Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70

<210> SEQ ID NO 4
<211> LENGTH: 17
<212> TYPE: PRT
<213> ORGANISM: Artificial
<220> FEATURE:
<223> OTHER INFORMATION: synthetic peptide

<400> SEQUENCE: 4

Met Ser Gly Leu Asn Asp Ile Phe Glu Ala Gln Lys Ile Glu Trp His
1               5                   10                  15

Glu

<210> SEQ ID NO 5
<211> LENGTH: 76
<212> TYPE: DNA
<213> ORGANISM: Artificial
<220> FEATURE:
<223> OTHER INFORMATION: oligonucleotide

<400> SEQUENCE: 5
ccggctaagt aacatgtccg gcctgaacga tatctttgaa gcgcagaaaa ttgaatggca     60
tgaaatggag caggtc                                                    76

<210> SEQ ID NO 6
<211> LENGTH: 76
<212> TYPE: DNA
<213> ORGANISM: Artificial
<220> FEATURE:
<223> OTHER INFORMATION: oligonucleotide
```

```
<400> SEQUENCE: 6
gacctgctcc atttcatgcc attcaatttt ctgcgcttca agatatcgt tcaggccgga    60 catgttactt agccgg                                                   76

<210> SEQ ID NO 7
<211> LENGTH: 53
<212> TYPE: DNA
<213> ORGANISM: Artificial
<220> FEATURE:
<223> OTHER INFORMATION: oligonucleotide

<400> SEQUENCE: 7
ccggctaagt aacatggact acaaagatga cgatgacaaa atggagcagg tcg          53

<210> SEQ ID NO 8
<211> LENGTH: 53
<212> TYPE: DNA
<213> ORGANISM: Artificial
<220> FEATURE:
<223> OTHER INFORMATION: oligonucleotide

<400> SEQUENCE: 8
cgacctgctc cattttgtca tcgtcatctt tgtagtccat gttacttagc cgg          53

<210> SEQ ID NO 9
<211> LENGTH: 9
<212> TYPE: PRT
<213> ORGANISM: Artificial
<220> FEATURE:
<223> OTHER INFORMATION: synthetic peptide

<400> SEQUENCE: 9

Met Asp Tyr Lys Asp Asp Asp Asp Lys
1               5

<210> SEQ ID NO 10
<211> LENGTH: 47
<212> TYPE: DNA
<213> ORGANISM: Artificial
<220> FEATURE:
<223> OTHER INFORMATION: oligonucleotide

<400> SEQUENCE: 10
ccggctaagt aacatgcatc accatcacca tcacatggag caggtcg                 47

<210> SEQ ID NO 11
<211> LENGTH: 47
<212> TYPE: DNA
<213> ORGANISM: Artificial
<220> FEATURE:
<223> OTHER INFORMATION: oligonucleotide

<400> SEQUENCE: 11
cgacctgctc catgtgatgg tgatggtgat gcatgttact tagccgg                 47

<210> SEQ ID NO 12
<211> LENGTH: 7
<212> TYPE: PRT
<213> ORGANISM: Artificial
<220> FEATURE:
<223> OTHER INFORMATION: synthetic peptide

<400> SEQUENCE: 12

Met His His His His His His
1               5
```

<210> SEQ ID NO 13
<211> LENGTH: 39
<212> TYPE: DNA
<213> ORGANISM: Artificial
<220> FEATURE:
<223> OTHER INFORMATION: oligonucleotide

<400> SEQUENCE: 13
agaggagaaa ttaaccatgg aatacctatt gcctacggc                    39

<210> SEQ ID NO 14
<211> LENGTH: 39
<212> TYPE: DNA
<213> ORGANISM: Artificial
<220> FEATURE:
<223> OTHER INFORMATION: oligonucleotide

<400> SEQUENCE: 14
gccgtaggca ataggtattc catggttaat ttctcctct                    39

<210> SEQ ID NO 15
<211> LENGTH: 21
<212> TYPE: DNA
<213> ORGANISM: Artificial
<220> FEATURE:
<223> OTHER INFORMATION: oligonucleotide

<400> SEQUENCE: 15
tagctcactc attaggcacc c                                       21

<210> SEQ ID NO 16
<211> LENGTH: 18
<212> TYPE: DNA
<213> ORGANISM: Artificial
<220> FEATURE:
<223> OTHER INFORMATION: oligonucleotide

<400> SEQUENCE: 16
tttggatcca gcggccgc                                           18

<210> SEQ ID NO 17
<211> LENGTH: 35
<212> TYPE: DNA
<213> ORGANISM: Artificial
<220> FEATURE:
<223> OTHER INFORMATION: oligonucleotide

<400> SEQUENCE: 17
atatgatatc agaatggagc aggtcgcgga tttcg                        35

<210> SEQ ID NO 18
<211> LENGTH: 40
<212> TYPE: DNA
<213> ORGANISM: Artificial
<220> FEATURE:
<223> OTHER INFORMATION: oligonucleotide

<400> SEQUENCE: 18
atatgctagc ttatcatctt tgaccccag cgattatacc                    40

<210> SEQ ID NO 19
<211> LENGTH: 46
<212> TYPE: DNA
<213> ORGANISM: Artificial
<220> FEATURE:
<223> OTHER INFORMATION: oliognucleotide

```
<400> SEQUENCE: 19
atctcttcca tggagcaggt cgcggatttc gacacaattt atcagg          46

<210> SEQ ID NO 20
<211> LENGTH: 38
<212> TYPE: DNA
<213> ORGANISM: Artificial
<220> FEATURE:
<223> OTHER INFORMATION: oligonucleotide

<400> SEQUENCE: 20
atctcttcca tgttacttag ccggaacgag gcgcagac                   38

<210> SEQ ID NO 21
<211> LENGTH: 43
<212> TYPE: DNA
<213> ORGANISM: Artificial
<220> FEATURE:
<223> OTHER INFORMATION: oligonucleotide

<400> SEQUENCE: 21
atctcttcac atgaaatacc tattgcctac ggcagccgct ggc             43

<210> SEQ ID NO 22
<211> LENGTH: 33
<212> TYPE: DNA
<213> ORGANISM: Artificial
<220> FEATURE:
<223> OTHER INFORMATION: oligonucleotide

<400> SEQUENCE: 22
tctcttcaca tggcccaggt gcagctggtg cag                        33

<210> SEQ ID NO 23
<211> LENGTH: 41
<212> TYPE: DNA
<213> ORGANISM: Artificial
<220> FEATURE:
<223> OTHER INFORMATION: oligonucleotide

<400> SEQUENCE: 23
atctcttccc attctgatat ctttggatcc agcggccgca c               41

<210> SEQ ID NO 24
<211> LENGTH: 24
<212> TYPE: DNA
<213> ORGANISM: Artificial
<220> FEATURE:
<223> OTHER INFORMATION: oligonucleotide

<400> SEQUENCE: 24
agcagctttg ttacgttgat ttgg                                  24

<210> SEQ ID NO 25
<211> LENGTH: 19
<212> TYPE: DNA
<213> ORGANISM: Artificial
<220> FEATURE:
<223> OTHER INFORMATION: oligonucleotide

<400> SEQUENCE: 25
gcagcgaaag acagcatcg                                        19
```

```
<210> SEQ ID NO 26
<211> LENGTH: 253
<212> TYPE: PRT
<213> ORGANISM: Artificial
<220> FEATURE:
<223> OTHER INFORMATION: scFv antibody

<400> SEQUENCE: 26
```

Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Ile Thr Trp Val Arg Gln Ala Pro Gly Gln Gly Leu Glu Trp Met
            35                  40                  45

Gly Trp Ile Ser Ala Tyr Asn Gly Tyr Lys Ser Tyr Ala Gln Asn Phe
 50                  55                  60

Gln Gly Arg Val Thr Met Thr Thr Asp Thr Phe Thr Ser Thr Ala Tyr
65                  70                  75                  80

Met Glu Leu Arg Thr Leu Arg Ser Asp Asp Thr Ala Val Tyr Tyr Cys
                85                  90                  95

Val Arg Leu Val Pro Lys Arg Thr Ala Thr Leu His Tyr Tyr Ile Asp
            100                 105                 110

Val Trp Gly Lys Gly Thr Thr Val Thr Val Ser Ser Gly Ser Ala Ser
        115                 120                 125

Ala Pro Lys Leu Glu Glu Gly Glu Phe Ser Glu Ala Arg Val Gln Ser
    130                 135                 140

Val Leu Thr Gln Pro Pro Ser Val Ser Ala Ala Pro Gly Gln Lys Val
145                 150                 155                 160

Thr Ile Ser Cys Ser Gly Ser Ser Ser Asn Ile Gly Asn Asn Tyr Val
                165                 170                 175

Ser Trp Tyr Val Gln Leu Pro Gly Thr Ala Pro Lys Leu Leu Ile Tyr
            180                 185                 190

Asp Asn Asn Lys Arg Phe Ser Gly Val Pro Asp Arg Phe Ser Gly Ser
        195                 200                 205

Lys Ser Gly Thr Ser Ala Thr Leu Gly Ile Thr Gly Leu Gln Thr Gly
    210                 215                 220

Asp Glu Ala Asp Tyr Tyr Cys Gly Ala Trp Asp Gly Ser Leu Arg Glu
225                 230                 235                 240

Ala Val Phe Gly Gly Gly Thr Lys Val Thr Val Leu Gly
                245                 250

```
<210> SEQ ID NO 27
<211> LENGTH: 249
<212> TYPE: PRT
<213> ORGANISM: Artificial
<220> FEATURE:
<223> OTHER INFORMATION: scFv antibody

<400> SEQUENCE: 27
```

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Arg Gly Leu Glu Trp Ile
            35                  40                  45

Gly Arg Ile Asp Pro Asn Ser Gly Gly Thr Lys Tyr Asn Glu Lys Phe
 50                  55                  60

```
Lys Ser Lys Ala Thr Leu Thr Val Asp Lys Pro Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Asp Tyr Tyr Gly Ser Ser Tyr Phe Asp Tyr Trp Gly Gln
            100                 105                 110

Gly Thr Thr Leu Thr Val Ser Ser Leu Glu Gly Gly Gly Ser Gly
        115                 120                 125

Gly Gly Gly Ser Gly Gly Gly Ser Glu Leu Gln Ala Val Val Thr
    130                 135                 140

Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
            180                 185                 190

Asn Asn Arg Ala Pro Gly Val Pro Ala Arg Phe Ser Gly Ser Leu Ile
            195                 200                 205

Gly Asp Lys Ala Ala Leu Thr Ile Thr Gly Thr Gln Thr Glu Asp Glu
        210                 215                 220

Ala Met Tyr Phe Cys Ala Leu Trp Tyr Ser Asn His Trp Val Phe Gly
225                 230                 235                 240

Gly Gly Thr Lys Leu Thr Val Leu Gly
                245

<210> SEQ ID NO 28
<211> LENGTH: 248
<212> TYPE: PRT
<213> ORGANISM: Artificial
<220> FEATURE:
<223> OTHER INFORMATION: scTCR antibody

<400> SEQUENCE: 28

Gln Gln Lys Val Gln Gln Ser Pro Glu Ser Leu Ile Val Pro Glu Gly
 1               5                  10                  15

Ala Met Thr Ser Leu Asn Cys Thr Phe Ser Asp Ser Ala Ser Gln Tyr
                20                  25                  30

Phe Ala Trp Tyr Arg Gln Gln Ser Gly Lys Ala Pro Lys Ala Leu Met
            35                  40                  45

Ser Ile Phe Ser Asn Gly Glu Lys Glu Glu Gly Arg Phe Thr Ile His
        50                  55                  60

Leu Asn Lys Ala Ser Leu His Phe Ser Leu His Ile Arg Asp Ser Gln
 65                  70                  75                  80

Pro Ser Asp Ser Ala Leu Tyr Leu Cys Ala Val Arg Gly Pro Asn Thr
                 85                  90                  95

Gly Asn Tyr Lys Tyr Val Phe Gly Ala Gly Thr Arg Leu Lys Val Ile
            100                 105                 110

Ala Lys Leu Ser Gly Ser Ala Ser Ala Pro Lys Leu Glu Glu Gly Glu
        115                 120                 125

Phe Ser Glu Ala Arg Val Glu Ala Ala Val Thr Gln Ser Pro Arg Asn
    130                 135                 140

Lys Val Ala Val Thr Gly Gly Lys Val Thr Leu Ser Cys Asn Gln Thr
145                 150                 155                 160

Asn Asn His Asn Asn Met Tyr Trp Tyr Arg Gln Asp Thr Gly His Gly
                165                 170                 175
```

```
Leu Arg Leu Ile His Tyr Ser Tyr Gly Ala Gly Ser Thr Glu Lys Gly
            180                 185                 190

Asp Ile Pro Asp Gly Tyr Lys Ala Ser Arg Pro Ser Gln Glu Asn Phe
        195                 200                 205

Ser Leu Ile Leu Glu Leu Ala Thr Pro Ser Gln Thr Ser Val Tyr Phe
    210                 215                 220

Cys Ala Ser Gly Asp Ala Gly Gln Gly His Ser Asp Tyr Thr Phe Gly
225                 230                 235                 240

Ser Gly Thr Arg Leu Leu Val Ile
                245

<210> SEQ ID NO 29
<211> LENGTH: 4864
<212> TYPE: DNA
<213> ORGANISM: Artificial
<220> FEATURE:
<223> OTHER INFORMATION: vector pSEX81-215

<400> SEQUENCE: 29
tggcgtaata gcgaagaggc ccgcaccgat cgcccttccc aacagttgcg cagcctgaat      60
ggcgaatggg acgcgccctg tagcggcgca ttaagcgcgg cgggtgtggt ggttacgcgc     120
agcgtgaccg ctacacttgc cagcgcccta gcgcccgctc ctttcgcttt cttcccttcc     180
tttctcgcca cgttcgccgg ctttccccgt caagctctaa atcggggget ccctttaggg     240 ttccgattta gtgctttacg gcacctcgac cccaaaaaac ttgattaggg tgatggttca     300
cgtagtgggc catcgccctg atagacggtt tttcgccctt tgacgttgga gtccacgttc     360
tttaatagtg actcttgttc caaactggaa caacactcaa ccctatctcg gtctattct      420 tttgatttat aagggatttt gccgatttcg gcctattggt taaaaaatga gctgatttaa     480
caaaaattta acgcgaattt taacaaaata ttaacgctta caatttaggt ggcacttttc     540
ggggaaatgt gcgcggaacc cctatttgtt tatttttcta aatacattca aatatgtatc     600
cgctcatgag acaataaccc tgataaatgc ttcaataata ttgaaaaagg aagagtatga     660
gtattcaaca tttccgtgtc gcccttattc ccttttttgc ggcattttgc cttcctgttt     720
ttgctcaccc agaaacgctg gtgaaagtaa aagatgctga agatcagttg ggtgcacgag     780
tgggttacat cgaactggat ctcaacagcg gtaagatcct tgagagtttt cgccccgaag     840
aacgttttcc aatgatgagc acttttaaag ttctgctatg tggcgcggta ttatcccgta     900
ttgacgccgg gcaagagcaa ctcggtcgcc gcatacacta ttctcagaat gacttggttg     960
agtactcacc agtcacagaa aagcatctta cggatggcat gacagtaaga gaattatgca    1020
gtgctgccat aaccatgagt gataacactg cggccaactt acttctgaca acgatcggag    1080
gaccgaagga gctaaccgct tttttgcaca acatggggga tcatgtaact cgccttgatc    1140
gttgggaacc ggagctgaat gaagccatac caaacgacga gcgtgacacc acgatgcctg    1200
tagcaatggc aacaacgttg cgcaaactat taactggcga actacttact ctagcttccc    1260
ggcaacaatt aatagactgg atggaggcgg ataaagttgc aggaccactt ctgcgctcgg    1320
cccttccggc tggctggttt attgctgata aatctggagc cggtgagcgt gggtctcgcg    1380
gtatcattgc agcactgggg ccagatggta agccctcccg tatcgtagtt atctacacga    1440
cggggagtca ggcaactatg gatgaacgaa atagacagat cgctgagata ggtgcctcac    1500
tgattaagca ttggtaactg tcagaccaag tttactcata tatactttag attgatttaa    1560
aacttcattt ttaattttaaa aggatctagg tgaagatcct ttttgataat ctcatgacca    1620
aaatccctta acgtgagttt tcgttccact gagcgtcaga ccccgtagaa aagatcaaag    1680
```

```
gatcttcttg agatcctttt tttctgcgcg taatctgctg cttgcaaaca aaaaaaccac   1740
cgctaccagc ggtggtttgt ttgccggatc aagagctacc aactctttt ccgaaggtaa   1800
ctggcttcag cagagcgcag ataccaaata ctgtccttct agtgtagccg tagttaggcc   1860
accacttcaa gaactctgta gcaccgccta catacctcgc tctgctaatc ctgttaccag   1920
tggctgctgc cagtggcgat aagtcgtgtc ttaccgggtt ggactcaaga cgatagttac   1980
cggataaggc gcagcggtcg ggctgaacgg ggggttcgtg cacacagccc agcttggagc   2040
gaacgaccta caccgaactg agataccta gcgtgagct atgagaaagc gccacgcttc      2100
ccgaagggag aaaggcggac aggtatccgg taagcggcag ggtcggaaca ggagagcgca    2160
cgagggagct tccagggga aacgcctggt atctttatag tcctgtcggg tttcgccacc     2220
tctgacttga gcgtcgattt ttgtgatgct cgtcagggg gcggagccta tggaaaaacg     2280
ccagcaacgc ggcctttta cggttcctgg ccttttgctg ccttttgct cacatgttct      2340
ttcctgcgtt atcccctgat tctgtggata accgtattac cgccttgag tgagctgata     2400
ccgctcgccg cagccgaacg accgagcgca gcgagtcagt gagcgaggaa gcggaagagc    2460
gcccaatacg caaaccgcct ctccccgcgc gttggccgat tcattaatgc aggtatcacg    2520
aggccctttc gtcttcacct cgagagcggg cagtgagcgc aacgcaatta atgtgagtta    2580
gctcactcat taggcacccc aggctttaca ctttatgctt ccggctcgta tgttgtgtgg    2640
aattgtgagc ggataacaat ttcacacaga attcattaaa gaggagaaat taaccatgaa    2700
atacctattg cctacggcag ccgctggctt gctgctgctg gcagctcagc cggccatggc    2760
gcaagttcag ctgcagcagt ctggggctga actggtgagg cctggggtct cagtgaagat    2820
ttcctgcaag ggttctggct acaaattcac tgattatgct acgcactggg tgaaacagag    2880
tcatgcaaag agtctagagt ggattggagt tattagtact tactatggtg atactactta    2940
taaccagaag ttcaagggca aggccacaat gactgtcgac aaatcctcca gcacagccta    3000
tatggaactt cccagactga catctgatga ttctgccatc tattattgtg ccctgttacg    3060
ccccttgct tactggggcc aagggaccac ggtcaccgta tcctcaggga gtgcatccgc     3120
cccaaagctt gaagaaggtg aatttcaga agcacgcgta gatatcgtgc tgacccaatc     3180
tccactctcc ctgagtgtgt cagcaggaga aaggtcact atgagctgca agtccagtca     3240
gagtctgtta aacagtggaa atcaaaataa cgacttggcc tggtaccagc agaaaccagg    3300
gcaacgtcct aaactgttga tctacggggc atccactagg gaatctgggg tccctgatcg    3360
cttcacaggc agtggatctg gaaccgattt cactcttacc atcagcagtg tgcaggctga    3420
agacctggca gtttattact gtcagaatga tcatagttat ccgttaacgt tcggtgctgg    3480
caccaagctg gaaatcaaac gggcggccgc tggatccaaa gatatcagag ctgaaactgt    3540
tgaaagttgt ttagcaaaat cccatacaga aaattcattt actaacgtct ggaaagacga    3600
caaaacttta gatcgttacg ctaactatga gggctgtctg tggaatgcta caggcgttgt    3660
agtttgtact ggtgacgaaa ctcagtgtta cggtacatgg gttcctattg ggcttgctat    3720
ccctgaaaat gagggtggtg gctctgaggg tggcggttct gagggtggcg gttctgaggg    3780
tggcggtact aaacctcctg agtacggtga tacacctatt ccgggctata cttatatcaa    3840
ccctctcgac ggcacttatc gcctggtac tgagcaaaac cccgctaatc ctaatccttc     3900
tcttgaggag tctcagcctc ttaatacttt catgtttcag aataataggt tccgaaatag    3960
gcaggggca ttaactgttt atacgggcac tgttactcaa ggcactgacc ccgttaaaac     4020
ttattaccag tacactcctg tatcatcaaa agccatgtat gacgcttact ggaacggtaa    4080
```

-continued

```
attcagagac tgcgctttcc attctggctt taatgaggat ttatttgttt gtgaatatca    4140
aggccaatcg tctgacctgc ctcaacctcc tgtcaatgct ggcggcggct ctggtggtgg    4200
ttctggtggc ggctctgagg gtggtggctc tgagggtggc ggttctgagg gtggcggctc    4260
tgagggaggc ggttccggtg gtggctctgg ttccggtgat tttgattatg aaaagatggc    4320
aaacgctaat aagggggcta tgaccgaaaa tgccgatgaa aacgcgctac agtctgacgc    4380
taaaggcaaa cttgattctg tcgctactga ttacggtgct gctatcgatg gtttcattgg    4440
tgacgtttcc ggccttgcta atggtaatgg tgctactggt gattttgctg gctctaattc    4500
ccaaatggct caagtcggtg acggtgataa ttcacccttta atgaataatt tccgtcaata    4560
tttaccttcc ctccctcaat cggttgaatg tcgcccttttt gtctttggcg ctggtaaacc    4620
atatgaattt tctattgatt gtgacaaaat aaacttattc cgtggtgtct ttgcgtttct    4680
tttatatgtt gccaccttta tgtatgtatt ttctacgttt gctaacatac tgcgtaataa    4740
ggagtcttaa tgatctagag gcctgtgcta atgatcagct agcttgaggc atcaataaaa    4800
cgaaaggctc agtcgaaaga ctgggccttt cgttttatct gttgtttgtc ggttaacgtc    4860
gacc                                                                 4864
```

<210> SEQ ID NO 30
<211> LENGTH: 9206
<212> TYPE: DNA
<213> ORGANISM: Artificial
<220> FEATURE:
<223> OTHER INFORMATION: Filamentous phage display vector fUSE5,
      complete sequence

<400> SEQUENCE: 30

```
aacgctacta ccattagtag aattgatgcc acctttcag ctcgcgcccc aaatgaaaat     60
atagctaaac aggttattga ccatttgcga aatgtatcta atggtcaaac taaatctact    120
cgttcgcaga attgggaatc aactgttaca tggaatgaaa cttccagaca ccgtacttta    180
gttgcatatt taaaacatgt tgaactacag caccagattc agcaattaag ctctaagcca    240
tccgcaaaaa tgacctctta tcaaaaggag caattaaagg tactgtctaa tcctgacctg    300
ttggaatttg cttccggtct ggttcgcttt gaggctcgaa ttgaaacgcg atatttgaag    360
tctttcgggc ttcctcttaa tcttttttgat gcaattcgct ttgcttctga ctataataga    420
cagggtaaag acctgatttt tgatttatgg tcattctcgt tttctgaact gtttaaagca    480
tttgaggggg attcaatgaa tatttatgac gattccgcag tattggacgc tatccagtct    540
aaacatttta caattacccc ctctggcaaa acttcctttg caaaagcctc tcgctatttt    600
ggtttctatc gtcgtctggt aatgagggt tatgatagtg ttgctcttac catgcctcgt    660
aattcctttt ggcgttatgt atctgcatta gttgagtgtg gtattcctaa atctcaattg    720
atgaatcttt ccacctgtaa taatgttgtt ccgttagttc gttttattaa cgtagatttt    780
tcctcccaac gtcctgactg gtataatgag ccagttctta aaatcgcata aggtaattca    840
aaatgattaa agttgaaatt aaaccgtctc aagcgcaatt tactaccgt tctggtgttt    900 ctcgtcaggg caagccttat tcactgaatg agcagctttg ttacgttgat tgggtaatg    960 aatatccggt tgttgtcaag attactctcg acgaaggtca gccagcgtat gcgcctggtc    1020
tgtacaccgt gcatctgtcc tcgttcaaag ttggtcagtt cggttctctt atgattgacc    1080
gtctgcgcct cgttccggct aagtaacatg gagcaggtcg cggatttcga cacaatttat    1140
caggcgatga tacaaatctc cgttgtactt tgtttcgcgc ttggtataat cgctgggggt    1200
caaagatgag tgttttagtg tattctttcg cctctttcgt tttaggttgg tgccttcgta    1260
```

```
gtggcattac gtattttacc cgtttaatgg aaacttcctc atgaaaaagt ctttagtcct    1320
caaagcctcc gtagccgttg ctaccctcgt tccgatgctg tctttcgctg ctgagggtga    1380
cgatcccgca aaagcggcct ttgactccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaccga tacaattaaa ggctccttttt ggagcctttt    1560 tttttggaga ttttcaacgt gaaaaaatta ttattcgcaa ttcctttagt tgttcctttc    1620
tattctcact cggccgacgt ggcctggcct ctggggccga aactgttgaa agttgtttag    1680
caaaacctca tacagaaaat tcatttacta acgtctggaa agacgacaaa actttagatc    1740
gttacgctaa ctatgagggc tgtctgtgga atgctacagg cgttgtggtt tgtactggtg    1800
acgaaactca gtgttacggt acatgggttc ctattgggct tgctatccct gaaaatgagg    1860
gtggtggctc tgagggtggc ggttctgagg gtggcggttc tgagggtggc ggtactaaac    1920
ctcctgagta cggtgataca cctattccgg gctatactta tatcaaccct ctcgacggca    1980
cttatccgcc tggtactgag caaaaccccg ctaatcctaa tccttctctt gaggagtctc    2040
agcctcttaa tactttcatg tttcagaata ataggttccg aaataggcag ggtgcattaa    2100
ctgtttatac gggcactgtt actcaaggca ctgaccccgt taaaacttat taccagtaca    2160
ctcctgtatc atcaaaagcc atgtatgacg cttactggaa cggtaaattc agagactgcg    2220
ctttccattc tggctttaat gaggatccat tcgtttgtga atatcaaggc caatcgtctg    2280
acctgcctca acctcctgtc aatgctggcg gcggctctgg tggtggttct ggtggcggct    2340
ctgagggtgg cggctctgag ggtggcggtt ctgagggtgg cggctctgag ggtggcggtt    2400
ccggtggcgg ctccggttcc ggtgattttg attatgaaaa aatggcaaac gctaataagg    2460
gggctatgac cgaaaatgcc gatgaaaacg cgctacagtc tgacgctaaa ggcaaacttg    2520
attctgtcgc tactgattac ggtgctgcta tcgatggttt cattggtgac gtttccggcc    2580
ttgctaatgg taatggtgct actggtgatt ttgctggctc taattcccaa atggctcaag    2640
tcggtgacgg tgataattca cctttaatga ataatttccg tcaatattta ccttctttgc    2700
ctcagtcggt tgaatgtcgc ccttatgtct ttggcgctgg taaaccatat gaattttcta    2760
ttgattgtga caaaataaac ttattccgtg gtgtctttgc gtttctttta tatgttgcca    2820
cctttatgta tgtattttcg acgtttgcta acatactgcg taataaggag tcttaatcat    2880
gccagttctt tgggtattc cgttattatt gcgtttcctc ggtttccttc tggtaacttt    2940
gttcggctat ctgcttactt tccttaaaaa gggcttcggt aagatagcta ttgctatttc    3000
attgtttctt gctcttatta ttgggcttaa ctcaattctt gtgggttatc tctctgatat    3060
tagcgcacaa ttaccctctg attttgttca gggcgttcag ttaattctcc cgtcaatgc    3120 gcttccctgt ttttatgtta ttctctctgt aaaggctgct attttcattt ttgacgttaa    3180
acaaaaaatc gtttcttatt tggattggga taaataaata tggctgtttta ttttgtaact    3240 ggcaaattag gctctggaaa gacgctcgtt agcgttggta agattcagga taaaattgta    3300
gctgggtgca aaatagcaac taatcttgat ttaaggcttc aaaacctccc gcaagtcggg    3360
aggttcgcta aaacgcctcg cgttcttaga ataccggata agccttctat ttctgatttg    3420
cttgctattg gtcgtggtaa tgattcctac gacgaaaata aaaacggttt gcttgttctt    3480
gatgaatgcg gtacttggtt taatacccgt tcatggaatg acaaggaaag acagccgatt    3540
attgattggt tcttcatgc tcgtaaattg ggatgggata ttatttttct tgttcaggat    3600
ttatctattg ttgataaaca ggcgcgttct gcattagctg aacacgttgt ttattgtcgc    3660
```

```
cgtctggaca gaattacttt acccttttgtc ggcactttat attctcttgt tactggctca    3720
aaaatgcctc tgcctaaatt acatgttggt gttgttaaat atggtgattc tcaattaagc    3780
cctactgttg agcgttggct ttatactggt aagaatttat ataacgcata tgacactaaa    3840
caggcttttt ccagtaatta tgattcaggt gtttattcat atttaacccc ttatttatca    3900
cacggtcggt atttcaaacc attaaattta ggtcagaaga tgaaattaac taaaatatat    3960
ttgaaaaagt tttctcgcgt tctttgtctt gcgataggtt tgcatcagc atttacatat    4020 agttatataa cccaacctaa gccggaggtt aaaaaggtag tctctcagac ctatgatttt    4080
gataaattca ctattgactc ttctcagcgt cttaatctaa gctatcgcta tgttttcaag    4140
gattctaagg gaaaattaat taatagcgac gatttacaga agcaaggtta ttccatcaca    4200
tatattgatt tatgtactgt ttcaattaaa aaggtaatt caaatgaaat tgttaaatgt    4260
aattaatttt gttttcttga tgtttgtttc atcatcttct tttgctcaag taattgaaat    4320
gaataattcg cctctgcgcg atttcgtgac ttggtattca aagcaaacag gtgaatctgt    4380
tattgtctca cctgatgtta aaggtacagt gactgtatat tcctctgacg ttaagcctga    4440
aaatttacgc aatttcttta tctctgtttt acgtgctaat aattttgata tggttggctc    4500
aattccttcc ataattcaga aatataaccc aaatagtcag gattatattg atgaattgcc    4560
atcatctgat attcaggaat atgatgataa ttccgctcct tctggtggtt tctttgttcc    4620
gcaaaatgat aatgttactc aaacatttaa aattaataac gttcgcgcaa aggatttaat    4680
aagggttgta gaattgtttg ttaaatctaa tacatctaaa tcctcaaatg tattatctgt    4740
tgatggttct aacttattag tagttagcgc ccctaaagat attttagata accttccgca    4800 atttcttctct actgttgatt tgccaactga ccagatattg attgaaggat taattttcga    4860
ggttcagcaa ggtgatgctt tagatttttc ctttgctgct ggctctcagc gcggcactgt    4920
tgctggtggt gttaatactg accgtctaac ctctgtttta tcttctgcgg gtggttcgtt    4980
cggtattttt aacggcgatg ttttagggct atcagttcgc gcattaaaga ctaatagcca    5040
ttcaaaaata ttgtctgtgc ctcgtattct tacgctttca ggtcagaagg gttctatttc    5100
tgttggccag aatgtccctt ttattactgg tcgtgtaact ggtgaatctg ccaatgtaaa    5160
taatccattt cagacggttg agcgtcaaaa tgttggtatt tctatgagtg ttttttcccgt    5220 tgcaatggct ggcggtaata ttgttttaga tataaccagt aaggccgata gtttgagttc    5280
ttctactcag gcaagtgatg ttattactaa tcaaagaagt attgcgacaa cggttaattt    5340
gcgtgatggt cagactcttt tgctcggtgg cctcactgat tacaaaaaca cttctcaaga    5400
ttctggtgtg ccgttcctgt ctaaaatccc tttaatcggc ctcctgttta gctcccgttc    5460
tgattctaac gaggaaagca cgttatacgt gctcgtcaaa gcaaccatag tacgcgccct    5520
gtagcggcgc attaagcgcg gcgggtgtgg tggttacgcg cagcgtgacc gctacacttg    5580
ccagcgccct agcgcccgct cctttcgctt tcttcccttc ctttctcgcc acgttctccg    5640
gctttccccg tcaagctcta aatcggggga tctcgggaaa agcgttggtg accaaaggtg    5700 cctttttatca tcacttttaaa aataaaaaac aattactcag tgcctgttat aagcagcaat    5760
taattatgat tgatgcctac atcacaacaa aaactgattt aacaaatggt tggtctgcct    5820
tagaaagtat atttgaacat tatcttgatt atattattga taataataaa aaccttatcc    5880
ctatccaaga agtgatgcct atcattggtt ggaatgaact tgaaaaaatt agccttgaat    5940
acattactgg taaggtaaac gccattgtca gcaaattgat ccaagagaac caacttaaag    6000
cttatgatga tgatgtgctt aaaaaacttac tcaatggctg gtttatgcat atcgcaatac    6060
```

```
atgcgaaaaa cctaaaagag cttgccgata aaaaggcca atttattgct atttaccgcg    6120 gcttttatt gagcttgaaa gataaataaa atagataggt tttatttgaa gctaaatctt    6180
ctttatcgta aaaaatgccc tcttgggtta tcaagagggt cattatattt cgcggaataa    6240
catcatttgg tgacgaaata actaagcact tgtctcctgt ttactcccct gagcttgagg    6300
ggttaacatg aaggtcatcg atagcaggat aataatacag taaaacgcta aaccaataat    6360
ccaaatccag ccatcccaaa ttggtagtga atgattataa ataacagcaa acagtaatgg    6420
gccaataaca ccggttgcat tggtaaggct caccaataat ccctgtaaag caccttgctg    6480
atgactcttt gtttggatag acatcactcc ctgtaatgca ggtaaagcga tcccaccacc    6540
agccaataaa attaaaacag ggaaaactaa ccaaccttca gatataaacg ctaaaaaggc    6600
aaatgcacta ctatctgcaa taaatccgag cagtactgcc gttttttcgc cccatttagt    6660
ggctattctt cctgccacaa aggcttggaa tactgagtgt aaaagaccaa gacccgctaa    6720
tgaaaagcca accatcatgc tattccatcc aaaacgattt tcggtaaata gcacccacac    6780
cgttgcggga atttggccta tcaattgcgc tgaaaaataa ataatcaaca aaatgggcat    6840
cgttttaaat aaagtgatgt ataccgaatt cgattgcgtc tcaacccta cttcggtatc     6900 tgtattatca cgtgtatttt tggtttcacg gaaccaaaac ataaccacaa ggaaagtgac    6960
aatatttagc aacgcagcga taaaaaaggg actatgcggt gaaatctctc ctgcaaaacc    7020
accaataata ggccccgcta ttaaaccaag cccaaaactt gccctaacc aaccgaacca     7080 cttcacgcgt tgagaagctg aggtggtatc ggcaatgacc gatgccgcga cagccccagt    7140
agctcctgtg atccctgaaa gcaaacggcc taaatacagc atccaaagcg cacttgaaaa    7200
agccagcaat aagtaatcca gcgatgcgcc tattaatgac aacaacagca ctgggcgccg    7260
accaaatcgg tcagacattt ttccaagcca aggagcaaag ataacctgca ttaacgcata    7320
aagtgcaagc aatacgccaa agtggttagc gatatcttcc gaagcaataa attcacgtaa    7380
taacgttggc aagactggca tgataaggcc aatccccatg gcatcgagta acgtaattac    7440
caatgcgatc tttgtcgaac tattcatttc acttttctct atcactgata gggagtggta    7500
aaataactct atcaatgata gagtgtcaac aaaaattagg aattaatgat gtctagatta    7560
gataaaagta aagtgattaa cagcgcatta gagctgctta atgaggtcgg aatcgaaggt    7620
ttaacaaccc gtaaactcgc ccagaagcta ggtgtagagc agcctacatt gtattggcat    7680
gtaaaaaata gcgggctttt gctcgacgcc ttagccattg atgttagat aggcaccat     7740 actcactttt gcccttta1aga aggggaaagc tggcaagatt ttttacgtaa taacgctaaa    7800
agttttagat gtgctttact aagtcatcgc gatggagcaa agtacatttt aggtacacgg    7860
cctacagaaa aacagtatga aactctcgaa atcaattag ccttttttatg ccaacaaggt     7920 ttttcactag agaatgcatt atatgcactc agcgctgtgg ggcatttac tttaggttgc      7980 gtattggaag atcaagagca tcaagtcgct aaagaagaaa gggaaacacc tactactgat    8040
agtatgccgc cattattacg acaagctatc gaattatttg atcaccaagg tgcagagcca    8100
gccttcttat tcggccttga attgatcata tgcggattag aaaaacaact taaatgtgaa    8160
agtgggtctt aaaagcagca taaccttttt ccgtgatggt aacttcacgg taaccaagat    8220
gtcgagttaa ccacccttta gattcataaa gcgaaaataa tgcggctcca acgtacccac    8280
ctaaatggaa acggcgttca ctccaatcta aacacgcaca acagattta cgtgaatgtt    8340 tggaaggaac gtcaattccc atttcatgaa aatattgaat accacttaat gtgatcattg    8400 aaccatttc agtgatccat tgctgttgac aaagggaatc atagatccct ttagggttcc     8460
```

-continued

```
gatttagtgc tttacggcac ctcgacctcc aaaaacttga tttgggtgat ggttcacgta      8520
gtgggccatc gccctgatag acggttttc gcccttttgac gttggagtcc acgttcttta     8580
atagtggact cttgttccaa actggaacaa cactcacaac taactcggcc tattcttttg     8640
atttataagg attttttgtca ttttctgctt actggtaaaa aaataagctg atttaacaaa    8700
tatttaacgc gaaatttaac aaaacattaa cgtttacaat ttaaatattt gcttatacaa     8760
tcatcctgtt tttggggctt ttctgattat caatcggggt acatatgatt gacatgctag     8820
ttttacgatt accgttcatc gattctcttg tttgctccag actttcaggt aatgacctga     8880
tagcctttgt agacctctca aaaatagcta ccctctccgg catgaattta tcagctagaa     8940
cggttgaata tcatattgac ggtgatttga ctgtctccgg cctttctcac ccgtttgaat    9000
ctttgcctac tcattactcc ggcattgcat ttaaaatata tgagggttct aaaaattttt    9060
atccctgcgt tgaaattaag gcttcaccag caaaagtatt acagggtcat aatgtttttg    9120
gtacaaccga tttagcttta tgctctgagg ctttattgct taatttttgct aactctctgc   9180 cttgcttgta cgatttattg gatgtt                                          9206
```

<210> SEQ ID NO 31
<211> LENGTH: 8669
<212> TYPE: DNA
<213> ORGANISM: Artificial
<220> FEATURE:
<223> OTHER INFORMATION: Cloning vector M13KO7, complete sequence

<400> SEQUENCE: 31

```
aacgctacta ctattagtag aattgatgcc accttttcag ctcgcgcccc aaatgaaaat     60
atagctaaac aggttattga ccatttgcga aatgtatcta atggtcaaac taaatctact    120
cgttcgcaga attgggaatc aactgttaca tggaatgaaa cttccagaca ccgtacttta    180
gttgcatatt taaaacatgt tgagctacag caccagattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tcttttttgat gcaatccgct ttgcttctga ctataatagt    420
cagggtaaag acctgatttt tgatttatgg tcattctcgt tttctgaact gtttaaagca    480
tttgaggggg attcaatgaa tatttatgac gattccgcag tattggacgc tatccagtct    540
aaacatttta ctattacccc ctctggcaaa acttcttttg caaaagcctc tcgctatttt    600 ggttttttatc gtcgtctggt aaacgagggt tatgatagtg ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc    1020
tgtacaccgt tcatctgtcc tctttcaaag ttggtcagtt cggttccctt atgattgacc    1080
gtctgcgcct cgttccggct aagtaacatg gagcaggtcg cggatttcga cacaatttat    1140
caggcgatga tacaaatctc cgttgtactt tgtttcgcgc ttggtataat cgctggggt     1200 caaagatgag tgttttagtg tattctttcg cctctttcgt tttaggttgg tgccttcgta    1260
gtggcattac gtattttacc cgtttaatgg aaacttcctc atgaaaaagt ctttagtcct    1320
```

```
caaagcctct gtagccgttg ctaccctcgt tccgatgctg tctttcgctg ctgagggtga    1380
cgatcccgca aaagcggcct ttaactccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaccga tacaattaaa ggctcctttt ggagcctttt    1560
tttttggaga ttttcaacgt gaaaaaatta ttattcgcaa ttcctttagt tgttcctttc    1620
tattctcact ccgctgaaac tgttgaaagt tgtttagcaa acccccatac agaaaattca    1680
tttactaacg tctggaaaga cgacaaaact ttagatcgtt acgctaacta tgagggttgt    1740
ctgtggaatg ctacaggcgt tgtagtttgt actggtgacg aaactcagtg ttacggtaca    1800
tgggttccta ttgggcttgc tatccctgaa aatgagggtg gtggctctga gggtggcggt    1860
tctgagggtg gcggttctga gggtggcggt actaaacctc ctgagtacgg tgatacacct    1920
attccgggct atacttatat caaccctctc gacggcactt atccgcctgg tactgagcaa    1980
aaccccgcta atcctaatcc ttctcttgag gagtctcagc ctcttaatac tttcatgttt    2040
cagaataata ggttccgaaa taggcagggg gcattaactg tttatacggg cactgttact    2100
caaggcactg accccgttaa aacttattac cagtacactc ctgtatcatc aaaagccatg    2160
tatgacgctt actggaacgg taaattcaga gactgcgctt ccattctggc tttaatgag    2220
gatccattcg tttgtgaata tcaaggccaa tcgtctgacc tgcctcaacc tcctgtcaat    2280
gctggcggcg gctctggtgg tggttctggt ggcggctctg agggtggtgg ctctgagggt    2340
ggcggttctg agggtggcgg ctctgaggga ggcggttccg gtggtggctc tggttccggt    2400
gattttgatt atgaaaagat ggcaaacgct aataagggg ctatgaccga aaatgccgat    2460
gaaaacgcgc tacagtctga cgctaaaggc aaacttgatt ctgtcgctac tgattacggt    2520
gctgctatcg atggtttcat tggtgacgtt tccggccttg ctaatggtaa tggtgctact    2580
ggtgattttg ctggctctaa ttcccaaatg gctcaagtcg gtgacggtga taattcacct    2640
ttaatgaata atttccgtca atatttacct tccctccctc aatcggttga atgtcgccct    2700
tttgtcttta gcgctggtaa accatatgaa ttttctattg attgtgacaa aataaactta    2760
ttccgtggtg tctttgcgtt tcttttatat gttgccacct ttatgtatgt attttctacg    2820
tttgctaaca tactgcgtaa taaggagtct taatcatgcc agttcttttg ggtattccgt    2880
tattattgcg tttcctcggt ttccttctgg taactttgtt cggctatctg cttacttttc    2940
ttaaaaaggg cttcggtaag atagctattg ctatttcatt gtttcttgct cttattattg    3000
ggcttaactc aattcttgtg ggttatctct ctgatattag cgctcaatta ccctctgact    3060
ttgttcaggg tgttcagtta attctcccgt ctaatgcgct tccctgtttt tatgttattc    3120
tctctgtaaa ggctgctatt ttcattttg acgttaaaca aaaaatcgtt tcttatttgg    3180
attgggataa ataatatggc tgtttatttt gtaactggca aattaggctc tggaaagacg    3240
ctcgttagcg ttggtaagat tcaggataaa attgtagctg ggtgcaaaat agcaactaat    3300
cttgatttaa ggcttcaaaa cctcccgcaa gtcgggaggt tcgctaaaac gcctcgcgtt    3360
cttagaatac cggataagcc ttctatatct gatttgcttg ctattgggcg cggtaatgat    3420
tcctacgatg aaaataaaaa cggcttgctt gttctcgatg agtgcggtac ttggtttaat    3480
acccgttctt ggaatgataa ggaaagacag ccgattattg attggtttct acatgctcgt    3540
aaattaggat gggatattat ttttcttgtt caggacttat ctattgttga taaacaggcg    3600
cgttctgcat tagctgaaca tgttgtttat tgtcgtcgtc tggacagaat tactttacct    3660
tttgtcggta ctttatattc tcttattact ggctcgaaaa tgcctctgcc taaattacat    3720
```

```
gttggcgttg ttaaatatgg cgattctcaa ttaagcccta ctgttgagcg ttggctttat    3780
actggtaaga atttgtataa cgcatatgat actaaacagg cttttttctag taattatgat    3840 tccggtgttt attcttattt aacgccttat ttatcacacg gtcggtattt caaaccatta    3900
aatttaggtc agaagatgaa attaactaaa atatatttga aaaagttttc tcgcgttctt    3960
tgtcttgcga ttggatttgc atcagcattt acatatagtt ataaccca acctaagccg      4020 gaggttaaaa aggtagtctc tcagacctat gattttgata aattcactat tgactcttct    4080
cagcgtctta atctaagcta tcgctatgtt ttcaaggatt ctaagggaaa attaattaat    4140
agcgacgatt tacagaagca aggttattca ctcacatata ttgatttatg tactgttttcc   4200 attaaaaaag gtaattcaaa tgaaattgtt aaatgtaatt aattttgttt tcttgatgtt    4260
tgtttcatca tcttcttttg ctcaggtaat tgaaatgaat aattcgcctc tgcgcgattt    4320
tgtaacttgg tattcaaagc aatcaggcga atccgttatt gtttctcccg atgtaaaagg    4380
tactgttact gtatattcat ctgacgttaa acctgaaaat ctacgcaatt tctttatttc    4440
tgttttacgt gctaataatt ttgatatggt tggttcaatt ccttccataa ttcagaagta    4500
taatccaaac aatcaggatt atattgatga attgccatca tctgataatc aggaatatga    4560
tgataattcc gctccttctg gtggtttctt tgttccgcaa aatgataatg ttactcaaac    4620
ttttaaaatt aataacgttc gggcaaagga tttaatacga gttgtcgaat tgtttgtaaa    4680
gtctaatact tctaaatcct caaatgtatt atctattgac ggctctaatc tattagttgt    4740
tagtgcacct aaagatattt tagataacct tcctcaattc ctttctactg ttgatttgcc    4800
aactgaccag atattgattg agggtttgat atttgaggtt cagcaaggtg atgctttaga    4860
tttttcattt gctgctggct ctcagcgtgg cactgttgca ggcggtgtta atactgaccg    4920
cctcacctct gttttatctt ctgctggtgg ttcgttcggt attttaatg gcgatgtttt    4980 agggctatca gttcgcgcat taaagactaa tagccattca aaaatattgt ctgtgccacg    5040
tattcttacg ctttcaggtc agaagggttc tatctctgtt ggccagaatg tcccttttat    5100
tactggtcgt gtgactggtg aatctgccaa tgtaaataat ccatttcaga cgattgagcg    5160
tcaaaatgta ggtatttcca tgagcgtttt tcctgttgca atggctggcg gtaatattgt    5220
tctggatatt accagcaagg ccgatagttt gagttcttct actcaggcaa gtgatgttat    5280
tactaatcaa agaagtattg ctacaacggt taatttgcgt gatggacaga ctcttttact    5340
cggtggcctc actgattata aaaacacttc tcaagattct ggcgtaccgt tcctgtctaa    5400
aatcccttta atcggcctcc tgtttagctc ccgctctgat tccaacgagg aaagcacgtt    5460
atacgtgctc gtcaaagcaa ccatagtacg cgccctgtag cggcgcatta agcgcggcgg    5520
gtgtggtggt tacgcgcagc gtgaccgcta cacttgccag cgccctagcg cccgctcctt    5580
tcgctttctt cccttccttt ctcgccacgt tcgccggctt tccccgtcaa gctctaaatc    5640
gggggctccc tttagggttc cgatttagtg ctttacggca cctcgacccc aaaaaacttg    5700
atttgggtga tggttcacgt agtgggccat cgccctgata cacggttttt cgccctttga    5760
cgttggagtc cacgttcttt aatagtggac tcttgttcca aactggaaca cactcaacc    5820 ctatctcggg acggatcgct tcatgtgca ggagaaaaaa ggctgcaccg gtgcgtcagc     5880
agaatatgtg atacaggata tattccgctt cctcgctcac tgactcgcta cgctcggtcg    5940
ttcgactgcg gcgagcggaa atggcttacg aacggggcgg agatttcctg gaagatgcca    6000
ggaagatact taacagggaa gtgagagggc cgcggcaaag ccgtttttcc ataggctccg    6060 ccccccctgac aagcatcacg aaatctgacg ctcaaatcag tggtggcgaa acccgacagg    6120
```

```
actataaaga taccaggcgt ttcccctgg cggctccctc gtgcgctctc ctgttcctgc    6180
cttttcggttt accggtgtca ttccgctgtt atggccgcgt ttgtctcatt ccacgcctga   6240
cactcagttc cgggtaggca gttcgctcca agctggactg tatgcacgaa cccccgttc    6300
agtccgaccg ctgcgcctta tccggtaact atcgtcttga gtccaacccg gaaagacatg   6360
caaaagcacc actggcagca gccactggta attgatttag aggagttagt cttgaagtca   6420
tgcgccggtt aaggctaaac tgaaaggaca gttttggtg actgcgctcc tccaagccag    6480
ttacctcggt tcaaagagtt ggtagctcag agaaccttcg aaaaaccgcc ctgcaaggcg   6540
gttttttcgt tttcagagca agagattacg cgcagaccaa aacgatctca agaagatcat   6600
cttattaagg ggtctgacgc tcagtggaac gaaaactcac gttaagggat tttggtcatg   6660
agattatcaa aaaggatctt cacctagatc cttttaaatt aaaaatgaag ttttaaatca   6720
atctaaagta tatatgagta aacttggtct gacagttacc aatgcttaat cagtgaggca   6780
cctatctcag cgatctgtct atttcgttca tccatagttg cctgactccc cgtcgtgtag   6840
ataactacga tacgggaggg cttaccatct ggccccagtg ctgcaatgat accgcgagac   6900
ccacgctcac cggctccaga tttatcagca ataaaccagc cagccgattc gagctcgccc   6960
cggggatcga ccagttggtg attttgaact tttgctttgc cacggaacgg tctgcgttgt   7020
cgggaagatg cgtgatctga tccttcaact cagcaaaagt tcgatttatt caacaaagcc   7080
gccgtcccgt caagtcagcg taatgctctg ccagtgttac aaccaattaa ccaattctga   7140
ttagaaaaac tcatcgagca tcaaatgaaa ctgcaattta ttcatatcag gattatcaat   7200
accatatttt tgaaaagcc gtttctgtaa tgaaggagaa aactcaccga ggcagttcca   7260
taggatggca agatcctggt atcggtctgc gattccgact cgtccaacat caatacaacc   7320
tattaatttc ccctcgtcaa aaataaggtt atcaagtgag aaatcaccat gagtgacgac   7380
tgaatccggt gagaatggca aaagcttatg catttctttc cagacttgtt caacaggcca   7440
gccattacgc tcgtcatcaa aatcactcgc atcaaccaaa ccgttattca ttcgtgattg   7500
cgcctgagcg agacgaaata cgcgatcgct gttaaaagga caattacaaa caggaatcga   7560
atgcaaccgg cgcaggaaca ctgccagcgc atcaacaata ttttcacctg aatcaggata   7620
ttcttctaat acctggaatg ctgttttccc ggggatcgca gtggtgagta accatgcatc   7680
atcaggagta cggataaaat gcttgatggt cggaagaggc ataaattccg tcagccagtt   7740
tagtctgacc atctcatctg taacatcatt ggcaacgcta cctttgccat gtttcagaaa   7800
caactctggc gcatcgggct tcccatacaa tcgatagatt gtcgcacctg attgcccgac   7860
attatcgcga gcccatttat acccatataa atcagcatcc atgttggaat ttaatcgcgg   7920
cctcgagcaa gacgtttccc gttgaatatg gctcataaca ccccttgtat tactgtttat   7980
gtaagcagac agttttattg ttcatgatga tatatttta tcttgtgcaa tgtaacatca   8040
gagattttga gacacaacgt ggctttcccc ccccccccct gcaggtctcg gctattctt   8100
ttgatttata agggatttg ccgatttcgg cctattggtt aaaaaatgag ctgatttaac   8160
aaaaatttaa cgcgaatttt aacaaaatat taacgtttac aatttaaata tttgcttata   8220
caatcttcct gttttgggg cttttctgat tatcaaccgg ggtacatatg attgacatgc   8280
tagttttacg attaccgttc atcgattctc ttgtttgctc cagactctca ggcaatgacc   8340
tgatagcctt tgtagacctc tcaaaaatag ctaccctctc cggcatgaat ttatcagcta   8400
gaacggttga atatcatatt gatggtgatt tgactgtctc cggcctttct cacccttttg   8460
aatctttacc tacacattac tcaggcattg catttaaaat atgagggt tctaaaaatt    8520
```

-continued

```
tttatccttg cgttgaaata aaggcttctc ccgcaaaagt attacagggt cataatgttt    8580
ttggtacaac cgatttagct ttatgctctg aggcttatt gcttaatttt gctaattctt     8640
tgccttgcct gtatgattta ttggatgtt                                      8669
```

<210> SEQ ID NO 32
<211> LENGTH: 8669
<212> TYPE: DNA
<213> ORGANISM: Artificial
<220> FEATURE:
<223> OTHER INFORMATION: VCSM13 interference-resistant helper phage, complete genome.

<400> SEQUENCE: 32

```
tgcctgactc cccgtcgtgt agataactac gatacgggag ggcttaccat ctggccccag      60
tgctgcaatg ataccgcgag acccacgctc accggctcca gatttatcag caataaacca    120
gccagccgat tcgagctcgc ccggggatcg accagttggt gattttgaac ttttgctttg    180
ccacggaacg gtctgcgttg tcgggaagat gcgtgatctg atccttcaac tcagcaaaag    240
ttcgatttat tcaacaaagc cgccgtcccg tcaagtcagc gtaatgctct gccagtgtta    300
caaccaatta accaattctg attagaaaaa ctcatcgagc atcaaatgaa actgcaattt    360
attcatatca ggattatcaa taccatattt tgaaaaagc cgtttctgta atgaaggaga     420
aaactcaccg aggcagttcc ataggatggc aagatcctgg tatcggtctg cgattccgac    480
tcgtccaaca tcaatacaac ctattaattt cccctcgtca aaataaggt tatcaagtga     540 gaaatcacca tgagtgacga ctgaatccgg tgagaatggc aaaagcttat gcatttcttt    600
ccagacttgt tcaacaggcc agccattacg ctcgtcatca aaatcactcg catcaaccaa    660
accgttattc attcgtgatt gcgcctgagc gagacgaaat acgcgatcgc tgttaaaagg    720
acaattacaa acaggaatcg aatgcaaccg gcgcaggaac actgccagcg catcaacaat    780
attttcacct gaatcaggat attcttctaa tacctgaat gctgtttcc cggggatcgc      840 agtggtgagt aaccatgcat catcaggagt acggataaaa tgcttgatgg tcggaagagg    900
cataaattcc gtcagccagt ttagtctgac catctcatct gtaacatcat ggcaacgct     960 accttttgcca tgtttcagaa acaactctgg cgcatcgggc ttcccataca atcgatagat   1020
tgtcgcacct gattgcccga cattatcgcg agcccattta tacccatata atcagcatc    1080 catgttggaa tttaatcgcg gcctcgagca agacgtttcc cgttgaatat ggctcataac   1140 ccccttgta ttactgttta tgtaagcaga cagttttatt gttcatgatg atatattttt     1200
atcttgtgca atgtaacatc agagattttg aaacacaacg tggctttccc cccccccccc    1260
ctgcaggtct cgggctattc ttttgattta aagggatt tgccgatttc ggcctattgg     1320
ttaaaaaatg agctgattta caaaaatt aacgcgaatt ttaacaaaat attaacgttt      1380
acaatttaaa tatttgctta tacaatcttc ctgttttgg ggcttttctt attatcaacc     1440
ggggtacata tgattgacat gctagtttta cgattaccgt tcatcgattc tcttgtttgc   1500
tccagactct caggcaatga cctgatagcc tttgtagacc tctcaaaaat agctaccctc   1560
tccggcatga atttatcagc tagaacggtt gaatatcatg ttgatggtga tttgactgtc   1620
tccggccttt ctcacccttt tgaatcttta cctacacatt actcaggcat tgcatttaaa   1680
atatatgagg gttctaaaaa ttttatcct tgcgttgaaa taaggcttc tcccgcaaaa     1740 gtattacagg gtcataatgt ttttggtaca accgatttag ctttatgctc tgaggcttta   1800
ttgcttaatt ttgctaattc tttgccttgc ctgtatgatt tattggatgt taacgctact   1860
actattagta gaattgatgc cacctttca gctcgcgccc caaatgaaaa tatagctaaa    1920
```

```
caggttattg accatttgcg aaatgtatct aatggtcaaa ctaaatctac tcgttcgcag    1980
aattgggaat caactgttac atggaatgaa acttccagac accgtacttt agttgcatat    2040
ttaaaacatg ttgagctaca gcaccagatt cagcaattaa gctctaagcc atccgcaaaa    2100
atgacctctt atcaaaagga gcaattaaag gtactctcta atcctgacct gttggagttt    2160
gcttccggtc tggttcgctt tgaagctcga attaaaacgc gatatttgaa gtctttcggg    2220
cttcctctta atcttttga tgcaatccgc tttgcttctg actataatag tcagggtaaa    2280
gacctgattt ttgatttatg gtcattctcg ttttctgaac tgtttaaagc atttgagggg    2340
gattcaatga atatttatga cgattccgca gtattggacg ctatccagtc taaacatttt    2400
actattaccc cctctggcaa aacttctttt gcaaaagcct ctcgctattt ggttttat     2460 cgtcgtctgg taaacgaggg ttatgatagt gttgctctta ctatgcctcg taattccttt    2520
tggcgttatg tatctgcatt agttgaatgt ggtattccta aatctcaact gatgaatctt    2580
tctacctgta ataatgttgt tccgttagtt cgttttatta acgtagattt tcttcccaa     2640 cgtcctgact ggtataatga gccagttctt aaaatcgcat aaggtaattc acaatgatta    2700
aagttgaaat taaaccatct caagcccaat ttactactcg ttctggtgtt tctcgtcagg    2760
gcaagcctta ttcactgaat gagcagcttt gttacgttga tttgggtaat gaatatccgg    2820
ttcttgtcaa gattactctt gatgaaggtc agccagccta tcgcctggt ctgtacaccg     2880 ttcatctgtc ctctttcaaa gttggtcagt tcggttccct tatgattgac cgtctgcgcc    2940
tcgttccggc taagtaacat ggagcaggtc gcggatttcg acacaattta tcaggcgatg    3000
atacaaatct ccgttgtact tgtttcgcg cttggtataa tcgctggggg tcaaagatga     3060 gtgtttttagt gtattctttc gcctctttcg ttttaggttg gtgccttcgt agtggcatta    3120 cgtatttac ccgtttaatg gaaacttcct catgaaaaag tctttagtcc tcaaagcctc     3180
tgtagccgtt gctaccctcg ttccgatgct gtctttcgct gctgagggtg acgatcccgc    3240
aaaagcggcc tttaactccc tgcaagcctc agcgaccgaa tatatcggtt atgcgtgggc    3300
gatggttgtt gtcattgtcg gcgcaactat cggtatcaag ctgtttaaga aattcacctc    3360
gaaagcaagc tgataaaccg atacaattaa aggctccttt tggagccttt ttttttggag    3420
attttcaacg tgaaaaaatt attattcgca attcctttag ttgttccttt ctattctcac    3480
tccgctgaaa ctgttgaaag ttgtttagca aaaccccata cagaaaattc atttactaac    3540
gtctggaaag acgacaaaac tttagatcgt tacgctaact atgagggctg tctgtggaat    3600
gctacaggcg ttgtagtttg tactggtgac gaaactcagt gttacggtac atgggttcct    3660
attgggcttg ctatccctga aaatgagggt ggtggctctg agggtggcgg ttctgagggt    3720
ggcggttctg agggtggcgg tactaaacct cctgagtacg gtgatacacc tattccgggc    3780
tatacttata tcaaccctct cgacggcact tatccgcctg gtactgagca aaaccccgct    3840
aatcctaatc cttctcttga ggagtctcag cctcttaata ctttcatgtt tcagaataat    3900
aggttccgaa ataggcaggg ggcattaact gtttatacgg gcactgttac tcaaggcact    3960
gaccccgtta aaacttatta ccagtacact cctgtatcat caaaagccat gtatgacgct    4020
tactggaacg gtaaattcag agactgcgct ttccattctg gctttaatga ggatccattc    4080
gtttgtgaat atcaaggcca atcgtctgac ctgcctcaac ctcctgtcaa tgctggcggc    4140
ggctctggtg gtggttctgg tggcggctct gagggtggtg gctctgaggg tggcggttct    4200
gagggtggcg gctctgaggg aggcggttcc ggtggtggct ctggttccgg tgattttgat    4260
tatgaaaaga tggcaaacgc taataagggg gctatgaccg aaaatgccga tgaaaacgcg    4320
```

```
ctacagtctg acgctaaagg caaacttgat tctgtcgcta ctgattacgg tgctgctatc    4380
gatggtttca ttggtgacgt ttccggcctt gctaatggta atggtgctac tggtgatttt    4440
gctggctcta attcccaaat ggctcaagtc ggtgacggtg ataattcacc tttaatgaat    4500
aatttccgtc aatatttacc ttccctccct caatcggttg aatgtcgccc ttttgtcttt    4560
ggcgctggta aaccatatga atttctatt gattgtgaca aaataaactt attccgtggt    4620
gtctttgcgt ttcttttata tgttgccacc tttatgtatg tattttctac gtttgctaac    4680
atactgcgta ataaggagtc ttaatcatgc cagttctttt gggtattccg ttattattgc    4740
gtttcctcgg tttccttctg gtaactttgt tcggctatct gcttactttt cttaaaaagg    4800
gcttcggtaa gatagctatt gctatttcat tgtttcttgc tcttattatt gggcttaact    4860
caattcttgt gggttatctc tctgatatta gcgctcaatt accctctgac tttgttcagg    4920
gtgttcagtt aattctcccg tctaatgcgc ttccctgttt ttatgttatt ctctctgtaa    4980
aggctgctat tttcattttt gacgttaaac aaaaaatcgt ttcttatttg gattgggata    5040
aataatatgg ctgtttattt tgtaactggc aaattaggct ctggaaagac gctcgttagc    5100
gttggtaaga ttcaggataa aattgtagct gggtgcaaaa tagcaactaa tcttgattta    5160
aggcttcaaa acctcccgca agtcgggagg ttcgctaaaa cgcctcgcgt tcttagaata    5220
ccggataagc cttctatatc tgatttgctt gctattgggc gcggtaatga ttcctacgat    5280
gaaaataaaa acggcttgct tgttctcgat gagtgcggta cttggtttaa tacccgttct    5340
tggaatgata aggaaagaca gccgattatt gattggtttc tacatgctcg taaattagga    5400
tgggatatta ttttcttgt tcaggactta tctattgttg ataaacaggc gcgttctgca    5460
ttagctgaac atgttgttta ttgtcgtcgt ctggacagaa ttactttacc ttttgtcggt    5520
actttatatt ctcttattac tggctcgaaa atgcctctgc ctaaattaca tgttggcgtt    5580
gttaaatatg gcgattctca attaagccct actgttgagc gttggcttta tactggtaag    5640
aatttgtata acgcatatga tactaaacag gcttttccta gtaattatga ttccggtgtt    5700
tattcttatt aacgcccctta tttatcacac ggtcggtatt tcaaaccatt aaatttaggt    5760
cagaagatga aattaactaa aatatatttg aaaaagtttt ctcgcgttct ttgtcttgcg    5820
attggatttg catcagcatt tacatatagt tatataaccc aacctaagcc ggaggttaaa    5880
aaggtagtct ctcagaccta tgattttgat aaattcacta ttgactcttc tcagcgtctt    5940
aatctaagct atcgctatgt tttcaaggat tctaagggaa aattaattaa tagcgacgat    6000
ttacagaagc aaggttattc actcacatat attgatttat gtactgtttc cattaaaaaa    6060
ggtaattcaa atgaaattgt taatgtaat taattttgtt ttcttgatgt ttgtttcatc    6120
atcttctttt gctcaggtaa ttgaaatgaa taattcgcct ctgcgcgatt ttgtaacttg    6180
gtattcaaag caatcaggcg aatccgttat tgtttctccc gatgtaaaag gtactgttac    6240
tgtatattca tctgacgtta aacctgaaaa tctacgcaat ttctttattt ctgttttacg    6300
tgcaaataat tttgatatgg taggttctaa cccttccatt attcagaagt ataatccaaa    6360
caatcaggat tatattgatg aattgccatc atctgataat caggaatatg atgataattc    6420
cgctccttct ggtggtttct tgttccgca aaatgataat gttactcaaa cttttaaaat    6480
taataacgtt cgggcaaagg atttaatacg agttgtcgaa ttgtttgtaa agtctaatac    6540
ttctaaatcc tcaaatgtat tatctattga cggctctaat ctattagttg ttagtgctcc    6600
taaagatatt ttagataacc ttcctcaatt cctttcaact gttgatttgc caactgacca    6660
```

```
gatattgatt gagggtttga tatttgaggt tcagcaaggt gatgctttag attttcatt      6720 tgctgctggc tctcagcgtg gcactgttgc aggcggtgtt aatactgacc gcctcacctc      6780
tgttttatct tctgctggtg gttcgttcgg tattttaat ggcgatgttt tagggctatc       6840
agttcgcgca ttaaagacta atagccattc aaaatattg tctgtgccac gtattcttac       6900
gctttcaggt cagaagggtt ctatctctgt tggccagaat gtccctttta ttactggtcg      6960
tgtgactggt gaatctgcca atgtaaataa tccatttcag acgattgagc gtcaaaatgt      7020
aggtatttcc atgagcgttt ttcctgttgc aatggctggc ggtaatattg ttctggatat      7080
taccagcaag gccgatagtt tgagttcttc tactcaggca agtgatgtta ttactaatca      7140 agaagtatt gctacaacgg ttaatttgcg tgatggacag actcttttac tcggtggcct       7200
cactgattat aaaaacactt ctcaggattc tggcgtaccg ttcctgtcta aaatccctt       7260 aatcggcctc ctgtttagct cccgctctga ttctaacgag gaaagcacgt tatacgtgct     7320
cgtcaaagca accatagtac gcgccctgta gcggcgcatt aagcgcggcg ggtgtggtgg     7380
ttacgcgcag cgtgaccgct acacttgcca gcgccctagc gcccgctcct ttcgctttct     7440
tcccttcctt tctcgccacg ttcgccggct ttccccgtca gctctaaat cggggctcc      7500 ctttagggt ccgatttagt gctttacggc acctcgaccc caaaaaactt gatttgggtg     7560
atggttcacg tagtgggcca tcgccctgat agacggtttt tcgccctttg acgttggagt    7620
ccacgttctt taatagtgga ctcttgttcc aaactggaac aacactcaac cctatctcgg     7680
gacggatcgc ttcatgtggc aggagaaaa aggctgcacc ggtgcgtcag cagaatatgt      7740
gatacaggat atattccgct tcctcgctca ctgactcgct acgctcggtc gttcgactgc    7800
ggcgagcgga atggcttacg aacggggcg gagatttcct ggaagatgcc aggaagatac     7860
ttaacaggga agtgagaggg ccgcggcaaa gccgttttc cataggctcc gccccctga      7920 caagcatcac gaaatctgac gctcaaatca gtggtggcga acccgacag gactataaag     7980 ataccaggcg tttcccctg gcggctccc cgtgcgctct cctgttcctg cctttcggt      8040 taccggtgtc attccgctgt tatggccgcg tttgtctcat tccacgcctg acactcagtt     8100
ccgggtaggc agttcgctcc aagctggact gtatgcacga accccccgtt cagtccgacc    8160
gctgcgcctt atccggtaac tatcgtcttg agtccaaccc ggaaagacat gcaaaagcac    8220
cactggcagc agccactggt aattgattta gaggagttag tcttgaagtc atgcgccgt     8280 taaggctaaa ctgaaaggac aagttttggt gactgcgctc ctccaagcca gttacctcgg    8340
ttcaaagagt tggtagctca gagaaccttc gaaaaccgc cctgcaaggc ggttttttcg     8400
ttttcagagc aagagattac gcgcagacca aacgatctc aagaagatca tcttattaag    8460
gggtctgacg ctcagtggaa cgaaaactca cgttaaggga ttttggtcat gagattatca     8520
aaaaggatct tcacctagat ccttttaaat taaaatgaa gttttaaatc aatctaaagt     8580
atatatgagt aaacttggtc tgacagttac caatgcttaa tcagtgaggc acctatctca     8640
gcgatctgtc tatttcgttc atccatagt                                       8669
```

<210> SEQ ID NO 33
<211> LENGTH: 22
<212> TYPE: PRT
<213> ORGANISM: Artificial
<220> FEATURE:
<223> OTHER INFORMATION: signal sequence

```
<400> SEQUENCE: 33

Met Lys Tyr Leu Leu Pro Thr Ala Ala Ala Gly Leu Leu Leu Ala
1               5                   10                  15

Ala Gln Pro Ala Met Ala
            20

<210> SEQ ID NO 34
<211> LENGTH: 45
<212> TYPE: DNA
<213> ORGANISM: Artificial Sequence
<220> FEATURE:
<223> OTHER INFORMATION: Sequence Tags

<400> SEQUENCE: 34
ggtctgaacg acatcttcga ggctcagaaa atcgaatggc acgaa            45

<210> SEQ ID NO 35
<211> LENGTH: 45
<212> TYPE: DNA
<213> ORGANISM: Artificial Sequence
<220> FEATURE:
<223> OTHER INFORMATION: Sequence Tags

<400> SEQUENCE: 35
ggcctgaacg atatctttga agcccagaaa attgaatggc atgaa            45

<210> SEQ ID NO 36
<211> LENGTH: 15
<212> TYPE: PRT
<213> ORGANISM: Artificial Sequence
<220> FEATURE:
<223> OTHER INFORMATION: Sequence Tags

<400> SEQUENCE: 36

Gly Leu Asn Asp Ile Phe Glu Ala Gln Lys Ile Glu Trp His Glu
1               5                   10                  15

<210> SEQ ID NO 37
<211> LENGTH: 24
<212> TYPE: DNA
<213> ORGANISM: Artificial Sequence
<220> FEATURE:
<223> OTHER INFORMATION: Sequence Tags

<400> SEQUENCE: 37
gactacaagg acgatgacga caag                                   24

<210> SEQ ID NO 38
<211> LENGTH: 8
<212> TYPE: PRT
<213> ORGANISM: Artificial Sequence
<220> FEATURE:
<223> OTHER INFORMATION: Sequence Tags

<400> SEQUENCE: 38

Asp Tyr Lys Asp Asp Asp Asp Lys
1               5

<210> SEQ ID NO 39
<211> LENGTH: 18
<212> TYPE: DNA
<213> ORGANISM: Artificial Sequence
<220> FEATURE:
<223> OTHER INFORMATION: Sequence Tags
```

```
<400> SEQUENCE: 39
catcaccatc accatcac                                                    18

<210> SEQ ID NO 40
<211> LENGTH: 6
<212> TYPE: PRT
<213> ORGANISM: Artificial Sequence
<220> FEATURE:
<223> OTHER INFORMATION: Sequence Tags

<400> SEQUENCE: 40

His His His His His His
1               5
```

PVII PHAGE DISPLAY

BACKGROUND OF THE INVENTION

The use of combinatorial approaches for protein identification, characterization and modification has been highly successful in both academic and commercial research and development. In this respect, filamentous bacteriophage, or phage, display technology has paved the way being the first library platform and still thrones as the dominating technology. Thus, phage display is widely applied in both basic and applied protein discovery, as well as in development of both novel protein-based diagnostics and therapeutic, which are the class of compounds most rapidly growing world-wide.

The principle of combinatorial phage display technology is based on the genotype—phenotype linkage offered by the property that each virion will only display on its surface the very same proteins that are encoded by the genome encapsulated by its protein coat. The phage particle itself is highly resistant to a variety of physiochemical conditions; hence phage display offers superior versatility in many selection regimes as compared to competing combinatorial technologies.

Phage display of heterologous polypeptides has been achieved using all five structural proteins of the filamentous phage coat, but only pIII- and to some extent pVIII-display have gained widespread use (FIG. 1).

When the heterologous fusion is only a short peptide, multivalent display systems using phage genome-based vectors are preferred, whereas for larger fusions requiring folded domains most applications will benefit from the phagemid systems. In the latter case, antibody-pIII phage display is by far dominating the field, but alternative scaffolds are emerging at dawns early light, continuing the need for expansion of protein engineering tools of tomorrow. For many applications, it would be highly advantageous to be able to make, specifically and in a controlled manner, bispecific phage particles in that more than one of the coat proteins displayed a fusion peptide in the context of the same virus particle. Also, such a system should not interfere with already established display approaches and in particular pIII and pVIII display.

Endemann and Model, 1995 (PMID: 7616570), reported that the minor coat protein pVII was not accessible in the intact phage and that pVII was not functional with another protein fused to its N-terminus. Thus, this report concluded that pVII cannot be used for phage display.

Gao et al, 1999 (PMID: 10339535) and patent application WO0071694, describes heterologous peptide phage display on pVII using the octapeptide FLAG tag, as well as simultaneous phage display on pVII and pIX to generate functional heterodimeric polypeptides harbouring complex folding topologies (antibody Fv). These authors aimed at developing an alternative means for antibody display. The pVII and pIX fusion proteins were expressed from a phagemid employing a dicistronic constellation, hence the resulting functional phage particles inevitably contained varying amounts of pVII and pIX fusion proteins due to complementation by wild type pVII and pIX protein donated from the helper phage genome. As mentioned above, it had previously been suggested that pVII and pIX were not functional with another protein fused to their N termini, and Gao et. al. gave two possible reasons for their success, either alone or by the combination of both.

One possible reason was that a prokaryotic leader sequence (signal sequence) was attached N-terminally to the fusion proteins, thus ensuring targeting of the recombinant protein to the periplasmic space and thereby prevented accumulation in the cytoplasm. Another possible reason was that the recombinant proteins were expressed from a phagemid, not a phage genome as by Endemann and Model, hence wild type pVII and pIX from the helper phage inevitably needed for phagemid rescue were complementing the recombinant pVII and pIX fusion proteins, thus preserving wildtype functionality that otherwise may have been lost due to the recombinant modification. I.e. the phages would comprise a mix of wild-type and fusion proteins. The authors mention that the pVII-pIX display format would be particular useful for combinatorial display of heterodimeric arrays, which, for unknown reasons, appear to yield a particular powerful enrichment during panning protocols. The authors do not envisage using pVII as sole displaying protein (as phagemid or phage genome) or using pVII display in combination with display at another coat protein (different from pIX) to achieve bispecific display.

Kwasnikowski et al. (PMID: 16277988) described genetically stable fusion of scFv fragments to gene VII directly in the phage genome. I.e. the resulting phages comprised no native pVII protein, and the pVII display was multivalent. The authors speculate that one of the reasons for successful pVII display in the phage genome format is that they supported the fusion gene with a prokaryotic signal sequence that directs the fusion protein to the periplasmic space. The authors argued that the unique feature of their system is that the pVII displaying phages bears unmodified, wild-type pIII minor coat protein. Since it has been reported that multiple copies of functional pIII are required for host cell infection, the presence of wild-type pIII of the phage surface may facilitate recovery of selected antibodies with larger diversity. Thus, the authors do not envisage bispecific display, nor do they envisage pVII display without a prokaryotic signal sequence targeting to the periplasmic space.

Khalil et al (PMID: 17360403) describes an application exploiting the feature of a bispecific filamentous phage virion in which an exogenous peptide is displayed at each distal tip of the very same virion. They achieved this by using the combination of a common pIII phage genome vector complementing a pIX display phagemid. In this setting, the phage genome vector served as a helper phage in rescuing the phagemid, thus being reminiscent of the approach described herein of creating a bispecific phagemid virion by rescuing a pIII display phagemid by the use of a pVII modified helper phage genome. Moreover, the bispecific virions of Khalil et al display a peptide-pIII fusion that allows for a controlled biotinylation of their virion. There are however, several features that differ between these two avenues of obtaining a bispecific virion, as well as obtaining defined virion biotinylation, which make them unique from each other.

Firstly, the approach of Khalil et al cannot be used in combination with pIII phagemid display, as it is their phage genome vector that carries their pIII fusion, hence bispecificity cannot be obtained upon phagemid rescue and it would also highly likely be deleterious to the functionality of both pIII fusions.

Secondly, and as the authors also themselves pinpoint, genomic pIX modifications are not regarded as a viable strategy due to overlapping genes in the phage genome, thus they do not envision or speculate in making any modified helper phage genome that can be used for pIII phagemid (or pVIII) rescue and by this way donate a defined phenotypic feature to both distal tips of the very same virion. Khalil et al do never mention the use of modified pVII in either phagemid, or phage genome display.

Thirdly, Khalil et al do not speculate in modifying a single phage genome to achieve a bispesific virion, by exploiting simultaneous modification of more than one capsid gene within the very same genome. They merely use standard pIII peptide display through a commercially available phage genome vector.

Forth, Khalil et al only make bispecific virions displaying short peptides, not folded domains, and do never speculate in exploiting such display at either on, or both modified capsid proteins.

Fifth, Khalil et al achieve site-specific biotinylation of their pIII displayed peptide through in vitro chemical conjugation, not by an enzymatic reaction either in vitro or in vivo. The authors never envision enzyme mediated biotinylation of a displayed moiety by displaying an enzymatic substrate such as AviTag.

Finally, does Khalil et al. not show any type of display without the use of a N-terminal signal sequence.

SUMMARY OF THE INVENTION

An object of the present invention is to provide an alternative scaffold for peptides displayed on filamentous phages.

A first aspect of the invention is a pVII fusion proteins originating from a filamentous phage, said fusion proteins does not comprise an N-terminal signal sequence and thus is a direct fusion to an exogenous peptide.

Another aspect of the invention relates to nucleic acids encoding the fusion proteins of the invention.

One aspect of the invention relates to filamentous phages comprising the fusion proteins of the invention.

Another aspect of the invention relates to a library of filamentous phages.

One aspect of the invention relates to a phage display system comprising a phagemid and a helper phage, wherein the helper phage comprises a nucleic acid encoding the pVII fusion proteins of the invention.

Another aspect of the invention relates to a phage display system comprising a phagemid and a helper phage, wherein the phagemid comprises a nucleic acid encoding the pVII fusion proteins of the invention.

One aspect relates to a kit comprising a phage display system comprising a phagemid and a helper phage, wherein the helper phage comprises a nucleic acid encoding the pVII fusion proteins of the invention.

Figure 1:
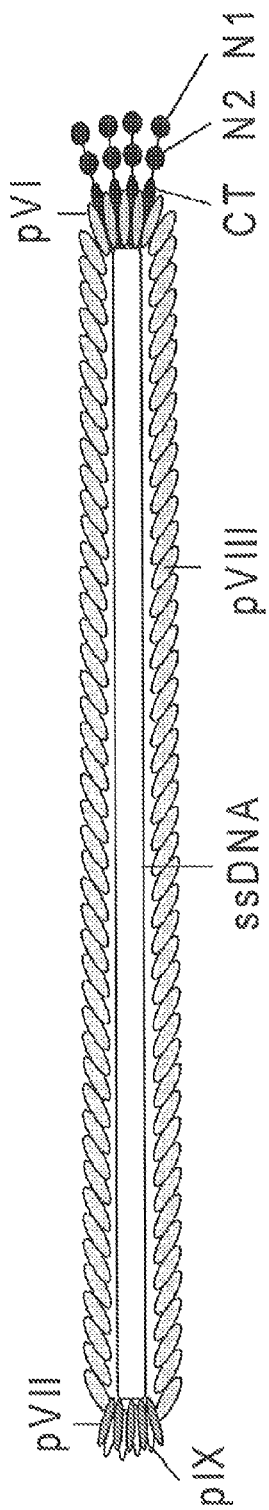
FIG. 1.

Schematic drawing of the filamentous phage structure. The virion is built up by five structural proteins that coat a single-stranded DNA molecule. In the wild type (wt) phage there are about 2700 copies of pVIII and approximately 3-5 copies of either of the four proteins pIII, pVI, pVII and pIX, which are found at each tip of the virion. Virion size is dependent on the genome size at approx. 2.3 nucleotides per pVIII coat protein and thus the length of the particle is accommodated by an increase or decrease in the inserted copies of pVIII. Notably, the pIII and pVIII structures have been characterized by x-ray fiber diffraction, crystallography and NMR. The minor coat protein pIII contains three distinct domains separated by glycin-rich regions: N1 (binds to TolA), N2 (binds to the F pilus) and CT (integrated into the virion and is important for normal virion assembly).

FIG. 2.

*E. coli* K12 codon optimisation of AviTag™, HIS6-tag and FLAG-tag. (A)

Comparison of the commercially available AviTag™ DNA sequence with the *E. coli* K12 codon usage. Light shaded columns are the submitted sequence and black columns are the reference set. (B) Upper line shows the original AviTag™, whereas the lower line shows the modified sequence adjusted according to the result in A. GGTCTGAACGACATCTTC-GAGGCTCAGAAAATCGAATGGCACGAA (SEQ ID NO. 34), GGCCTGAACGATATCTTTGAAGCCCA-GAAAATTGAATGGCATGAA (SEQ ID NO. 35), and GLNDIFEAQKIEWHE (SEQ ID NO. 36) (C) codon optimised FLAG peptide. GACTACAAGGACGATGACGA-CAAG (SEQ ID NO. 37) and DYKDDDDK (SEQ ID NO. 38) (D) codon optimised HIS6 peptide. CATCACCATCAC-CATCAC (SEQ ID NO. 39) and HHHHHH (SEQ ID NO. 40).

FIG. 3.

Titer of modified helperphages compared to wt helperphage.

FIG. 4.

ELISA analysis M13K07 AviTag-pVII

Normalised phage preparations were mixed with Streptavidin (SA) beads to absorb biotinylated virions and ELISA was performed as described in example 1.

FIG. 5.

ELISA analysis showing the accessibility of the FLAG-tag as a pVII fusion in M13K07. Normalised phage preparations were used in the ELISA assay. There is a specific FLAG-tag detection only of the M13K07-FLAG both for the M2 and M5 MAb. There is a stronger detection of the FLAG-tag by the M5 MAb.

FIG. 6

Analysis showing the accessibility of HIS-tag as a pVII fusion to both M13K07 (SEQ ID NO: 31) and VCSM13 (SEQ ID NO: 32). Normalised phage preparations were mixed with Talon Dynabeads to absorb HIS6-tagged virions and ELISA was performed as described in example 1.

FIG. 7

(A) Phagemid titers of scTcR and scFv-pIII displayed phagemids shown as $cfu^{ampR}$/ml. (B). Phagemid to helper phage ratios shown as the ratio of the phagemid titer ($cfu^{ampR}$/ml) divided by helper phage titer ($cfu^{kanR}$/ml).

FIG. 8

ELISA analysis of scTCR phagemid AviTag showing specific accessibility of AviTag after phage rescue by streptavidin coated dynabeads. Inset show signal value of M13K07-AviTag helperphage. Normalised phage preparations were used.

FIG. 9

ELISA analysis showing the accessibility of the FLAG-tag as a pVII fusion in two different phagemids, pFKPDNscTCR Vαβ4B2A1 (A) and pSEX-scFv anti-phOx (B) by capturing of phagemid virions by two anti FLAG antibodies, M2 and M5. Normalised phage preaparations were used.

FIG. 10

ELISA analysis showing functionality of scTCRpIII (A) and scFvpIII (B) displayed on phagemid-derived virions with pVIIAviTag. Normalised phage preparations were used.

FIG. 11

Analysis showing functionality of scTCR (A) and scFv (B) displayed on phagemid-derived virions with FLAG-tag and HIS6-tag. Normalised phage preparations were used.

FIG. 12

Titre of genomic phage fUSE5-scTCRpIII with and without pVIIAviTag.

FIG. 13

ELISA analysis showing the functionality of genomic fUSE5-AviTag phage preparations by capturing phages by streptavidin beads followed by detection of bound phages by anti M13-Antibodies. Normalised phage preparations were used.

FIG. 14

ELISA analysis showing the functionality of pIII-displayed scTCR on genomic phage fUSE5 with Avitag-pVII. Normalised phage preparations were used.

FIG. 15

Schematic drawing of the novel pGALD7 (A) and pGALD7ΔL (B) pVII display phagemids. The vector backbone of both phagemids was based on the pSEX81 (SEQ ID NO:29), which sequence can be accessed from GenBank accession no.: Y14584, and details on the constructed are described in Material and Methods. Both phagemids can accommodate cassettes of in frame exogenous sequences (termed $E_1$ and $E_2$) through easy cassette exchange of the NcoI/HindIII and MluI/NotI portions respectively. The cassettes are connected by a synthetic linker sequence that vary among the different constructs described herein. Abbreviations: lacPO, lac promoter; sd, Shine-Dalgarno sequence; pelB, signal sequence of bacterial pectate lyase; TP, trypsine protease site; t, T7 transcriptional terminator.

FIG. 16

Phagemid titers of scFv anti-phOx (SEQ ID NO:26) displayed from pGALD7ΔL (pVII$^{ΔL}$), pGALD7 (pVII), pSEX81 (pIII) and pSEX81ΔL (pIII$^{ΔL}$). All the phagemids harbour an ampicillin resistance marker, hence the titers are shown as ampicillin resistant colony forming units per milliliter solution (cfu$^{ampR}$/ml).

FIG. 17

Antigen specific (phOx-BSA) ELISA comparing functional scFv anti-phOx (SEQ ID NO:26) display between pVII and pIII, and with and without signal sequence (ΔL). The ELISA was conducted as described in materials and methods and the titer input was $2\times10^{10}$ cfu$^{ampR}$/ml for all samples, except for the pGALD7 (pVII), which was used undiluted (corresponding to $1.1\times10^7$ cfu$^{ampR}$/ml). The anti-M13$^{HRP}$ is a negative control on unspecific adsorbsion of the virion detection MAb to the antigen and block.

FIG. 18

(A) Phagemid titers of scFv anti-phOx displayed from pGALD7ΔL (pVII$^{ΔL}$), pGALD7 (pVII), pSEX81 (pIII) and pSEX81ΔL (pIII$^{ΔL}$) shown as cfu$^{ampR}$/ml. (B). Phagemid to helper phage ratios shown as the ratio of the phagemid titer (cfu$^{ampR}$/ml) divided by helper phage titer (cfu$^{kanR}$/ml). The virion packaging was done as standard phagemid rescue as described in materials and methods (−), or with a final concentration of 0.1 mM IPTG present after super infection in both A and B.

FIG. 19

Antigen specific (phOx-BSA) ELISA comparing functional scFv anti-phOx pVII display with and without signal sequence (ΔL) and with and without IPTG induction (0.1 mM) of the pVII fusion expression. The ELISA was conducted as described in materials and methods and the titer input was $2\times10^{10}$ cfu$^{ampR}$/ml for pGALD7ΔL (pVIIΔL), whereas the pGALD7 (pVII) was used undiluted (corresponding to $2.0\times10^9$ and $1.1\times10^7$ cfu$^{ampR}$/ml without and with IPTG, respectively). The anti-M13$^{HRP}$ is a negative control on unspecific adsorbsion of the virion detection MAb to the antigen and block.

FIG. 20

Antigen specific ELISA comparing functional scTCR (A) and scFv-anti-NIP (B) pVII display with and without signal sequence (ΔL). The ELISA was conducted as described in materials and methods using equal volumes on undiluted cleared supernatant. The anti-M13$^{HRP}$ is a negative control on unspecific adsorbsion of the virion detection MAb to the antigen and block. In (A), the GB113 antibody clone-specific for the 4B2A1 T cell receptor (Bogen et al, PMID: 1700755) was used as surrogate antigen substituting for the cognate I-E$^d$/λ2$^{315}$ ligand to the scTCR Vαβ4B2A1 (Løset et al, PMID: 17925331).

FIG. 21

(A) Phagemid titers of the scTCR Vαβ4B2A1 and the scFv anti-NIP (SEQ ID NO: 27) displayed from pGALD7ΔL and pGALD7 using standard phagemid rescue as described in material and methods. (B) Phagemid-to-helper phage ratios of the same samples as in (A).

FIG. 22

(A) Cell density of the respective E. coli cultures at the end of the virion packaging protocol measure as optical density (OD) at A$_{600nm}$. Notably, all cultures were initiated an identical density of A$_{600nm}$ 0.025 and super infected with M13K07 at MOI5 when A$_{600nm}$ 0.1 was reached. Packaging was then allowed to proceed ON at 30° C. before end culture OD was measured.

DETAILED DESCRIPTION OF THE INVENTION

It should be noted that embodiments and features described in the context of one of the aspects of the present invention also apply to the other aspects of the invention.

All patent and non-patent references cited in the present application, are hereby incorporated by reference in their entirety.

We here present a novel concept, in which the structural coat protein pVII of the filamentous phage virion is genetically altered such that the modified version encodes an N-terminal sequence tag. Depending on which type of tag that is fused to pVII, the virions are given the property of specific tag detection, as well as flexible purification and immobilization avenues as an inherent property of the system. The approach is directly compatible with all existing pIII and pVIII display systems whether phage genome-based of phagemid vectors are applied, including new library generation on pVII. Our concept therefore offers an unprecedented expansion of the already high versatility of phage display technology.

The current report shows for the first time that the filamentous phage genome tolerates an N-terminal peptide modification, not harbouring a signal sequence, of pVII without interfering with viability and functionality of the phage. This was true for both the M13K07 (SEQ ID NO: 31), VCSM13 (SEQ ID NO: 32) and fUSE5 (SEQ ID NO: 30) genomes as well as phagemids and as the sequence and phenotypic conservation between the various phage strains are very high, This most likely applies to all filamentous phages.

One of the pVII fusions chosen was a prokaryotic codon optimized version of the AviTag, a peptide which is the most efficient BirA substrate reported to date. By combining this pVII peptide display with pIII display we show that bispecific virions are produced. This was true for the phage-genome based vector fUSE5 (SEQ ID NO: 30) and from phagemid-based display when rescued with a modified M13K07 helper phage. It is easily conceivable that this bispecific nature can be used in combination with pVIII display as well. Particularly in the case of the phagemid-derived virions, the endogenous biotinylation level was very low.

However, if high biotinylation levels are desirable, this can easily be achieved by in vitro biotinylation of these virion, as well as by the use of in vivo biotinylation through the use of the novel F-positive E. coli AVB100FmkII strain.

Hence, the current concept allows for the combination of avidin-biotin technology (and other capture systems) with both dominating phage display platforms (phage and phagemid) and display systems (pIII and pVIII). It allows a controlled, site-specific attachment of the biotin moiety to the phage particle without interfering with the pIII and/or pVIII fusion, hence ensuring preserved functionality. The system is directly compatible with existing platforms without further modifications, only rendering the choice of use or not.

In conclusion, both genome-derived and phagemid-derived virions can tolerate the pVII modification, yielding virions with seemingly normal functionality and viability.

pVII Fusion Protein

In one aspect, the present invention provides a pVII fusion protein originating from a filamentous phage, said fusion protein comprising a fusion of an exogenous peptide to the N-terminus of pVII. Such a fusion protein is useful e.g. in the context of phage display.

When referring to an exogenous peptide, what is meant is a peptide not originally part of pIII, pVII or pVIII protein with or without any linker amino acids to the N-terminal end of the pIII, pVII or pVIII amino acid part of the fusion protein. In a preferred embodiment, the fusion protein does not comprise an N-terminal signal sequence. As used herein, the term peptide encompasses both short peptides, polypeptides, proteins and fragments thereof.

The term pIII protein refers to the amino acid sequence disclosed in SEQ ID NO 2. In one embodiment the pIII protein comprises the amino acid sequence with a sequence identity of at least 80% to that of SEQ ID NO 2, such as 80% identity, 81% identity, 82% identity, 83% identity, 84% identity, 85% identity, 86% identity, 87% identity, 88% identity, 89% identity, 90% identity, 91% identity, 92% identity, 93% identity, 94% identity, 95% identity, 96% identity, 97% identity, 98% identity, or 99% identity.

The term pVIII fusion protein refers to a pVIII protein, or fragments thereof, fused to an exogenous peptide.

The term pVIII protein refers to the amino acid sequence in SEQ ID NO 3.

In an embodiment the pVIII protein comprises the amino acid sequence with a sequence identity of at least 80% to that of SEQ ID NO 3, such as 80% identity, 81% identity, 82% identity, 83% identity, 84% identity, 85% identity, 86% identity, 87% identity, 88% identity, 89% identity, such as 90% identity, 91% identity, 92% identity, 93% identity, 94% identity, 95% identity, 96% identity, 97% identity, 98% identity, or 99% identity.

The term pVII protein refers to the amino acid sequence in SEQ ID NO 1.

In an embodiment the pVII protein comprises the amino acid with a sequence identity of at least 80% to that of SEQ ID NO 1, such as 80% identity, 81% identity, 82% identity, 83% identity, 84% identity, 85% identity, 86% identity, 87% identity, 88% identity, 89% identity, 90% identity, 91% identity, 92% identity, 93% identity, 94% identity, 95% identity, 96% identity, 97% identity, 98% identity, or 99% identity.

Sequence Identity

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

Folded Proteins

In a preferred embodiment, the term peptide refers exclusively to folded proteins such as antibody derived domains. The skilled addressee would recognise folded proteins could be antibodies or fragments thereof, covering Fv, scFv, Fab, single domains, Z domain of protein A (Affibody), Ankyrin or fragments thereof, T cell receptor or fragment thereof, MHC class I and II, Fibronectin or fragment thereof, Avimers, Anticalins, PDZ-domains, IgNAR or fragment thereof, CTLA4 or fragment thereof, ImmE7, Knottins, GFP and other gene-encoded biological fluorophores.

In principle, one can make a library of anything as long as it is displayed, hence at the highest level one can only separate between something that has only a non-structured configuration, as compared to a ordered structure, that is a fold.

In another preferred embodiment, the term peptide refers exclusively to short peptides between 2 to 50 aa. At some length a short random coil peptide will be long enough to adopt a defined secondary or tertiary fold and hence enter the folded domain definition. Obviously this will depend on chemical composition, hence one peptide of 20 aa will still be random coil, whereas another 20 aa peptide could be folded and hence fall into the folded domain definition.

In another preferred embodiment, the pVII fusion protein of the invention comprises a sequence selected from the group consisting of pos. 1-33, 2-33, 3-33, 4-33 and 5-33 of SEQ ID NO:1.

SEQ ID NO:1 (MEQVADFDTIYQAMIQISVVLCFAL-GIIAGGQR) is the amino acid sequence of structural coat protein pVII of the filamentous phage (wild type pVII). Most preferably, the pVII fusion protein comprises positions 1-33 of SEQ ID NO:1.

Signal Sequence

Preferably, the exogenous peptide is fused directly with or without any linker amino acids to the N-terminal end of the pVII sequence of the fusion protein. In yet another preferred embodiment, the pVII fusion protein does not comprise an N-terminal leader sequence.

The term "leader sequence" is used interchangeably with the terms "signal peptide" and "signal sequence", and refers to an amino acid sequence that targets the protein (of which the leader sequence is part) to the periplasmatic membranespace of gram negative bacteria. Examples of leader sequences often used are pelBss, OmpAss, TorAss, malEss, phoAss, lamBss, Blass, and DspAss, mglBss, sfmCss, tolBss and TorTss. Such signal sequences are known to target the complete protein to the secretory machinery of E. coli which is known to include at least SRP-dependent, SEC-dependent, TatABC-dependent or YidC-dependent translocation from the cytosol to the periplasmic space (Baneyx et al. PMID: 15529165). Hence, the term N-terminal signal sequence refers to a signal sequence that is in the N-terminal part of the protein.

Signal sequences harbouring the property of targeting a protein (of which it is part) to the secretory machinery of E. coli and thereby translocate it from the cytosolic to the periplasmic compartment can be partly identified through signatures, or motifs, defined by the chemical property of their amino acid composition.

The variety of functional signal sequence existing is as of yet, however, exceeding the current knowledge in identifying them, hence current state of the art in defining a peptide as a cognate signal sequences are typically done through data mining using knowledge based data based as template by e.g. neural network or heuristic methodology. There are several such tools available to the community through open access channels as of today, such as SignalP, PPSEARCH of PROSITE (EMBL-EBI), SecretomeP, TatP.

The challenge is even higher with the class of secretory proteins, in the sense that they are exported from the cytosolic compartment, that deviate from the rules such that no signal sequence motif can be identified, but through data mining one can also here define signal sequence features or get the probability of the secretory capacity of the eukaryotic protein in question. As of yet, no such tool exist for the prokaryotic taxa.

The only method currently available that irrevocably identified a peptide as a signal sequence is therefore by experimental means to validate the property of a peptide to establish whether or not it is a real signal sequence. It is also clear that engineering may be performed in such peptides such that the given amino acid positions in the signal sequence may be altered, yet retain its function as a signal peptide, either by native functionality, or by altered functionality, such as increased transport capacity. Also deletion or addition of amino acids may be employed. Such analysis and engineering have indeed been done with the Ff pVIII signal sequence, g8 pss targeting the Sec-pathway, and the TorAss targeting the Tat-pathway. Especially the results of Shen et al may serve as well-founded guide lines for engineering of functional, but altered mutants, of the pIII signal sequence and the bacterial pectate lyase signal sequence.

The functionality of a signal sequence may be further broken down into the two following properties:

1. Targeting a protein (of which it is part) to the secretory machinery of E. coli and thereby translocate it from the cytosolic to the periplasmic compartment and in the course of this process, being proteolytically separated from the remaining protein by specific proteases, such as Lipoprotein signal peptidase, or leader peptidases.
2. Targeting a protein (of which it is part) to the secretory machinery of E. coli and thereby translocate it from the cytosolic to the periplasmic compartment and after translocation still remain as a part of the protein.

Though the vast majority of signal sequences map to situation 1) given above, it is clear that these proteins may be easily engineered into situation 2). Therefore, any currently known signal sequences e.g. a mutant pelBss and other that originally belong to the situation 1), but are altered into situation 2), are still regarded as cognate signal sequences.

Moreover, it is conceivable to either alter a signal sequence of situation 1) into situation 2), or directly choose a signal sequence that map to situation 2) and then after translocation remove the signal sequence. This can be done either by endogenous proteases of the host and/or in the case of e.g. phage display, when the protein is fused to a capsid protein. One would then engineer into the proper region of the signal sequence, or the protein of which it is a part, an artificial protease site, such that a defined cleavage can be performed. On can here envision two different types of protease sites chosen:

A. The protease site does not cleave the protein of interest, only the predicted site, such as e.g. carboxypeptidase A, or 3C rhinovirus protease site in combination with antibodies or other scaffolds of interest, such as major histocompatibility complex molecules or T cell receptors. By using this approach one can envision e.g. phage display of the protein of interest by use of a signal sequence mapping to the situation 2) above and before used in selection etc, artificially remove the signal peptide to obtain functionality and homogeneity to the capsid fusion.
B. The protease site cleaves the protein of interest in addition to the engineered site, such as e.g. trypsin.

Both situations will still be regarded as signal sequence-dependent phage display.

Wild Type Complementation

Hitherto, it was believed that pVII fusions without signal sequence were non-functional with respect to sustaining production of phage particles (Endeman et al, 1995; Gao et al, 1999). Therefore, pVII fusion proteins with an exogenous peptide fused directly to its N-terminus had to be complemented by wt pVII protein either from a second gene on the phage genome or by donation from a helper phage.

The term wild type, sometimes written wildtype, wild-type or wt, is the typical form of an organism, strain, gene, or characteristic as it occurs in nature. Wild type refers to the most common phenotype in the natural population. Wild type also refers to the allele at each locus required to produce the wild-type phenotype. Wild type is the standard of reference for the genotype and phenotype. In biology it relates specifically to the difference between a naturally occurring organism, and one that has been deliberately mutated. Site-directed mutagenesis is a research technique that allows for the mutation of specific nucleotides in the gene sequence of a wildtype gene. Wildtype proteins are written as wt-(name of protein) e.g. a wildtype pVII protein is written wt pVII, wt-pVII or wildtype pVII.

The present inventors have discovered that such pVII fusion proteins are indeed functional and need not necessarily be complemented by wt pVII protein.

Thus, one aspect of the invention relates to pVII fusion proteins that are functional in a phage display without complementation by wt pVII protein.

Kwasnikowski et al. reported pVII fusion proteins that did not have to be complemented by wild type pVII protein. However, the pVII fusion proteins of Kwasnikowski et al., comprised a signal peptide at the N-terminal end of the exogenous peptide. Said signal peptide was assumed to be necessary to direct the N-terminal pVII fusion protein into the periplasmic space and prevent its accumulation in the cytoplasm.

The absence of a signal peptide at the N-terminal end of the pVII fusion protein has various advantages. Signal peptides are normally proteolytically removed and this processing is often not complete which generates different N-terminal ends of the processed protein when a collection of proteins are expressed, thus introducing a random heterogeneity in the system, that may affect functionality of the proteins still harbouring the leader peptide leading to unwanted errors in the processed protein. This is prevented when no signal peptide is present.

Moreover, when a library of peptides are displayed, some of the peptides may prevent or affect proteolysis, which in turn will affect activity of the displayed protein and thus functional library diversity. Yet another surprising advantage of not including a signal peptide is that viability and functionality of the phage is not affected, as opposed to when using a signal peptide. Kwasnikowski et al., reported a reduced titer for phages with the pVII fusion protein comprising a leader sequence (signal peptide) at the N termini.

Exogenous Peptide

In one embodiment, the exogenous peptide is an affinity tag that binds to a predetermined target. The affinity tag may e.g. bind to a predetermined antibody. Pairs of affinity tags and predetermined targets are well-known to the skilled person.

Protein tags are peptide sequences genetically grafted onto a recombinant protein. Often these tags are removable by chemical agents or by enzymatic means, such as proteolysis or intein splicing. Tags are attached to proteins for various purposes.

Affinity tags are appended to proteins so that they can be purified from their crude biological source using an affinity technique.

A feature of using an unprocessed N-terminal FLAG tag is that it has its formyl-Met residue intact and hence allows for the Ca2+ dependent interaction with the anti-FLAG MAb M1. The virion can thus be bound (that is immobilized) on M1 and liberated merely be chelating the cation by e.g EDTA, hence offering a very mild elution no extreme pH that denatures the heterologous fusion(s). By using the M1 this also means that the system can be used with other FLAG fusions present (internal, processed N-terminal, or C-terminal) without interference as these are not recognized by M1, or by simply keeping the [Ca2+] low.

In a preferred embodiment, the exogenous peptide of the pVII fusion protein is selected from the group consisting of Avitag (SEQ ID NO:4), FLAG tag (SEQ ID NO:9), HIS tag (SEQ ID NO:12), HAT tag, HA tag, c-Myc tag, Strep tag, V5 tag, antibody or fragment thereof, T cell receptor or fragment thereof, MHC class I and II, Ankyrin, IgNAR or fragment thereof, fibronectin or fragment thereof, Z domain of protein A, CTLA4 or fragment thereof, ImmE7, GFP and other gene-encoded biological fluorophores.

SEQ ID NO:2 (MSGLNDIFEAQKIEWHE) is a substrate sequence of the *E. coli* enzyme BirA sequence that enables enzyme mediated site-specific coupling of a biotin moiety to the substrate sequence. Thus, the assets of phage display technology and avidin-biotin technology are combined. Any fusion library in which the library is not displayed on pVII may e.g. first be fractionated against a target for identification of high-affinity library members and then immobilized using biotin binding to avidin, or an avidin-like matrix by means of also including the pVII fusion on the virions. Alternatively, any fusion library in which the library is not on pVII may e.g. first be immobilized, either randomly or in a predefined array on an avidin or avidin-like matrix, in a controlled, directional manner followed by target screening such as in e.g. SEREX, by means of also including the pVII fusion on the virions. Similarly, any member of such a pIII or a pVIII fusion library may be detected, either in bulk or as single clones, before or after target interaction by use of any avidin- or avidin-like-reporter complex the term reporter herein describes e.g. enzyme, nucleic acid species or synthetic or biological fluorophore.

Essentially the same rational as outlined for the AviTag, but whereas the latter results in a close to irreversible immobilization, the HIS6 allows for mild elution using imidazole. The HIS tag is compatible with all available IMAC matrixes, In another preferred embodiment, the exogenous peptide of the pVII fusion protein is a library member. A library as used in the present context refers to a collection of different peptides. The peptides may be folded domains or short peptides of e.g. 2-50 amino acids. Such libraries are of interest because they can be used to identify new ligands binding to a given target. There are several advantages of using pVII for displaying a library as compared to libraries displayed using pIII or pVIII. pVII display contain the same assets as pIII display with respect to directionality and valence, but will not affect infectivity, a phenomenon known to occur with pIII display, which introduced uncontrolled and unwanted heterogeneity into the system upon e.g. rescue after affinity selection. Moreover, pVII display may be achieved without the need of an N-terminal leader peptide, which are prerequisites for both pIII and pVIII display. Finally, any target immobilised species in pIII display normally requires disruption (normally by competitive, or high or low pH elution) of this target-phage bond. This is e.g. known to severely hamper retrieval of high-affinity, or stable binders in pIII display. As pIII required for infection is unaltered and readily available for alternative interactions in pVII display even after phage-target interaction, this completely eliminates the need for bond disruption, e.g. acidic elution, as immobilised phages retain full infectivity and hence may be retrieved simply by infection whilst bound to target.

Nucleic Acid

A second aspect of the invention is a nucleic acid encoding the fusion protein of the invention. The nucleic acid may be comprised within a phage genome or within a phagemid.

The term nucleic acid refers to a macromolecule composed of chains of monomeric nucleotides. In biochemistry these molecules carry genetic information or form structures within cells. The most common nucleic acids are deoxyribonucleic acid (DNA) and ribonucleic acid (RNA). In addition, the term nucleic acids include artificial nucleic acids such as peptide nucleic acid (PNA), Morpholino and locked nucleic acid (LNA), as well as glycol nucleic acid (GNA) and threose nucleic acid (TNA). Each of these is distinguished from naturally-occurring DNA or RNA by changes to the backbone of the molecule.

A phagemid or phasmid is a type of cloning vector developed as a hybrid of the filamentous phage Ff and plasmids to produce a vector that can propagate as a plasmid, and also be packaged as single stranded DNA in viral particles. Similarly to a plasmid, a phagemid can be used to clone DNA fragments and be introduced into a bacterial host by a range of techniques (transformation, electroporation). However, infection of a bacterial host containing a phagemid with a 'helper' phage, for example VCSM13 or M13K07, provides the necessary viral components to enable single stranded DNA replication and packaging of the phagemid DNA into phage particles.

Filamentous Phage

A third aspect of the invention is a filamentous phage comprising the fusion protein of the invention. The filamentous phage may comprise a phage genome or a phagemid.

Phage, often called bacteriophage, is here meant as a virus infecting, replicating and which is secreted from bacteria. A filamentous bacteriophage, or filamentous phage, is a phage with a single stranded DNA genome (ssDNA genome) which is packaged with phage coatproteins The secreted filamentous phage particle has phenotypically a filamentous structure.

The term filamentous phage as used herein encompasses both phage genome-derived virions and phagemid-derived virions.

In one embodiment, the filamentous phage does not comprise a gene encoding the fusion protein, as the fusion protein may have been donated by a helper phage.

The term helper phage refers to a virus which helps a separate and unrelated defective virus defined as e.g. a phagemid which in itself is not a phage genome neither a functional virus, but merely a plasmid containing one or several elements derived from a phage genome, to reproduce by infecting the same host cell that is already occupied by the defective virus and providing the proteins which the defective virus is missing and needs to form complete its life cycleviri-ons containing the phagemid.

In another embodiment, the filamentous phage does comprise a nucleic acid encoding the fusion protein of the invention. The filamentous phage may comprise a phage genome or a phagemid. Particular preferred is a phage that comprises a phage genome comprising the nucleic acid encoding the fusion protein of the invention.

In yet another embodiment, the filamentous phage of the invention further comprises a gene encoding wt pVII and/or wt pVII protein. I.e. the number of fusion proteins displayed by the filamentous phage may be adjusted by modulating the ratio of wt pVII to pVII fusion protein. Such a system may also be referred to as a 77 system or 7+7 system depending on whether the wt pVII protein is donated from a helper phage (7+7) or from a second gene on the phage genome (77).

In still another embodiment, the filamentous phage does not comprise wt pVII gene and/or wt pVII protein. I.e. the filamentous phage comprises only pVII fusion protein and no wt. pVII protein.

In a preferred embodiment, the filamentous phage further comprises a pIII fusion protein or a pVIII fusion protein. A library may e.g. be displayed at pIII or pVIII and the pVII fusion protein may be used for affinity purification, immobilization or detection using e.g. avidin or an avidin-like matrix. Preferably, the filamentous phage comprises pIX protein solely in wild type form.

A fourth aspect of the invention is a library of filamentous phages of the invention, said filamentous phages displaying exogenous peptides or proteins as fusions to pIII, pVII or pVIII.

A library is a collection of filamentous phages displaying peptides or proteins as part of one or more of the filamentous phage coatproteins. Such libraries can comprise two or more phages displaying different peptides or proteins. In a preferred embodiment, peptides are displayed simultaneously at pVII and either pIII or pVIII.

In another preferred embodiment, the exogenous peptide displayed at pVII is selected from the group consisting of Avitag (SEQ ID NO:4), FLAG tag (SEQ ID NO:9), HIS tag (SEQ ID NO:12), HAT tag, HA tag, c-Myc tag, Strep tag, V5 tag, antibody or fragment thereof, T cell receptor or fragment thereof, Ankyrin, IgNAR or fragment thereof, fibronectin or fragment thereof, MHC class I and II, Z domain of protein A, CTLA4 or fragment thereof, ImmE7, GFP and other biological gene-encoded fluorophores. In this embodiment, the peptides displayed at pIII or pVIII are preferably library members. In an alternative embodiment, the library members are displayed at pVII, while pIII or pVIII displays an exogenous peptide selected from the group consisting of an Avitag (SEQ ID NO:4), FLAG tag (SEQ ID NO:9), HIS tag (SEQ ID NO:12), HAT tag, HA tag, c-Myc tag, Strep tag, V5 tag, antibody or fragment thereof, T cell receptor or fragment thereof, MHC class I and II, Ankyrin, IgNAR or fragment thereof, fibronectin or fragment thereof, Z domain of protein A, CTLA4 or fragment thereof, ImmE7, GFP and other biological gene-encoded fluorophores.

Phage Display System

A fifth aspect of the invention is a phage display system comprising a phagemid and a helper phage, wherein the helper phage comprises a nucleic acid encoding the pVII fusion protein of the invention.

Phage display system, phage display technique, phage display technology or simply phage display refers to a method for the discovery and study of protein-protein, protein-peptide, and protein-DNA interactions that utilizes bacteriophage to connect proteins with the genetic information that encodes them.

Displaying protein or displayed protein refers to a protein fused to a phage coatprotein that is accessible for detection or immobilisation by a ligand A sixth aspect of the invention is a phage display system comprising a phagemid and a helper phage, wherein the phagemid comprises a nucleic acid encoding the pVII fusion protein of the invention.

Kits

A seventh aspect of the invention is a kit comprising a phage display system composed of a phagemid and a helper phage, wherein the phagemid comprises the nucleic acid encoding the pVII fusion protein of the invention. The kit should include a phagemid with a pVII encoding gene with a multiple cloning site N-terminally in the coding region and a helper phage (e.g. M13K07, VCSM13 or other). The kit should be supplemented with protocols for infection, expression, immobilisation, selection and detection of phage clones. The kits should also be accompanied with necessary recipes for buffers and media for performing the specific assays.

A kit is here referred to a collection of reagents for generating phage particles with a single or bispecific fusion proteins either as a phage display library or as single phage particle. A kit could include phagemids, helper phages, bacterial strains and protocol with recipes for reagents and assay description. A kit can be used for the development of research, diagnostic and therapeutic reagents.

An Eighth aspect of the invention is a kit comprising a phage genome-based phage display system, wherein the phage genome comprises a nucleic acid encoding the pVII fusion protein of the invention.

The kit should include a phage genome vector (M13K07, VCSM13, fUSE5 (SEQ ID NO: 30)) with a pVII encoding gene with a multiple cloning site N-terminally in the coding region. The kit should be supplemented with protocols for infection, expression, immobilisation, selection and detection of phage clones. The kits should also be accompanied with necessary recipes for buffers and media for performing the specific assays.

A ninth aspect of the invention is a kit comprising a helper phage for production of pIII fusion phagemid libraries or single pIII fusion phagemid clones with a tag as a pVII fusion. The kit should include a Helper phage (M13K07, VCSM13) with a pVII encoding gene with inserted sequence encoding a short peptide suitable for capture and/or detection purposes. The kit should be supplemented with protocols for infection, expression, immobilisation, selection and detection of phage clones. The kits should also be accompanied with necessary recipes for buffers and media for performing the specific assays.

A tenth aspect of the invention is a kit comprising a phage genome vector for generating a phage genome library for display of fusion proteins on both pIII and pVII. Such a kit should include a phage genome vector (Ff) with genes encoding both PIII and PVII with multiple cloning sites N-terminally in each of the coding regions. Alternatively the kit should contain a phage genome vector with inserted sequence N-terminally in pVII encoding a short peptide suitable for capture and/or detection and a multiple cloning site N-terminally in pIII. The kit should be supplemented with protocols for infection, expression, immobilisation, selection and detection of phage clones. The kits should also be accompanied with necessary recipes for buffers and media for performing the specific assays.

An eleventh aspect of the invention is a method comprising the steps of
a. Providing a bispecific phage display library, wherein phages comprise a peptide displayed at a first position and an affinity-tag at a second position
b. Selecting the phage display library against a target
c. Immobilizing the phage display library against a capture group of the affinity-tag The invention will now be described in further details in the following non-limiting examples.

EXAMPLES

Example 1

Modified Helper Phages with Peptides Fused to pVII

Modified helper phages M13K07 (SEQ ID NO: 31) and VCSM13 (SEQ ID NO: 32), with FLAG-pVII, HIS6-pVII, and AviTag-pVII may show a very broad potential for expanding the use of phage display technology, but it is of crucial importance that the fusion peptides do not compromise the functionality of the helper phage, thus titration of the phages are an important verification parameter. In addition the peptides fused to pVII must be accessible for the subsequent detection and/or immobilisation. This example support the fact that both pVII-modified helper phages can harbor a variety of peptides for detection and/or immobilization purposes and that these fusion peptides do not affect the infectivity of the phages.

Whilst early results from Endemann and Model (PMID: 7616570) indicated that the filamentous phage (Ff) capsid protein pVII did not tolerate exogenous fusions, it has later been shown that both phagemid-based (Gao et al (PMID: 10339535) and phage genome-based (Kwasnikowski et al (PMID: 16277988) peptide and folded domain display may be allowed as N-terminal fusions to pVII. In both cased, it is emphasized that the key to success required periplasmic targeting of the fusion protein by adding a prokaryotic signal sequence, or leader peptide, to the extreme N-terminus of the fusion, thus targeting the fusion to the SEC pathway of the *E. coli* host.

Productive pVII display has previously only been shown in the context of N-terminal fusions encoded on a phagemid harboring a N-terminal leader peptide ensuring transport of the recombinant pVII to the periplasmic compartment (Endeman et al, 1995; Gao et al, 1999).

However, it is known that before incorporated into the virion, wt pVII is found as an integral membrane protein in the inner membrane of the gram negative *E. coli* host, having its N-terminus facing the periplasmic space. Moreover, as this membrane bound, mature wt pVII retains its amino-terminal formyl group (Simons et al, PMID; 6945579), it does not appear to be N-terminally processed by e.g. the periplasmic leader peptidases, as is the case with the vast majority of signal sequence-directed proteins found outside the cytosolic compartment (Baneyx and Mujacic, PMID: 15529165). As no apparent signal sequence-like motif can be identified in the pVII ORF, its mode of translocation from the cytosol to the periplasm remains elusive, but most likely does not involved the four major secretory machineries identified in *E. coli*, namely the SEC-, SRP- and Tat- and YidC pathways (Baneyx and Mujacic, PMID: 15529165; Samuelson et al, PMID: 10949305). The structure of filamentous phage virion is shown in FIG. 1.

Reagents

All media and buffers were prepared essentially as described in Sambrook et al (Molecular cloning: a laboratory manual (Cold Spring Harbor Laboratory Press)). The anti-M13-HRP antibody and the M2 and M5 antibodies were purchased from GE Healthcare Bio-Sciences AB (Uppsala, Sweden) and Sigma-Aldrich (Oslo, Norway), respectively. Restriction enzymes (RE) were purchased from New England Biolabs (Ipswich, Mass., USA) with the exception of DpnI, which was obtained from Stratagene (LaJolla, Calif., USA). DNA oligos were purchased from MWG Biotech AG (Ebersberg, Germany). Dynabeads MyOne™-Streptavidin magnetic beads and Talon™ Ni-NTA magnetic beades were both purchased from Invitrogen (Oslo, Norway). BSA and Tween 20 was purchased form Sigma-Aldrich (Oslo, Norway). Pfu Ultra DNA and Phusion DNA polymerases were purchased from Stratagene (LaJolla, Calif., USA) and Sigma-Aldrich (Oslo, Norway), resepectively. TMB soluble was from Chalbiochem.

Bacterial Strains, Phage

The *E. coli* strains XL1-Blue was purchased from Stratagene (LaJolla, Calif., USA). M13K07 helper phage was purchased from GE Healthcare Bio-Sciences AB (Uppsala, Sweden) whereas VCSM13 (SEQ ID NO: 32) was purchased from Stratagene (LaJolla, Calif., USA).

Design and In Vitro Mutagenesis of Avitag™-, HIS$_6$-, and Flag-pVII

Figure 2:
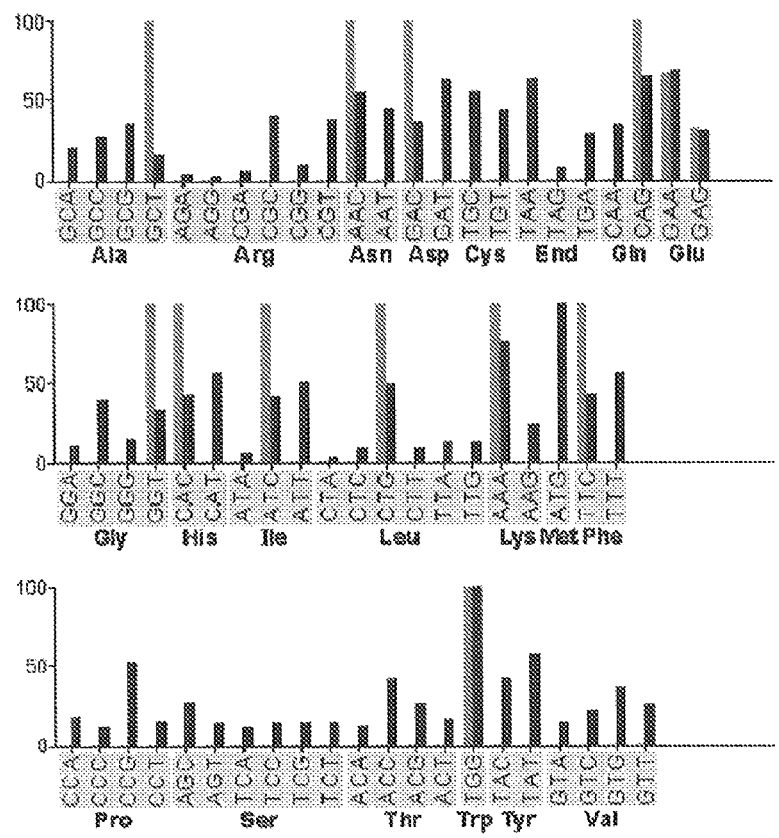

The open reading frame (ORF) of the AviTag™ (N-MS-GLNDIFEAQKIEWHE-C) was compared to the codon usage in *E. coli* K12 strains using the GCUA server (http://gcua.schoedl.de/seqoverall.html). A prokaryotic codon-optimized version of the AviTag™ peptide sequence (SEQ ID NO:4) was attached N-terminally to the pVII ORF by QuikChange™ in vitro mutagenesis according to the manufacturers' protocol (Stratagen, LaJolla, Calif., USA), using the primer pair BirA-pVII_frwd/BirA-pVII_rev (5'-CCG-GCTAAGTAACATGTCCGGCCTGAAC-GATATCTTTGAAGCGCAGAAAATTGAATGGCA TGAAATGGAGCAGGTC-'3/5'-GACCTGCTC-CATTTCATGCCATTCAATTTTCTGCGCT-TCAAAGATATCGTTCAGGCCGGAC ATGTTACT-TAGCCGG-3') (SEQ ID NO:5 and SEQ ID NO:6, respectively). In the same manner as described above, E. coli K12 codon optimized versions of the FLAG-tag (N-DYKD-DDDK-C) (SEQ ID NO:9) and the HIS$_6$-tag (N-HHHHHH-C) (SEQ ID NO:12) were attached N-terminally to the pVII ORF using the primer pairs FLAG-pVII-frwd/FLAG-pVII-rev (5'-CCGGCTAAGTAACATGGACTACAAAGAT-GACGATGACAAAATGGAGCAGGTCG-3'/5'-CGACCT-GCTCCATTTTGTCATCGTCATCTTTGTAGTCCATGT-TACTTAGCCGG-3') (SEQ ID NO:7 and SEQ ID NO:8, respectively) and HIS6-pVII-frwd/HIS6-pVII-rev (5'-CCG-GCTAAGTAACATGCATCACCATCACCAT-CACATGGAGCAGGTCG-3'/5'-CGACCTGCTCCATGT-GATGGTGATGGTGATGCATGTTACTTAGCCGG-3') (SEQ ID NO:10 and SEQ ID NO:11, respectively), respectively. The various constructs were verified by DNA sequencing (in-house ABI lab DNA sequencing core facility, Dept. Molecular Biosciences, University of Oslo) in all cases. To ensure a clean vector background, a BsrGI/SnaBI RE fragment containing the modified pVII was moved into either the M13K07 wt or VCSM13 wt genome on compatible RE sites using standard techniques. The DNA constructs were introduced into the various E. coli hosts by electroporation. Primer design was based on a sequence alignment of the M13K07 (New England Biolabs sequence) (SEQ ID NO:31) and VCSM13 (GenBank accession no.: AY598820) (SEQ ID NO:32) sequences using ClustalW. The sequence of the modified AviTag™-, HIS$_6$-, and FLAG-sequences are shown in FIG. 2.

Preparation of Phage Particles

Phages were amplified from E. coli XL1-Blue transformed with the M13K07 (SEQ ID NO: 31), VCSM13 (SEQ ID NO: 32) constructs essentially as described (Scott and Smith, PMID: 1696028).

SA Bead-Capture of Biotinylated Virions

10 μl/Tube™-Streptavidin beads were transferred to fresh 1.5-ml tubes and 500 μl 2% BSA in PBS (w/v) was added. Likewise, 250 μl of cleared supernatant or the appropriate amount of phages were transferred to 1.5-ml tubes and supplemented with 250 μl of 2% BSA. The tubes were then incubated for 1 h at room temperature (RT) on a rotating wheel. Thereafter, the beads were washed 3× by first immobilizing the beads by using a Dynal tube magnet rack. The supernatant was discarded and 0.5 ml of PBS containing 0.05% Tween 20 (PBST) added to each tube. The tubes were taken out of the rack and briefly vortexed before re-entered into the rack. The supernatant was again cleared and the washing repeated twice. The tubes were removed from the rack and 250 μl of blocked phage and 250 μl PBST were added to each tube. The tubes were then incubated for 1.5 h/RT on a rotating wheel. The tubes were washed 3× in PBST as described above. 0.5 ml of PBST containing anti-M13 MAb-HRP (1:2000) was then added to each tube and the tubes were incubated for 1 h/RT on a rotating wheel. The tubes were washed 3× in PBST as described above. 0.5 ml of ABTS was then added to each tube and the tubes left on the bench for 30 min, before place in the magnet rack and 100 μl supernatant transferred to Maxisorp ELISA strips (Nunc, Roskilde, Denmark). The absorbance was then measured at $A_{405nm}$ using a TECAN ELISA reader apparatus.

Phage-Capture Enzyme Linked Immunosorbent Assays (ELISAs)

M2 and M5 antibodies were absorbed to MaxiSorp™ microtiter plate wells (Nunc, Roskilde, Denmark) in concentrations from 2.5 to 5 μg/ml in PBS, pH 7.4 overnight at 4° C. The wells were blocked with 2% skim milk in PBS (w/v) for 1 h at RT, virion preparations where then added and allowed to react for 1 to 2 h at RT before captured virions were detected with anti-M13-HRP (1:5,000) for 1 h at RT. Between each step, the wells were washed 3× with PBST. The wells were developed with ABTS substrate and the absorbance read at $A_{405nm}$ after 30 min.

Results

A—Titration of Helperphages.

Figure 3:
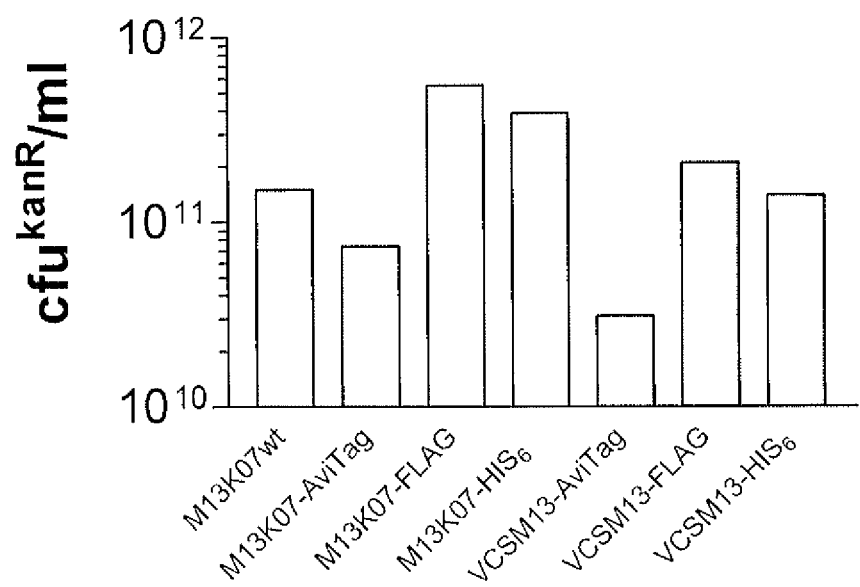

16 ml 2×YT were inoculated with a fresh XL1-Blue culture and incubated at 37° C./250-rpm to an $A_{600nm}$ 0.4-0.8. 10 μl of each diluted phage preparations were transferred to a 96-well microtiter plate. 190 μl of the XL1-Blue culture was transferred to each well with the phage diluents. The plate was incubated for 50 min/37° C. BA82/20 membrane was overlaid a LB-kan agar-dish, a volume of 3 μl/sample spotted on the membrane and the dish incubated at 37° C./ON. Colonies were counted (FIG. 3).

B—Accessibility and Functionality of the Inserted Peptides

Avitag:

The BirA enzyme is an acetyl-CoA-carboxylase and is found endogenously in all E. coli. It has indeed been shown that the introduction of AviTag in the context of phage into such cells results in a small level (~7%) of target biotinylation by endogenous BirA (Sholle et al, PMID: 16628754). To test whether or not the N-terminal pVII modification actually were functional in that virions were assembled and worked as an enzymatic substrate for BirA, we tested if the resulting virions could be captured from crude supernatant using SA-coated magnetic beads.

Figure 4:
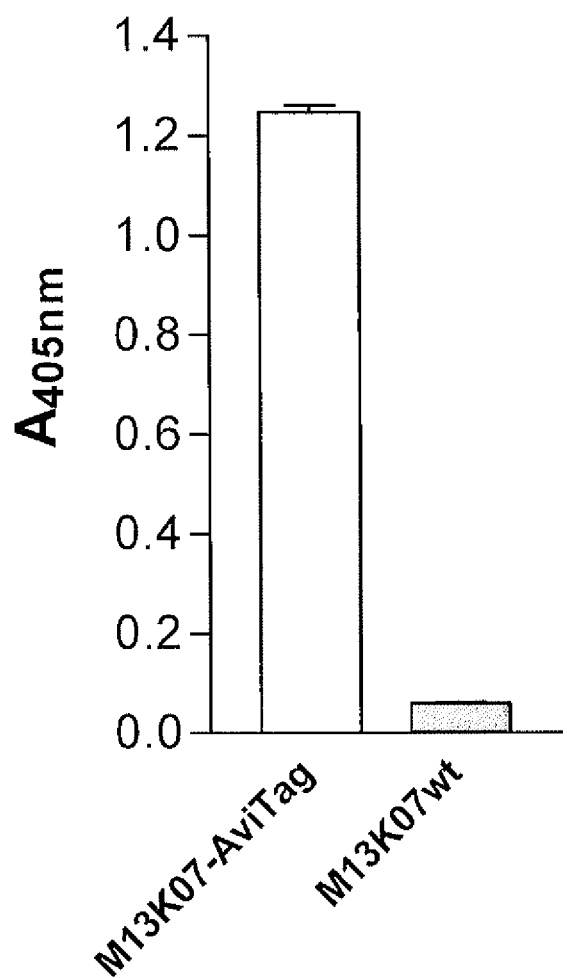

Capture of M13K07-AviTag pVII by Dynal Streptavidin beads. Two phages were employed in the assay: M13K07-AviTag which was in vivo biotinylated by the endogenous BirA- from the host and M13K07 wt. The result clearly showed a specific SA capture, whereas the M13K07 (SEQ ID NO: 31) did not bind. Thus, the AviTag-pVII fusion must indeed be functional in the sense that it both accommodate to the virion as wt pVII, whereas the N-terminal AviTag is accessible to the BirA enzyme and is recognized as a substrate for biotinlylation (FIG. 4).

FLAG-Tag

Figure 5:
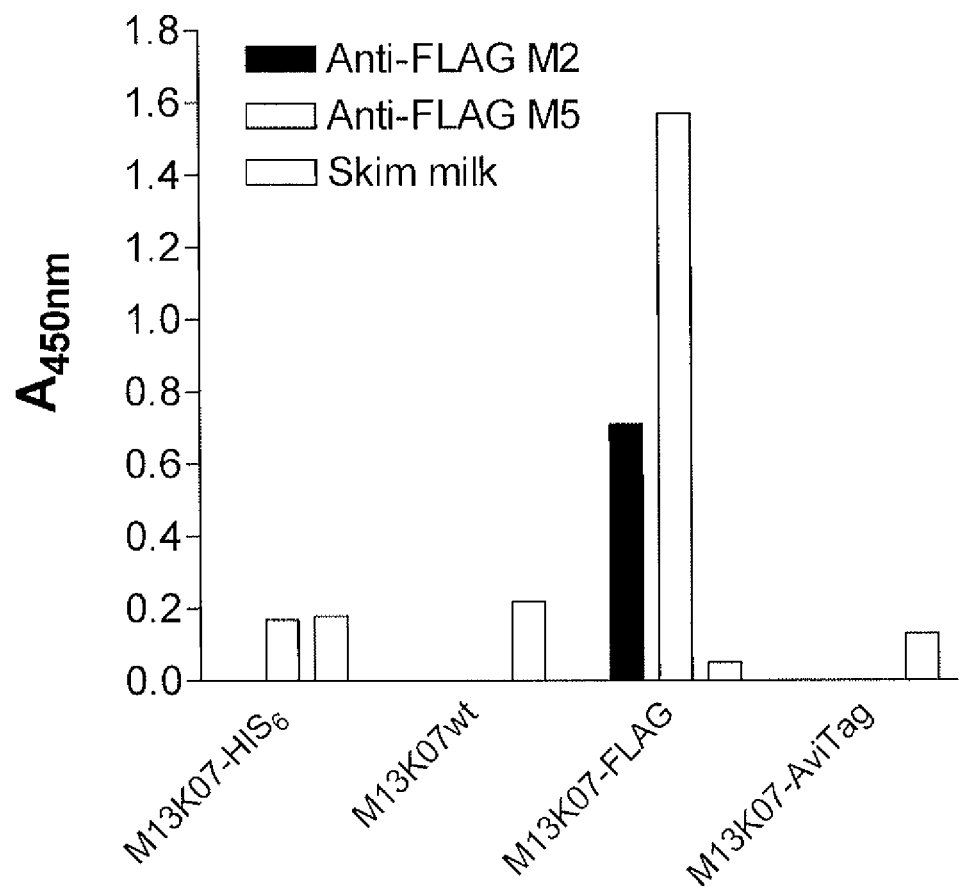

ELISA assays were performed to show the accessibility of the FLAG-tag as a pVII fusion in M13K07 (SEQ ID NO: 31) by capturing of phages by two anti FLAG antibodies, M2 and M5. In the assay wildtype M13K07, M13K07-His and M13K07-AviTag were included (FIG. 5).

His-Tag

Both M13k07-HIS6 and VCSM13-HIS6 were tested for specific binding to DynalTalon Beads (IMAC matrix).

Figure 6:
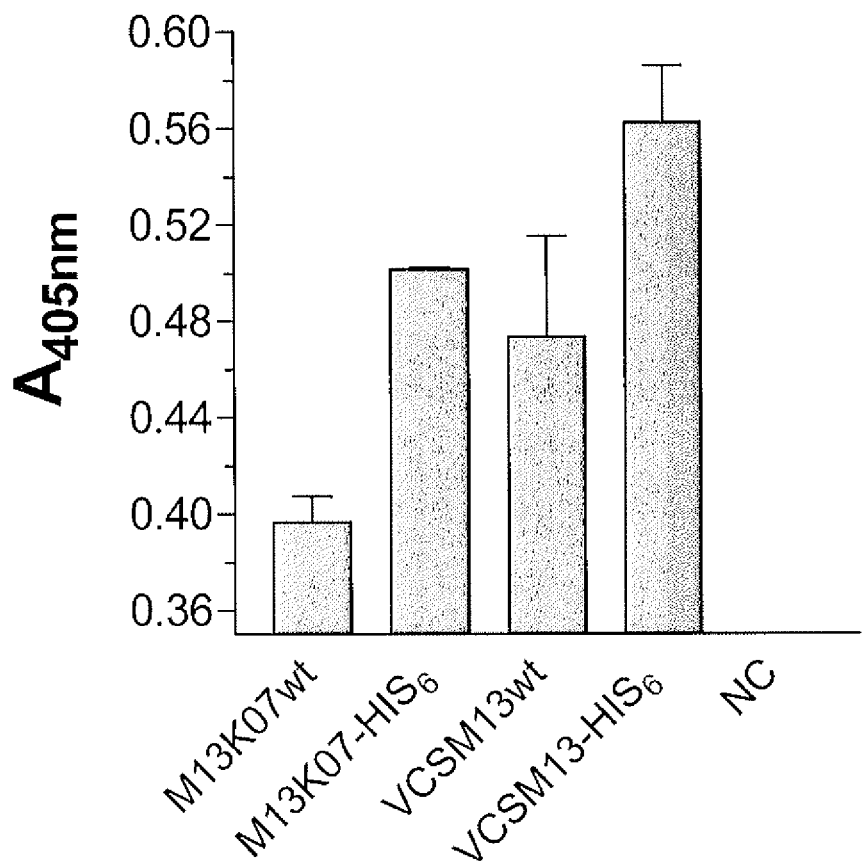

Briefly, Talon Beads were blocked by incubation with 2% BSA for 30 minutes with rotation. The beads were washed and added 250 μl of titer matched BSA-blocked phage supernatant (corresponding to $2\times10^{10}$ cfu$^{kanR}$/ml) and further incubated for 30 min/RT on a rotating wheel. After washing the beads in PBST, anti-M13 MAb-HRP (diluted 1:2000) was added to each tube and the tubes were further incubated for 45 min/RT on a rotating wheel. After washing, ABTS was added to each tube and incubated 15 min RT, before placing in the magnet rack. 100 μl volumes of each solution transferred to Maxisorp ELISA strips. The absorbance was measured at A405 nm using a TECAN ELISA reader apparatus. The result is truly indicative that the HIS$_6$-pVII containing virions are preferentially bound to Ni-NTA magnetic beads. Despite the low signals, which can be overcome by assay optimalisation, there is indeed a differential binding of the cognate virions to the Ni-NTA matrix. Of the most attractive applications of this particular pVII fusion is the possibility to exploit it for Ni-NTA purification in combinations with e.g. spin columns, as well as site-specific, and thus homogenous directional immobilization the Ni-NTA matrixes (FIG. 6).

Example 2

Functionality of Modified Helper Phages in Packaging of Phagemids

The promise of the invention is the use the modified helper phages for functional packaging of phagemids displaying a folded domain on a phage coat protein other than pVII, preferably in pIII or pVIII. The following examples support that modified helperphages with different peptides fused to pVII are able to perform functional phagemid packaging and that these phagemids display both functional pVII peptide fusion as well as functional folded domains fused to their pIII coat-proteins. In this manner the examples also serve for bispecific display using phagemids.

Reagents

All media and buffers were prepared essentially as described in Sambrook et al (Molecular cloning: a laboratory manual (Cold Spring Harbor Laboratory Press)). The anti-M13-HRP antibody and the M2 and M5 antibodies were purchased from GE Healthcare Bio-Sciences AB (Uppsala, Sweden) and Sigma-Aldrich (Oslo, Norway), respectively, whereas the F23.2 and GB113 antibodies were a kind gift from Professor B. Bogen (Institute of Immunology, University of Oslo, Norway). Dynabeads MyOne™-Streptavidin magnetic beads were purchased from Invitrogen (Oslo, Norway). BSA and Tween 20 was purchased form Sigma-Aldrich (Oslo, Norway). The hapten 2-phenyloxazol-5-one (phOx) conjugated to BSA was prepared essentially as described elsewhere (Makela et al, PMID; 722243).

Bacterial Strains, Phage and Phagemids

The E. coli strain XL1-Blue was purchased from Stratagene (LaJolla, Calif., USA). M13K07 helper phage was purchased from GE Healthcare Bio-Sciences AB (Uppsala, Sweden). The pSEX81 (SEQ ID NO:29), phagemid harbouring a scFv with specificity against 2-phenyloxazol-5-one (phOx) coupled to bovine serum albumin (BSA) were kindly provided by Affitech AS (Oslo, Norway). The pFKPDN-scTCR Vαβ4B2A1 is described in (Løset et al 2007, PMID: 17925331) (SEQ ID NO:28).

Preparation of Phage Particles

Phagemid rescue from E. coli XL1-Blue using M13K07 helper phages and virion assembly was monitored by spot titration as described (Welschof et al, PMID: 9050877 and Koch et al, PMID: 11126120).

Phage-Capture Enzyme Linked Immunosorbent Assays (ELISAs)

MAb M2, M5, F23.2, GB113, phOx-BSA were absorbed to MaxiSorp™ microtiter plate wells (Nunc, Roskilde, Denmark) in concentrations from 2.5 to 5 μg/ml in PBS, pH 7.4 overnight at 4° C. The wells were blocked with 2% skim milk, or 2% BSA in PBS (w/v) for 1 h at RT, virion preparations where then added and allowed to react for 1 to 2 h at RT before captured virions were detected with anti-M13-HRP (1:5,000), for 1 h at RT. Between each step, the wells were washed 3× with PBST. The wells were developed with ABTS substrate and the absorbance read at $A_{405nm}$ after 30 min.

Results:

A—Packaging and Titration of Phagemids by Modified M13K07.

Figure 7:
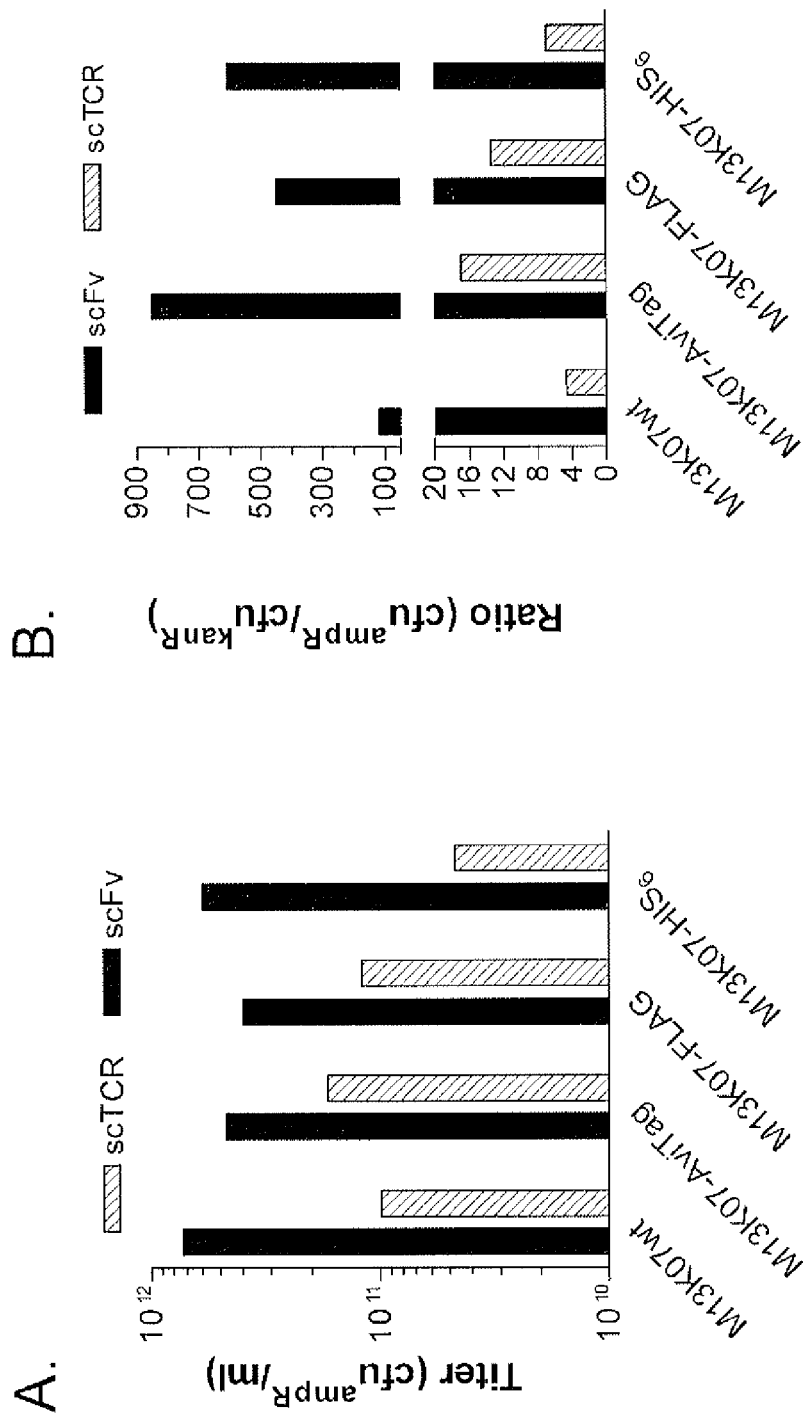

Two phagemids with different folded domains were employed, pFKPDNscTCR Vαβ4B2A1 pSEX-scFv anti-phOx, displaying a scTcR and a scFv as pIII fusion, respectively. Both were packaged with three modified and wt M13K07 helperphages. Briefly, overnight cultures of the two phagemid clones were infected with modified and wt helperphages. After incubation, the culture were centrifuged and the bacterial pellet was resuspended in YT-medium with ampicillin and kanamycine and further incubated ON at 30° C. Cleared supernatants by centrifugation were used downstream. E. coli XL-1 Blue was infected with dilutions of phages and plated on ampicillin and kanamycin plates for the titration of phagemids and helperphages, respectively. (FIG. 7)

Both packaged phagemids show high ratios, indicating successful and functional packaging by all three modified M13K07 helper phage formats.

Figure 8:
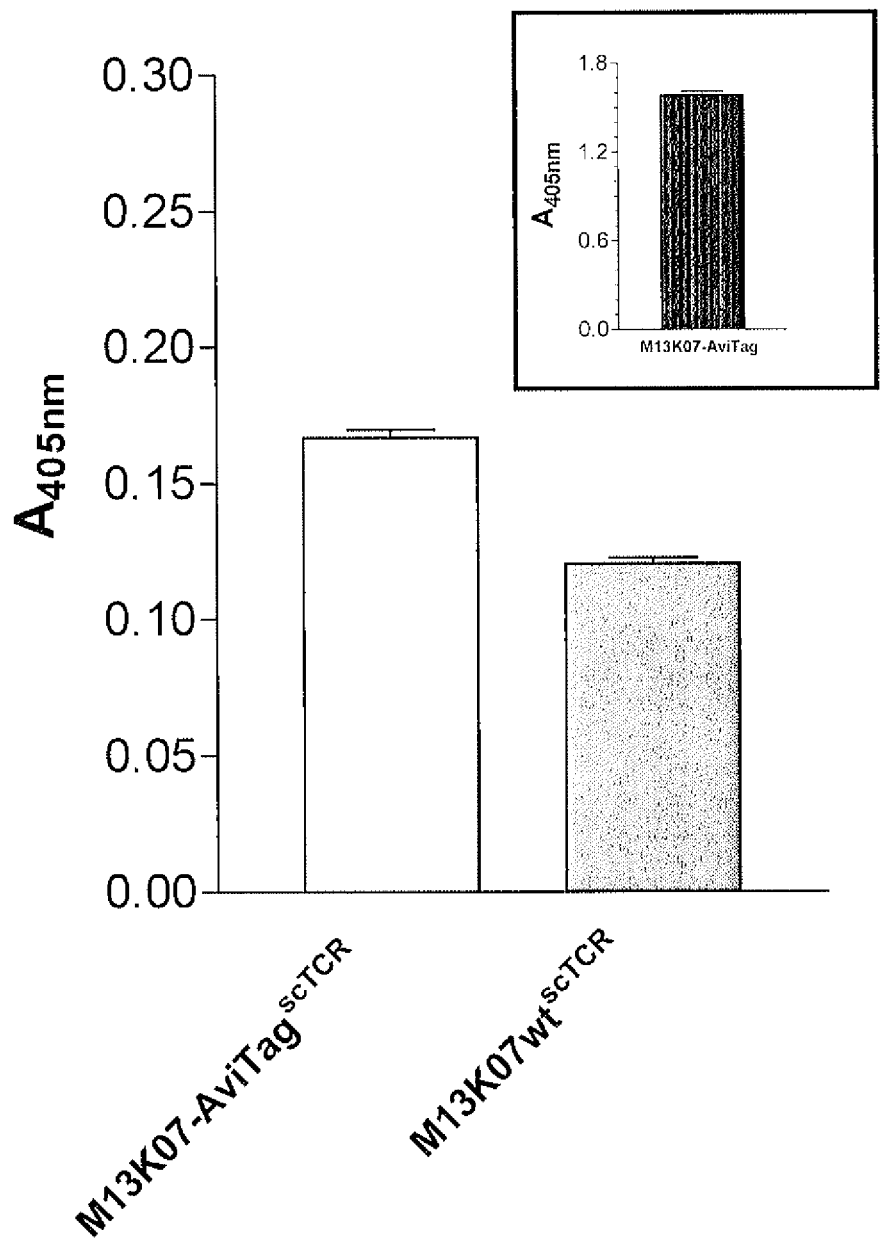
Figure 9:
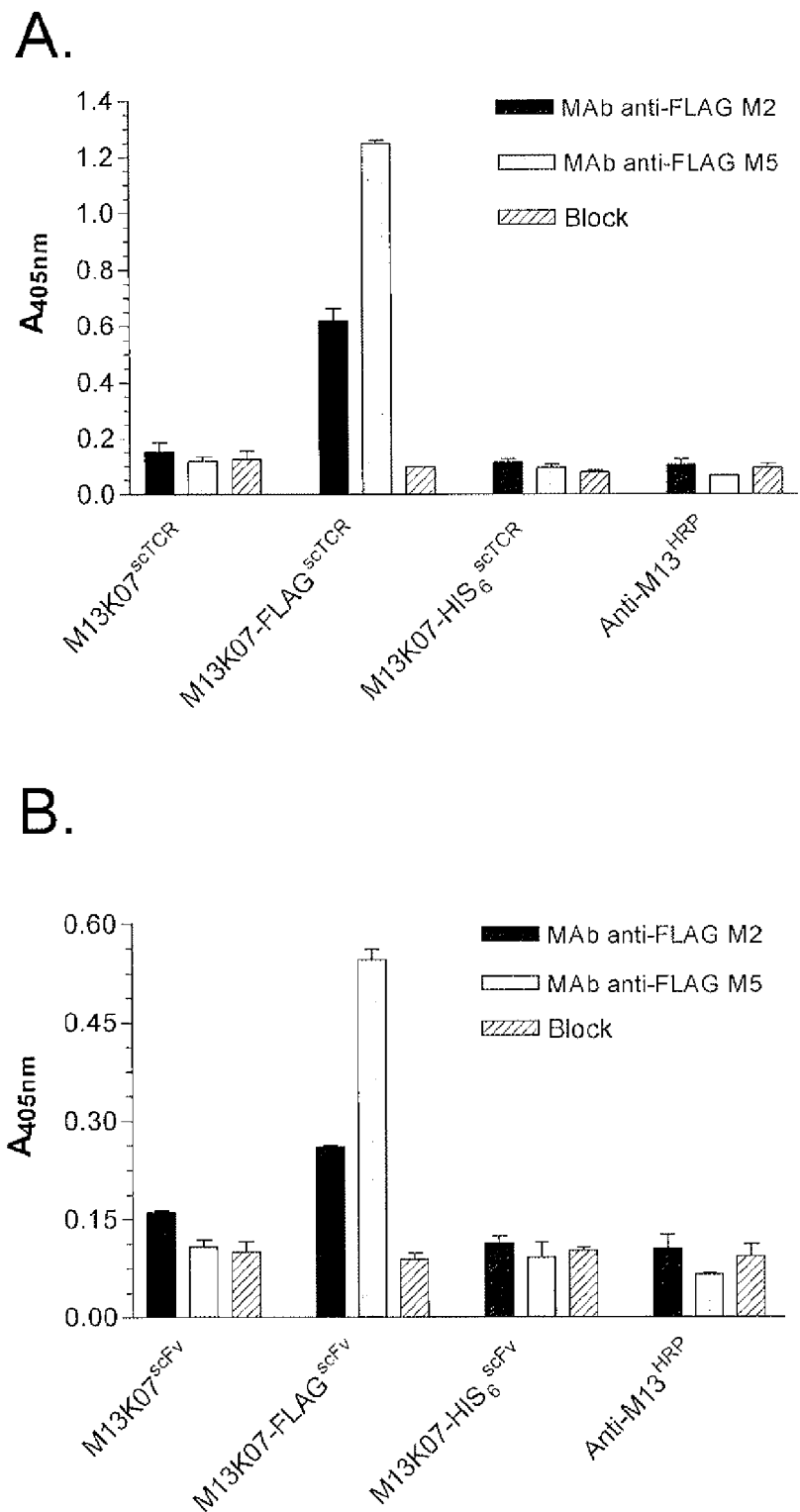

B—Functionality of pVII Donated by Helper Phage in Phagemid pIII Display:

pVII-Avitag display: With respect to AviTag-pVII functionality, SA capture on beads was conducted essentially as described in example 1. Though the signals are low, there is indeed a specific differential capture of the AviTag-pVII containing virions (FIG. 8). As compared with the positive control (insert), it is clear that the level of biotinylation lower on the phagemid virions than on the M13K07 virions when both harbour the AviTag-pVII fusion. However, it is known that endogenous AviTag biotinylation in the context of phage is only in the range of 7% at 37° C. (Scolle et al PMID: 16628754). Whereas the M13K07-AviTag indeed is packaged at 37° C., the phagemid rescue is done at only 30° C., which strongly suggests that the difference observed is due to lower endogenous BirA activity per see at the lower temperature. Hence, for future use the virion biotinylation efficiency must be increased to exploit this feature. This can conveniently be done by in vitro biotinylation of the virions, which should render close to 100% biotinylation using standard techniques (Scolle et al PMID: 16628754). Alternatively, one can do in vivo biotinylation by over-expressing the BirA enzyme. It is known that by super-transforming E. coli such that more than the phagemid or phage genome vector are in the same cell may lead to the packaging of the by standard plasmid into the virion and hence leading to loss of the genotype-phenotype linkage. This would be the case if the BirA was over-expressed from a plasmid. For single clone evaluation this may be acceptable, but when combining the approach with combinatorial repertoires this is unacceptable as it might lead to loss of phenotypic variants retrieved during panning. Alternatively, the BirA can be over-expressed from a chromosomal integration as offered by the E. coli MC1061-derived AVB100 strain (Avidity, Colo., USA). This strain is however lacking the F plasmid encoding the F pili structure indispensable for the phagemid system. AVB100 is however directly compatible with phage genome-based vectors, which do not need to be helper phage complemented. To adopt the AVB100 strain to also suit phagemid-based phage display in combination with the modified M13K07 helper phage, we therefore mated AVB100 with XL1-Blue by standard conjugation (example 5).

pvII-Flag Display:

ELISA assays were performed to show the accessibility of the FLAG-tag as a pVII fusion in two different phagemids-derived virions, pFKPDNscTCR Vαβ4B2A1 (FIG. 9A) and pSEX-scFv anti-phOx (FIG. 9B), by capturing of phagemid virions by two anti FLAG antibodies, M2 and M5. Briefly, Antibodies were coated on ELISA plates ON at 4° C. The plates were washed and phagemid preparations were incubated on the plates for 2 hours at room temperature. The plates were washed and further incubated with anti-M13 HRP conjugated antibody. The signals were developed after washing of the plates adding ABTS soluble and incubation at RT/30 min (FIG. 9).

FLAG-specific reactivity is obtained for the phagemid-derived virions packaged with the M13K07-FLAG, whereas all other samples are negative. I.e the packaged phagemid-derived virions display the FLAG tag as a functional pVII-fusion.

A. Functionality of pIII Phagemid Display.

Two different phagemid-derived virions, pFKPDNscTCR Vαβ4B2A1 and pSEX-scFv anti-phOx, both displaying Avi-Tag (FIG. 10), FLAG-tag (FIG. 11) and HIS6-tag (FIG. 11) were assayed for functional display of the scTcR and scFv pIII-fusion, respectively.

Figure 10:
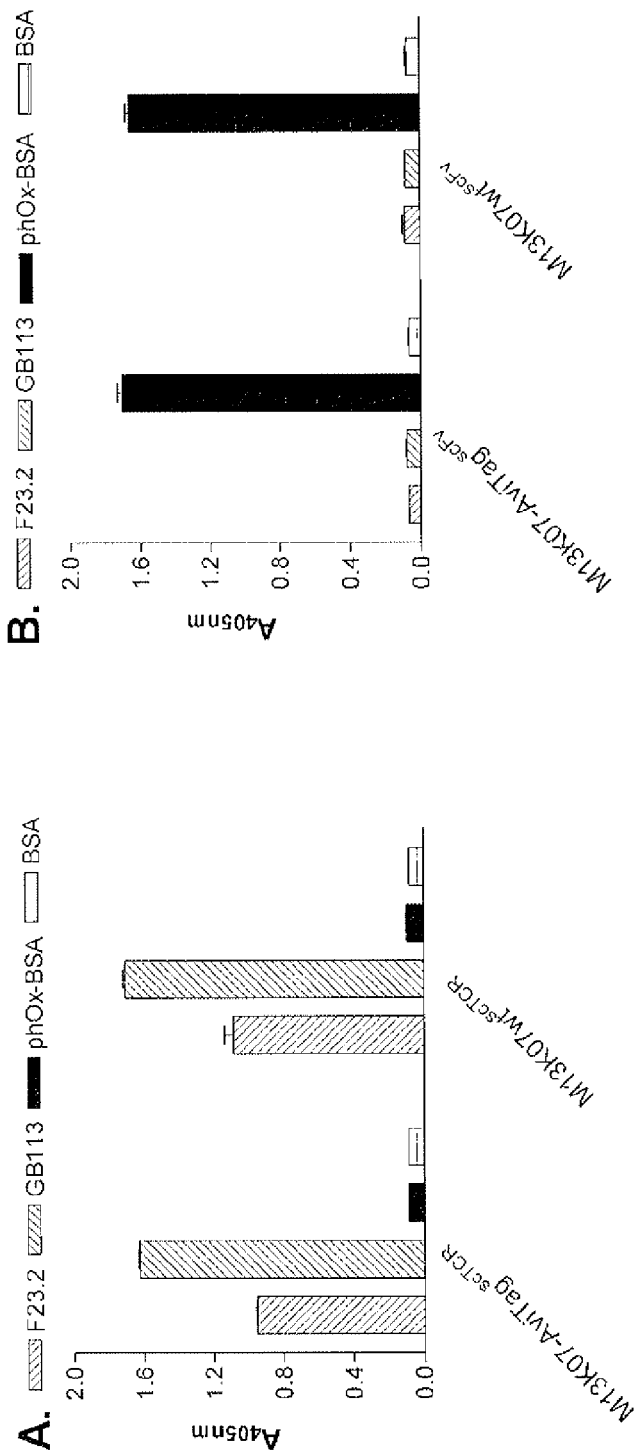
Figure 11:
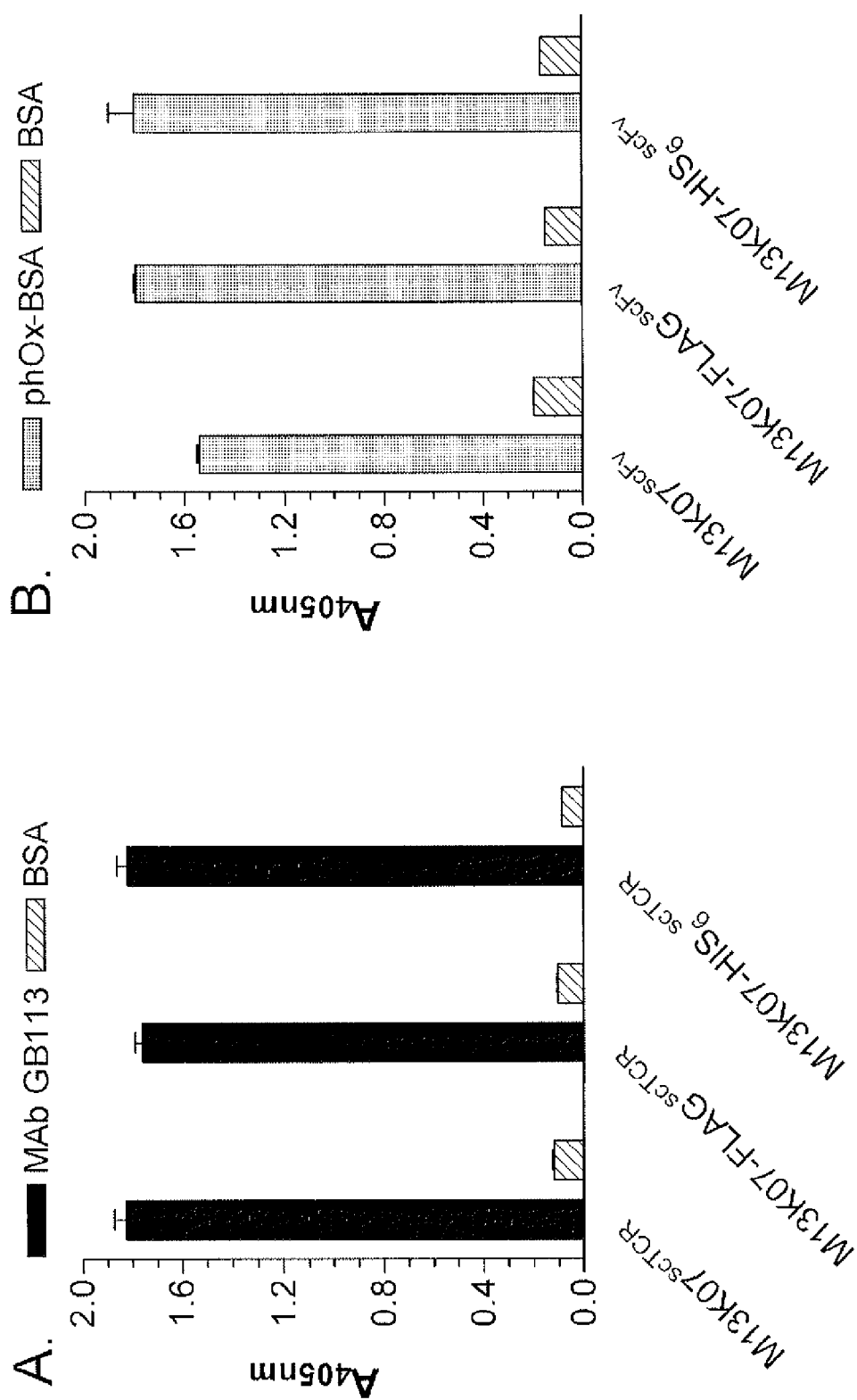

ELISA assays were performed by capturing of phagemid virions by their specific targets, MAB GB113 which binds scTCR and phOx-BSA for the scFv anti-phOx (SEQ ID NO:26). BSA was used as block and phagemids rescued by wt M13K07 was used as a control. Briefly, targets were coated on ELISA plates ON at 4° C. The plates were washed and phagemid preparations were incubated on the plates for 2 hours at room temperature. The plates were washed and further incubated with anti-M13 HRP conjugated antibody. The signals was developed with ABTS and incubation at RT/30 min, followed by measuring the absorbance at A405 nm (FIGS. 10 and 11).

The results show that cognate Ag-reactivity is obtained for all packaged phagemids. This analysis thus confirms that the modified helper phages do not affect the pIII display, but merely donates a defined phenotype to the pVII protein on the very same virion.

Example 3

Genomic Phage Display on pIII and pVII

The invention allows for the generation of a genomic phage vector with display properties on pVII coatproteins. Such display will not affect the infectivity of virions like pIII display. Furthermore, the invention fosters bispecific display on pVII and pIII/pVIII, or even all three coat proteins simultaneously. The following example supports bispecific display on pIII and pVII in a genomic phage display system showing that the construct behave completely like wildtype phages with respect to propagation, virion assembly, viron concentration, pIII display phenotype and that it indeed is selectively in vivo biotinylated at the pVII peptide fusion.

Reagents

All media and buffers were prepared essentially as described in Sambrook et al (Molecular cloning: a laboratory manual (Cold Spring Harbor Laboratory Press)). The anti-M13-HRP antibody was purchased from GE Healthcare Bio-Sciences AB (Uppsala, Sweden) and the F23.2 and GB113 antibodies were a kind gift from Professor B. Bogen (Institute of Immunology, University of Oslo, Norway). Restriction enzymes (RE) were purchased from New England Biolabs (Ipswich, Mass., USA) with the exception of DpnI, which was obtained from Stratagene (LaJolla, Calif., USA). DNA oligos were purchased from MWG Biotech AG (Ebersberg, Germany). Dynabeads MyOne™-Streptavidin magnetic beads were purchased from Invitrogen (Oslo, Norway). dm$^5$CTP was from Fermentas (Burlington, Canada) BSA and Tween 20 was purchased form Sigma-Aldrich (Oslo, Norway). Pfu Turbo DNA and Phusion DNA polymerases were purchased from Stratagene (LaJolla, Calif., USA) and Sigma-Aldrich (Oslo, Norway), respectively. The QIAquick PCR clean-up kit was from Qiagen (Qiagen, Hilden, Germany).

Bacterial Strains, Phage and Phagemids

The *E. coli* strain XL1-Blue was purchased from Stratagene (LaJolla, Calif., USA), whereas the *E. coli* strains MC1061 and K91K were kind gifts form Dr G. P. Smith (Division of Biological Sciences, University of Missouri, USA) The pSEX81 (SEQ ID NO:29) phagemid harbouring a scFv with specificity against 2-phenyloxazol-5-one (phOx) coupled to bovine serum albumin (BSA) were kindly provided by Affitech AS (Oslo, Norway). The fUSE5-scTCR Vαβ4B2A1 pIII display vector is described in (Løset et al 2007, PMID: 17925331).

Design and In Vitro Mutagenesis of AviTag™-pVII

The open reading frame (ORF) of the AviTag™ (N-MS-GLNDIFEAQKIEWHE-C) was compared to the codon usage in *E. coli* K12 strains using the GCUA server (http://gcua.schoedl.de/seqoverall.html). A prokaryotic codon-optimized version of the AviTag™ peptide sequence was attached N-terminally to the pVII ORF by QuikChange™ in vitro mutagenesis according to the manufacturers' protocol (Stratagen, LaJolla, Calif., USA), using the primer pair BirA-pVII_frwd/BirA-pVII_rev (5'-CCGGCTAAGTAACATGTCCG-GCCTGAACGATATCTTTGAAGCGCAGAAAATTGAA-TGGCA TGAAATGGAGCAGGTC-'3/5'-GACCTGCTC-CATTTCATGCCATTCAATTTTCTGCGCT-TCAAAGATATCGTTCAGGCCGGAC ATGTTACT-TAGCCGG-3') (SEQ ID NO:5 and SEQ ID NO:6, respectively). To ensure a clean vector background, a BsrGI/SnaBI RE fragment containing the modified pVII was cloned into an unmodified fUSE5-scTCR Vαβ4B2A1 genome on compatible RE sites using standard techniques. The DNA construct was introduced into *E. coli* MC1061 by electroporation. Primer design was based on the published fUSE5 sequence (GenBank accession no.: AF218364) (SEQ ID NO: 30).

Construction of the Novel Genomic pVII Display Vectors pGVII and pGVIIΔL

Primer design and vector assembly was done essentially as described in the SeamLess protocol (Stratagene, LaJolla, Calif., USA). Using VCSM13 genome DNA (SEQ ID NO: 32) as template and the primer pair VCSM13_F/VCSM13_R (5'-ATCTCTTCCATGGAGCAGGTCGCG-GATTTCGACACAATTTATCAGG-3'/5'-ATCTCTTCCAT-GTTACTTAGCCGGAACGAGGCGCAGAC-3') (SEQ ID NO:19 and SEQ ID NO: 20, respectively), the complete genome was PCR amplified with Pfu Turbo polymerase essentially as described in the SeamLess protocol (Stratagene, LaJolla, Calif., USA). Likewise, pSEX81ΔL (the latter described in Example 4), and pSEX81 (SEQ ID NO:29) both harbouring a scFv anti-phOx (SEQ ID NO:26) unit, were used as template in a standard PCR using Phusion DNA polymerase (Sigma, Oslo, Normay) with the primer pairs pGALDL_F/pGAL_R (5'-TCTCTTCACATGGCCCAGGT-GCAGCTGGTGCAG-3'/5'-ATCTCTTCCCATTCT-GATATCTTTGGATCCAGCGGCCGCAC-3') (SEQ ID NO: 22 and SEQ ID NO: 23, respectively). and pGAL_F/pGAL_R (5'-ATCTCTTCACATGAAATACCTATTGC-CTACGGCAGCCGCTGGC-3'/5'-ATCTCTTCCCATTCT-GATATCTTTGGATCCAGCGGCCGCAC-3')) (SEQ ID NO: 21 and SEQ ID NO: 23, respectively), respectively, to amplify the scFv units. Following PCR, all three segments were purified by a PCR clean up kit (Qiagen, GmBH, Hilden, Germany) and RE digested with EarI. RE digested, gel purified segments were then ligated and electroporated into XL1-Blue using standard techniques. Colonies were expanded and verified for correct insert size by PCR screening in a standard PCR using the primer pair pVII_frwd/pVII_rev (5'-AGCAGCTTTGTTACGTTGATTTGG-3'/5'-GCAGCGAAA-GACAGCATCG-3')) (SEQ ID NO: 24 and SEQ ID NO: 25, respectively). The genomic pVII display vectors were denoted pGVII (having signal sequence-dependent scFv-pVII display) and pGVIIΔL (having scFv-pVII display without any signal sequence). These now contain the scFv ORF as an in-frame fusion N-terminal to pVII and preserving the correct positioning of its start codon to the upstream pV ORF important for normal transcription and translation. Notably, the assembly of these phage genome vectors can just as easily be made by a three step PCR assembly where the exogenous ORF is PCR amplified with 5'-primer tag overhangs complementary to the vector backbone, which can be spliced by PCR SOEing with complementary segments amplified from the 5'- and 3'-portion of the vector covering the site of insertion. An ideal portion of the phage genome should cover a segment including the two unique RE sites BsrGI/SnaBI that are found flanking the pVII ORF in all Ff genomes. RE digested SOEing product can then conveniently be inserted into a complementary RE digested vector backbone, as describe e.g in Example 1 and 3. Another convenient assembly avenue would be to make an artificial gene assembly of the appropriate fusion ORF completely by short overlapping oligonucleotides that may be annealed as one pot, ligated and PCR amplified by flanking primers. This strategy could render an identical fragment as in the SOEing approach, or be RE independent on which insertion into the phage genome could be based e.g. on recombination as described (Tillett and Neilan, PMID: 10481038). A blend of the techniques may also easily be envisioned.

Preparation of Phage Particles fUSE5 phages were amplified from E. coli MC1061 essentially as described (Scott and Smith, PMID: 1696028). Virion assembly was monitored by spot titration as described (Scott and Smith, PMID: 1696028 and Koch et al, PMID: 11126120). Where applicable, virions were purified and concentrated by PEG/NaCl precipitation as described (Sambrook et al (Molecular cloning: a laboratory manual (Cold Spring Harbor Laboratory Press)).

Phage-Capture Enzyme Linked Immunosorbent Assays (ELISAs)

F23.2, GB113 antibodies were absorbed to MaxiSorp™ microtiter plate wells (Nunc, Roskilde, Denmark) in concentrations from 2.5 to 5 µg/ml in PBS, pH 7.4 overnight at 4° C. The wells were blocked with 2% skim milk in PBS (w/v) for 1 h at RT, virion preparations where then added and allowed to react for 1 to 2 h at RT before captured virions were detected with anti-M13-HRP (1:5,000) for 1 h at RT. Between each step, the wells were washed 3× with PBST. The wells were developed with ABTS substrate and the absorbance read at $A_{405nm}$ after 30 min.

A—Titration of fUSE5-scTCR-Avitag Genomic Phages

Figure 12:
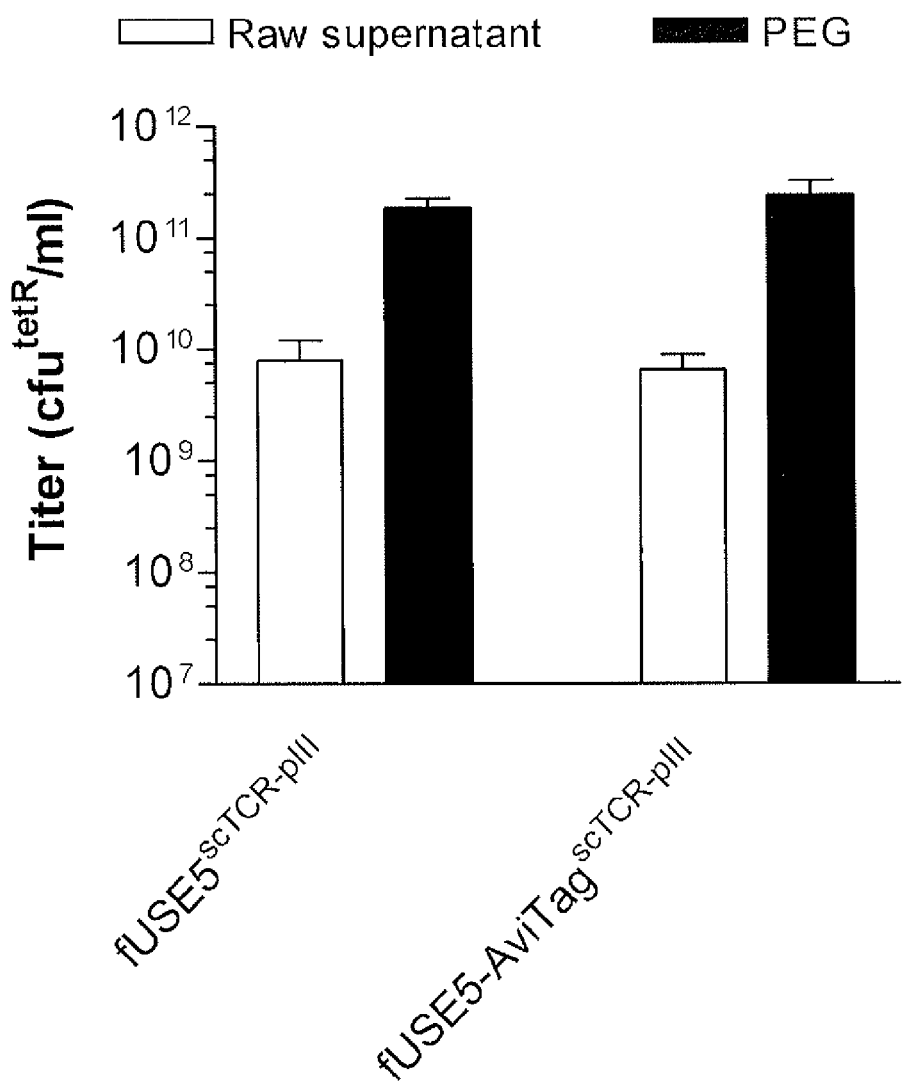

Neither the wt, nor the pVII-modified fUSE5-scTCR Vαβ4B2A1 versions exhibit any host toxicity. There is no phenotypic difference between the pVII-modified fUSE5-scTCR Vαβ4B2A1 versions regarding virion production and PEG precipitation efficiency. Both the pVII-modified fUSE5-scTCR Vαβ4B2A1 versions yield close to maximum theoretical titers feasible with the fUSE5 system (FIG. 12).

B—Functionality of fUSE5-VII-AviTag Fusion Peptide

Figure 13:
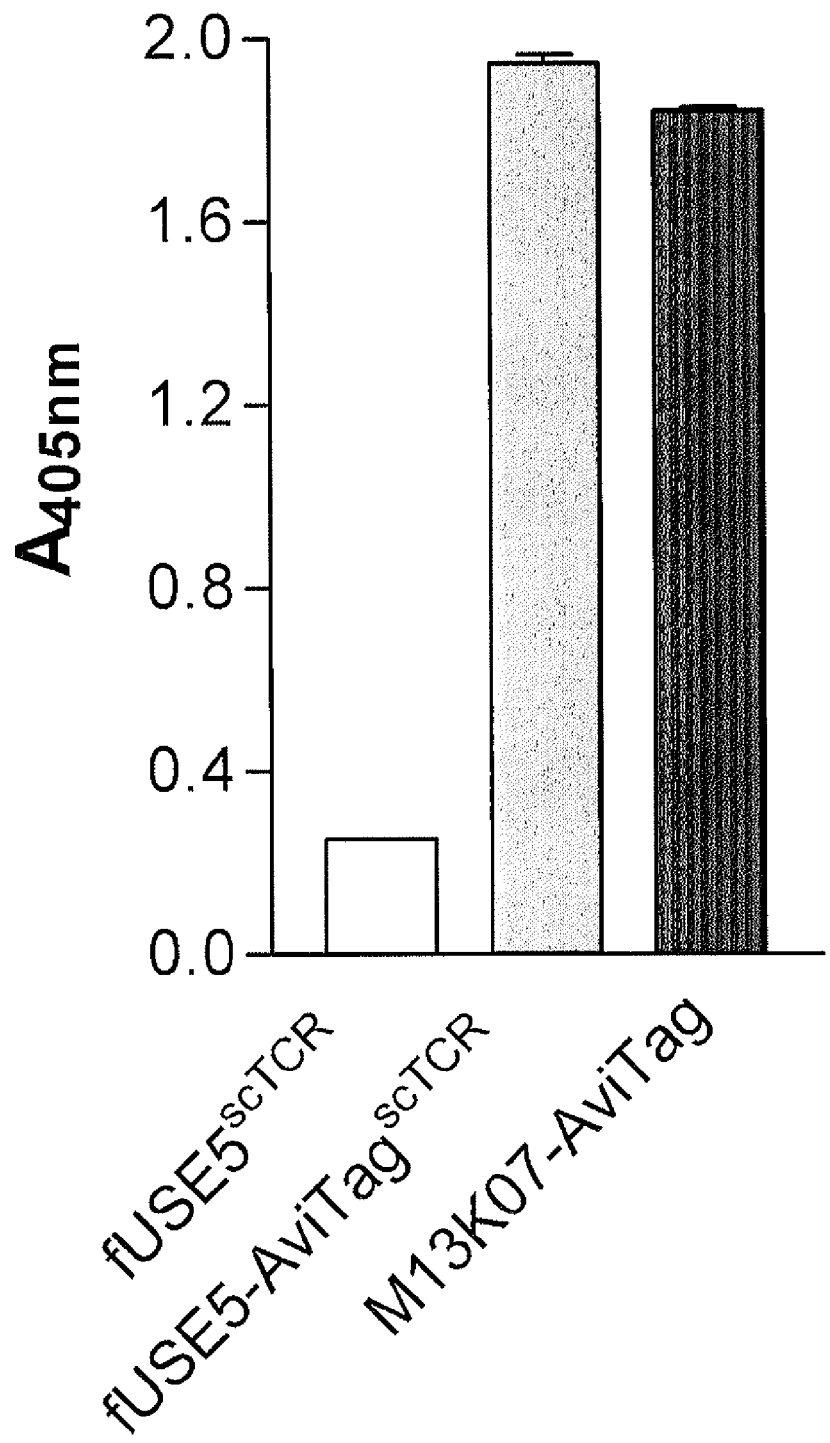

This ELISA analysis is to test the functionality of genomic phage preparations by capturing virions by streptavidin beads followed by detection of bound phages by anti M13-Antibodies. Briefly, MyOne Streptavidin dynabeads were blocked with BSA, washed and incubated with titer-normalised samples of fUSE5 phages with (scTCR/pVII-AviTag) and without (scTCR/pVII) pVII-Avitag fusion peptides. Beads were washed and bound phages were detected with ani-M13-HRP conjugated antibodies. Signal was developed by addition of ABTS and measured at A405 nm using a TECAN ELISA reader apparatus. The results show that the pVII-BirA peptide is accessible and has been biotinylated, and thus serves as an immobilisation and detection tag for phage genome-derived virions (FIG. 13).

C—Functionality of fUSE5-scTCR pIII-Fusion

Figure 14:
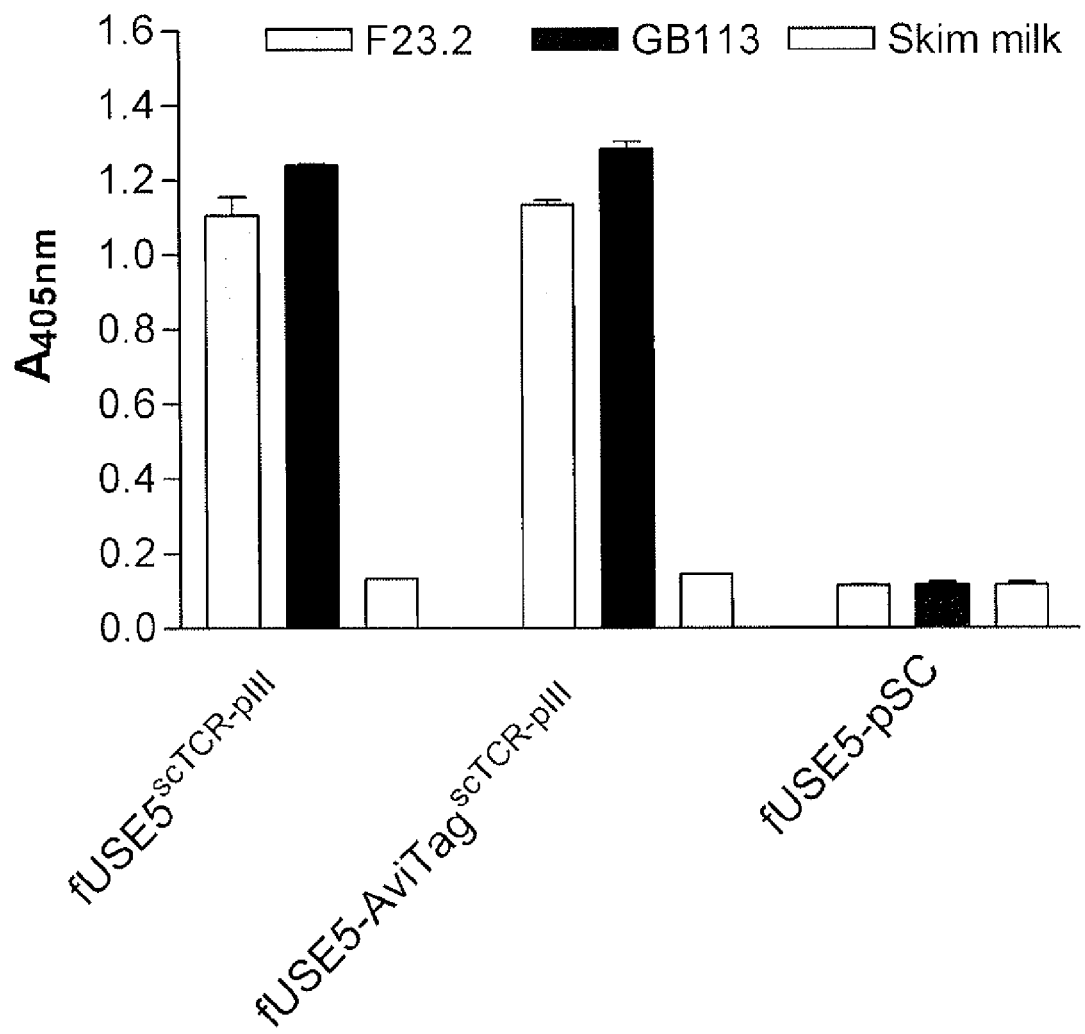

This ELISA analysis is to test the pIII fusion functionality of phage genome-derived virion preparations with and without genome-encoded AviTag-pVII. ELISA assays were performed by capturing of phage virions by two different antibodies recognising the scTCR Vαβ4B2A1) (SEQ ID NO: 28); MAB GB113 and F23.2, respectively. Skimmed milk was used as negative control. Briefly, antibodies were coated on ELISA plates ON at 4° C. The plates were washed and phage titer normalised preparations were incubated on the plates for 2 hours at room temperature. The plates were washed and further incubated with anti-M13 HRP conjugated antibody followed by the addition of 100 µl ABTS and incubation at RT. The absorbance was measured after 20 min at OD405 nm using a TECAN ELISA reader apparatus. The result shows that the scTCR phenotype is indistinguishable between the two fUSE5 versions. Hence, the pVII modification does not appear to affect the phenotype of the phage in any respect (FIG. 14).

Example 4

Phagemid Display on pVII

Reagents

All media and buffers were prepared essentially as described in Sambrook et al (Molecular cloning: a laboratory manual (Cold Spring Harbor Laboratory Press)). The anti-M13-HRP antibody was purchased from GE Healthcare Bio-Sciences AB (Uppsala, Sweden) and the GB113 antibody was a kind gift from Professor B. Bogen (Institute of Immunology, University of Oslo, Norway). Restriction enzymes (RE) were purchased from New England Biolabs (Ipswich, Mass., USA) with the exception of DpnI, which was obtained from Stratagene (LaJolla, Calif., USA). DNA oligos were purchased from MWG Biotech AG (Ebersberg, Germany). BSA and Tween 20 was purchased form Sigma-Aldrich (Oslo, Norway). Pfu Turbo DNA polymerase was purchased from Stratagene (LaJolla, Calif., USA). The haptens 2-phenyloxazol-5-one phOx and 5-nitrophenacetyl (NIP) conjugated to BSA were prepared essentially as described elsewhere (Makela et al, PMID; 722243 and Michaelsen et al, PMID: 2125362). Isopropyl-beta-D-thiogalactopyranoside (IPTG) was purchased from Fermentas (Burlington, Canada).

Bacterial Strains, Phage and Phagemids

The E. coli strain XL1-Blue was purchased from Stratagene (LaJolla, Calif., USA). M13K07 helper phage was purchased from GE Healthcare Bio-Sciences AB (Uppsala, Sweden). The pSEX81 (SEQ ID NO:29) phagemid harbouring a scFv with specificity against 2-phenyloxazol-5-one (phOx) coupled to bovine serum albumin (BSA) was kindly provided by Affitech AS (Oslo, Norway). The pFKPDNscTCR Vαβ4B2A1 pIII display phagemid has been described elsewhere (Løset et al 2007, PMID: 17925331). The prokaryotic expression vector pSG1 harbouring the scFv anti-NIP (SEQ ID NO: 27) (unpublished) is based on pHOG21 (Kipriyanov et al, PMID: 9005945) and has been made in-house from the antibody variable genes derived from pLNOH2 and pLNOK (Norderhaug et al, PMID: 9202712).

Construction of the novel pVII display phagemid vectors pGALD7 and pGALD7ΔL As a starting template for the vector backbone, the pSEX81 (SEQ ID NO:29) phagemid described above was chosen (GenBank accession no.: Y14584). Firstly, to remove the prokaryotic pelB signal sequence (N-MKYLLPTAAAGLLLLAAQPAMA-C) (SEQ ID NO:33) encoding strech in this vector, a NcoI RE site was introduced in the extreme N-terminus by QuikChange™ in vitro mutagenesis using the primer pair a41g-frwd/a41g-rev (5'-AGAGGAGAAATTAACCATGGAATAC-CTATTGCCTACGGC-3'/5'-GCCGTAGGCAATAGGTAT-TCCATGGTTAATTTCTCCTCT-3') (SEQ ID NO:13 and SEQ ID NO: 14, respectively), thereby changing the first nucleotide in the second codon of the pelB ORF from A to G. Following mutagenesis, the vector was NcoI digested, re-ligated and used as template in a second PCR retrieving the relevant part of the vector using the primer pair pHOG_EcoRI_frwd/scTCR_rev (5'-TAGCTCACTCATT-AGGCACCC-3'/5'-TTTGGATCCAGCGGCCGC-3') (SEQ ID NO:15 and SEQ ID NO: 16, respectively). This PCR fragment was then moved into the original pSEX81 (SEQ ID NO:29) on the compatible EcoRI/HindIII RE sites using standard techniques and confirmed by DNA sequencing. This step completely removed the pelB signal sequence encoding portion, but preserved the start codon and its relative position towards the lacPO and Shine-Dalgarno sequence (SD) important for normal transcription and translation, as well as adding only one Ala residue before the exogenous sequence defined by the NcoI/NotI RE sites found in the original pSEX81 (SEQ ID NO:29). The new construct was denoted pSEX81ΔL. Secondly, the pVII encoding sequence was amplified from M13K07 using the 5'-end RE-tagged primer pair pVII_EcoRV/pVII_NheI (5'-ATATGATATCAGAATGGAG-CAGGTCGCGGATTTCG-3'/5'-ATATGCTAGCTTAT-CATCTTTGACCCCCAGCGATTATACC-3') (SEQ ID NO:17 and SEQ ID NO: 18, respectively). This PCR fragment was then moved into both the pSEX81 (SEQ ID NO:29), and pSEX81ΔL phagemids on the compatible RE sites, thereby exchanging the pIII encoding region in both and resulting in a N-terminal in-frame pVII fusion of the NcoI/NotI-defined cassette in the original pSEX81 (SEQ ID NO:29). The new constructs were confirmed by DNA sequencing and denoted pGALD7 and pGALD7ΔL, respectively. To switch the scFv anti-phOx (SEQ ID NO:26) unit in the various phagemids described above, with the scTCR Vαβ4B2A1 and scFv anti-NIP (SEQ ID NO: 27) units from pFKPDN and pSG1, respectively, this was done as NcoI/NotI RE defined cassette exchange using standard techniques. All phagemids described herein were introduced into E. coli XL1-Blue by electroporation using standard techniques.

Preparation of Phage Particles

Phagemid rescue from E. coli XL1-Blue using M13K07 helper phages and virion assembly was monitored by spot titration as described (Welschof et al, PMID: 9050877 and Koch et al, PMID: 11126120).

Phage-Capture Enzyme Linked Immunosorbent Assays (ELISAs)

MAb GB113, phOx-BSA or NIP-BSA were absorbed to MaxiSorp™ microtiter plate wells (Nunc, Roskilde, Denmark) in concentrations from 2.5 to 5 µg/ml in PBS, pH 7.4 overnight at 4° C. The wells were blocked with 2% skim milk, or 2% BSA in PBS (w/v) for 1 h at RT, virion preparations where then added and allowed to react for 1 to 2 h at RT before captured virions were detected with anti-M13-HRP (1:5,000) for 1 h at RT. Between each step, the wells were washed 3× with PBST. The wells were developed with ABTS substrate and the absorbance read at $A_{405nm}$ after 30 min.

Results

Figure 15:
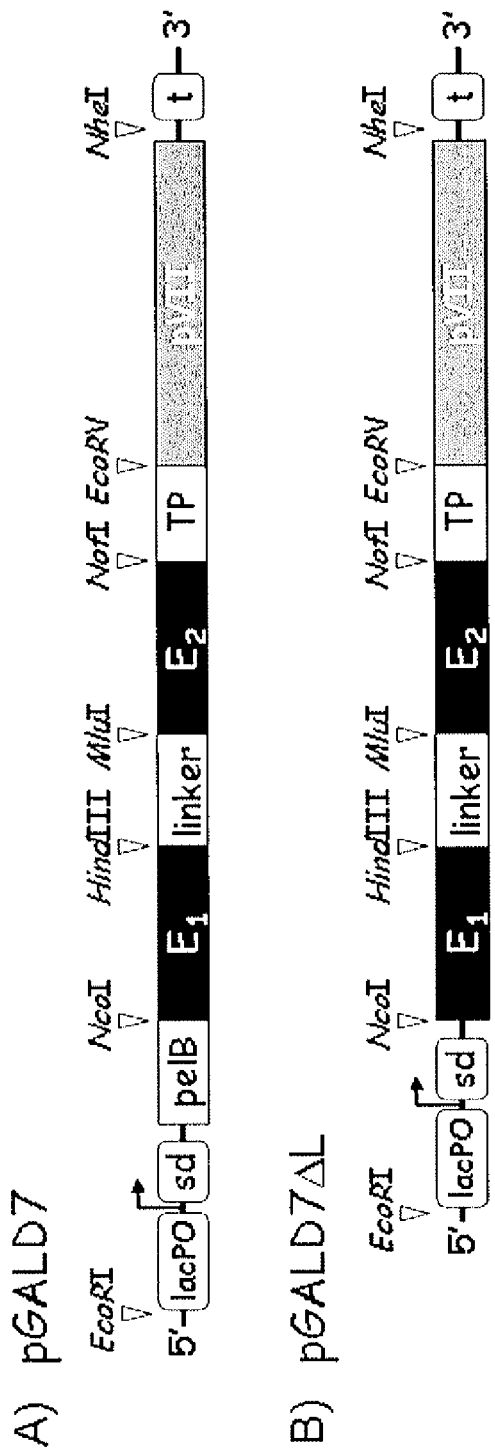

Prompted by the results from the modified helper phages described above, pVII display of folded domains was also assessed. As both Gao et al and Kwasnikowski et al have shown that such display is allowed when used in combination with signal sequence-directed periplasmic targeting, we constructed two novel phagemids termed pGALD7 and pGALD7ΔL, allowing for N-terminal pVII display with and without such a signal sequence, respectively (FIG. 15).

Figure 16:
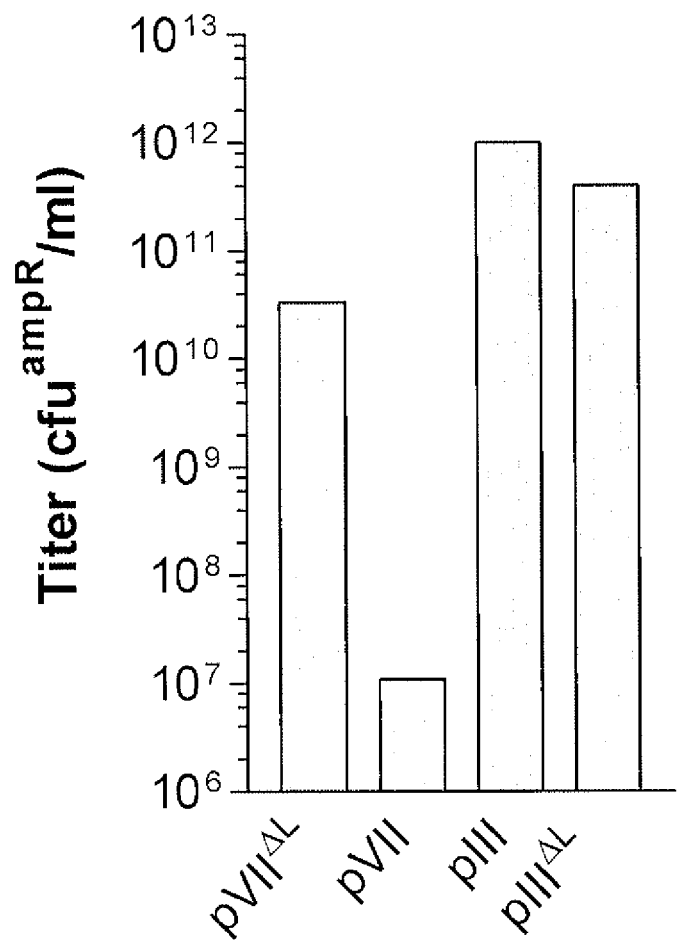

The initial constructs contained a scFv unit based on human antibody variable segments and being specific for the hapten conjugate phOx-BSA. As with the pVII modified helper phages described previously, pVII display of the scFv should not interefere with normal virion assembly. We therefore compared the performance of these scFv anti-phOx pVII display phagemids with and without signal sequence and also with standard pIII display with and without signal sequence, using standard phagemid rescue and titration as described in materials and methods. (FIG. 16)

The titration result indeed showed that phagemid-containing virions were made in all cases. However, whereas the pVIIΔL phagemid yielded titers about 30-fold lower than standard pIII display, there was a gross $10^5$-fold reduction in the signal sequence-directed pVII display. As wt complementation of pVII is present from the helper phage in this system, this finding was both surprising and important, because it shows that the signal sequence-directed pVII display (pVII) severely interferes with the virion assembly process, whereas this effect is only minor in the case with signal sequence-less pVII display (pVII$^{ΔL}$). In comparison, the titer difference between pIII display with and without signal sequence, was only minor.

Figure 17:
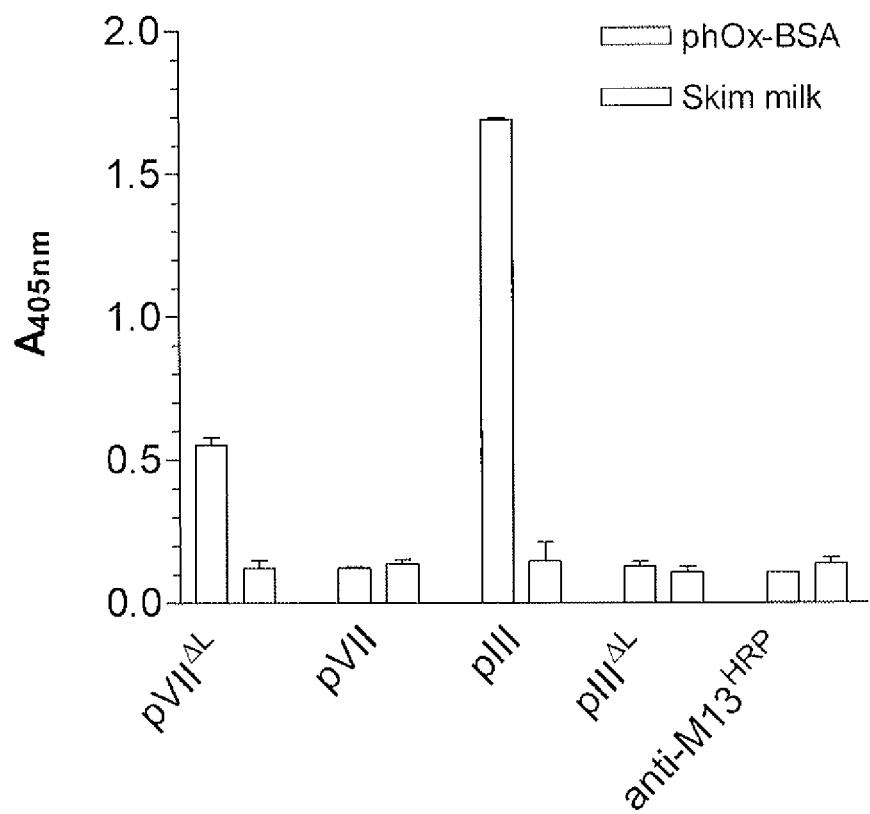

Based upon the titers determined above, we then assessed the functional scFv display on these virion samples in a phOx-BSA specific ELISA using titer normalized inputs, except for the pGALD7-derived sample that was used undiluted as the phagemid titer was very low. (FIG. 17).

The result clearly showed functional scFv display from both the signal sequence-less pVII version and standard pIII, whereas the other samples were negative. That the signal sequence-directed pVII display yielded negative results was expected due to the 2000-fold less virion input. It is known that pIII is exported to the periplasm through the SEC-pathway, hence the signal sequence-less pIII version yields pIII fusions defect in perplasmic targeting, which is a prerequisite for virion incorporation. The virions from this sample, hence contains only helper phage derived pIII (loss of physical phenotype-genotype linkage), though the phagemid packaging efficiency is close to normal and results in normal titers (as seen in FIG. 16 Though both signal sequence-less pVII version and standard pIII display yielded functional display, it is clear that the antigen binding ability appears stronger with pIII. This does not necessarily reflect a higher functionality of the pIII version, as it is well documented that standard pIII display renders a mixture of mono- to oligovalent display of scFv units causing avidity effects (Bradbury and Marks, PMID: 15261570). Such effects are masking the true inherent affinity of the interaction, and though the scFv unit is often preferred due to superior expression profile, it is extensively documented that e.g. the lower expressed Fab format, in the meaning of less units per virion, results in much stronger binders upon affinity selection (de Haard, et al, PMID: 10373423 and Hoogenboom, PMID: 16151404). It could therefore be that the lower signal from the pGALD7ΔL rather reflects a closer to monovalent scFv display, which for many applications could be advantageous.

The scFv-pVII/pIII expression cassette in all the phagemids employed here are controlled by the lac promoter and the virion packaging was done using the standard protocol without IPTG induction (Welschof et al, PMID: 9050877), Thus, it should be possible to increase the scFv display by forcing stronger expression using IPTG during packaging. Moreover, an important feature of phagemid phage display is the fact that functional display is dependent upon helper phage mediated rescue of the phagemid. Therefore, in contrast to phage genome-based display, there are two sources of ssDNA that can be packaged into the virion from a given cell—the phagemid, or the helper phage genome. Importantly, both types of virions will have access to the very same pool of capsid proteins, as they are produced and found within the very same host cell. To ensure the preservation of the physical genotype-phenotype linkage that forms the very basis for combinatorial phage display technology, it is therefore of the out most importance that the phagemid-to-helper phage ratio is in favour of the phagemid. In a new experiment, we prepared the same phagemid-derived samples as described above, but now also comparing virion assembly with and with out IPTG included during packaging. During titration, we this time also mapped the helper phage genome titers by means of the kanamycin resistance found on the helper phage genome.

The current titration result (FIG. 18A) exhibited the very same trend as in the former packaging (FIG. 16), with respect to phagemid titers when comparing the different phagemids at standard conditions, but this time both the pGALD7ΔL (pVII$^{ΔL}$) and the pGALD7 (pVII) had somewhat higher titers. Upon IPTG induction of the pVII, or pIII expression all phagemids exhibit a reduction in titer, but the effect is the most severe for the sequence signal-directed pVII pGALD7 phagemid. When mapping the phagemid-to-helper phage ratios (FIG. 18B) and comparing the different phagemids under standard conditions (without IPTG present), all samples exhibit ratios in the normal range and in favour of the phagemid, except for the sequence signal-directed pVII pGALD7 phagemid, which exhibits a complete loss of the phenotype-genotype linkage. Upon IPTG induction, the uncoupling of the phenotype-genotype was even more pronounced for the pGALD7 phagemid, and now also the signal sequence-less pIII (pIII$^{ΔL}$) exhibited this feature to a small extent (ratio 0.5). However, the latter construct is nevertheless non-functional with respect to pIII display and was only included as control.

Based upon the phagemid titers shown in FIG. 18A, we then assessed the functional scFv display of the pGALD7ΔL and pGALD7 virions in a phOx-BSA specific ELISA similar to that shown in FIG. 17. Using normalized titer inputs.

The result did indeed show the functional scFv-pVII display was again achieved with the signal sequence-less pGALD7ΔL and the phOx-BSA reactivity increased significantly upon IPTG-forced pVII fusion expression. This increase in antigen reactivity most likely reflects an increased number of pVII fusion per virion as well as an increased number of virions harbouring a pVII fusion per see. The latter is likely as it is known that in standard pIII display only between 1 to 10% of the phagemid-containing virions actually contains a fusion (Bradbury and Marks, PMID: 15261570). On the other hand, the signal sequence-directed pVII display again showed no functional phOx-BSA binding. Based on FIG. 18B, the weak antigen reactivity observed in the IPTG uninduced sample, must be assigned to helper phage containing virions harbouring the pVII fusion at low level.

So far, we have clearly shown functional pVII phagemid-based display of the scFv anti-phOx (SEQ ID NO:26), unit and that this construct is comparable to pIII display of the same scFv, exhibiting only a minor reduction in phagemid titers and in antigen binding capacity.

The scFv anti-phOx (SEQ ID NO:26) has been selected for a human antibody scFv library and is known to express rather well in E. coli (Marks et al., PMID: 1748994). To see whether or not pVII display exhibits the capacity to functional display of more challenging fusion partners, we therefore subcloned a scFv anti-NIP (SEQ ID NO: 27) based on the antibody variable genes of a murine hybridoma, as well as a scTCR based on the variable genes from the murine T cell clone 4B2A1 (Løset et al, PMID: 17925331) into both pGALD7ΔL and pGALD7. It is well known that many hybridoma variable genes do not express well in E. coli and also when phage displayed (Krebber et al, PMID: 9032408) and T cell receptors are on class of folded proteins that has proven especially difficult to accommodate to phage display (Li et al, PMID: 15723046, and Løset et al, PMID: 17925331).

Figure 20:
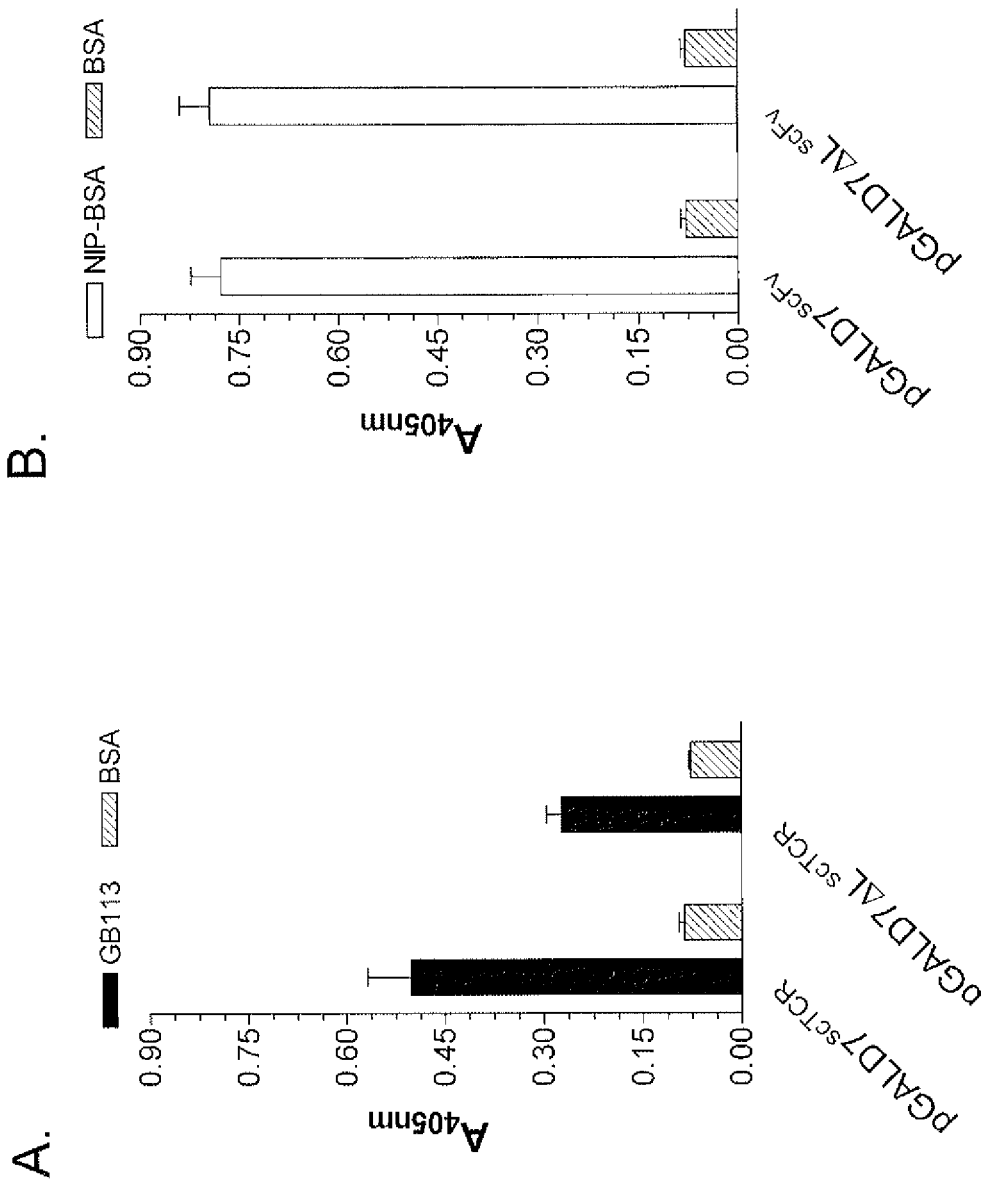

Virions from these new phagemids were prepared by standard phagemid rescue and tested for their antigen binding capacity in ELISA (FIG. 20).

Figure 21:
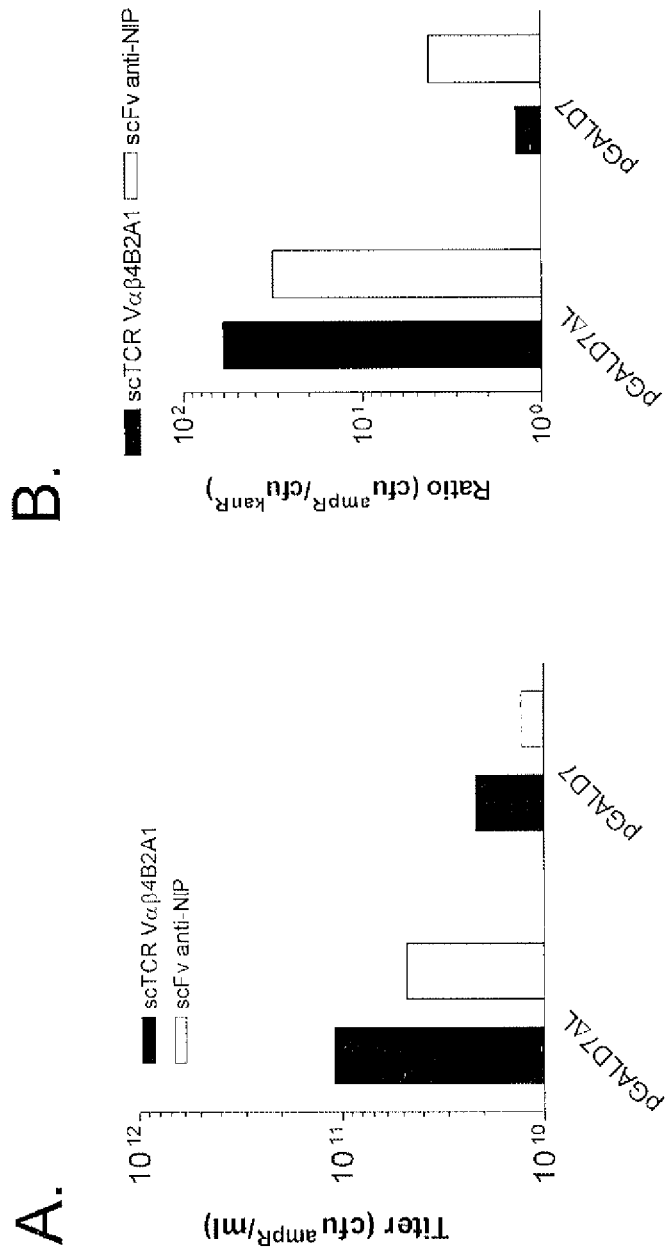

The result did indeed show that functional pVII display was achieved both with the scFv anti-NIP (SEQ ID NO: 27) and the scTCR Vαβ4B2A1 and in contrast to the what was observed previously with the scFv anti-phOx (SEQ ID NO:26), this was the case both with and without signal sequence-directed pVII display. The signals observed in FIG. 20 are not directly compared though as virion titers were not normalized before the assay. In light of the complete non-functional nature of the signal sequence-directed pVII display of the scFv anti-phOx (SEQ ID NO:26), the samples above were titrated and the phagemid-to-helper phage ratios determined (FIG. 21).

Figure 18:
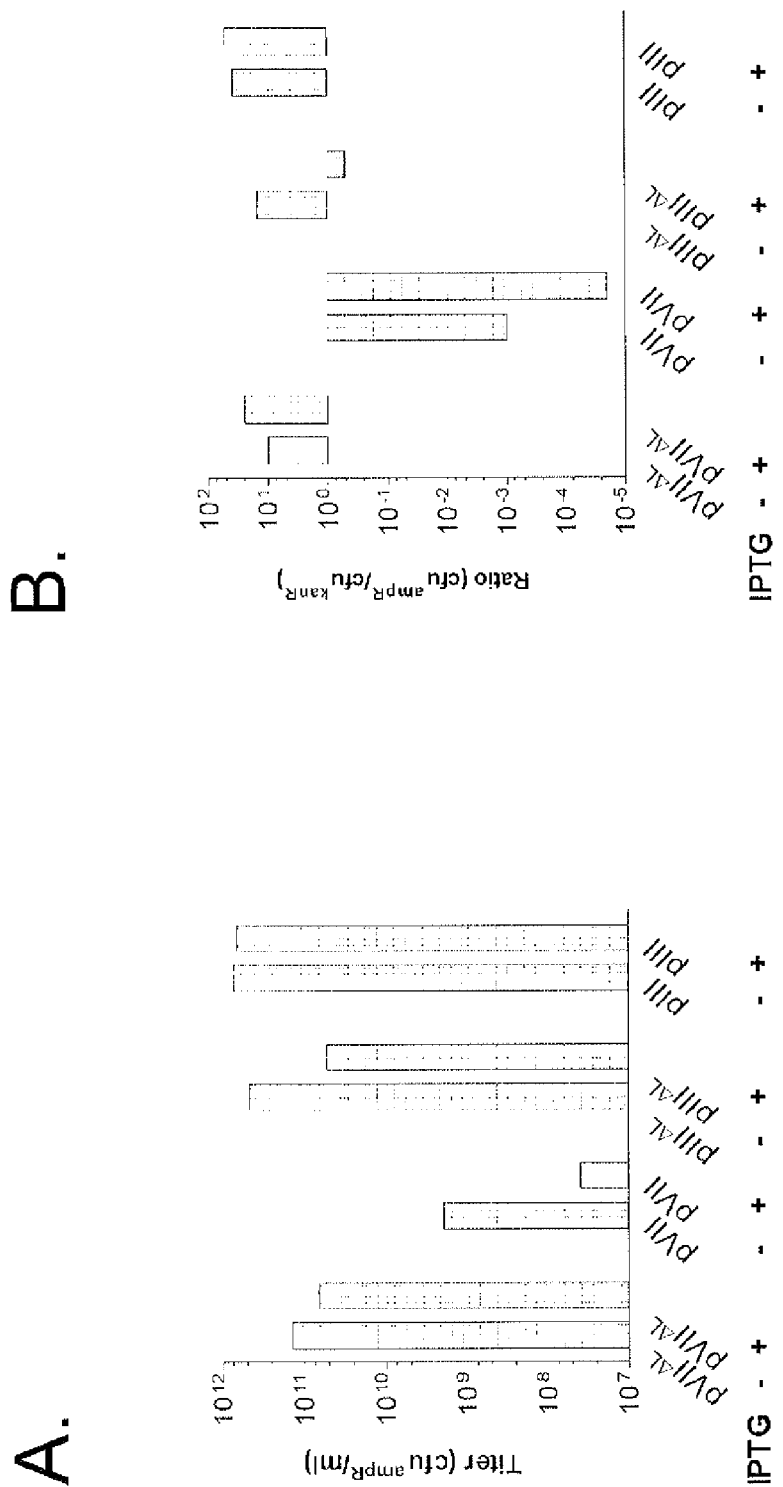
Figure 19:
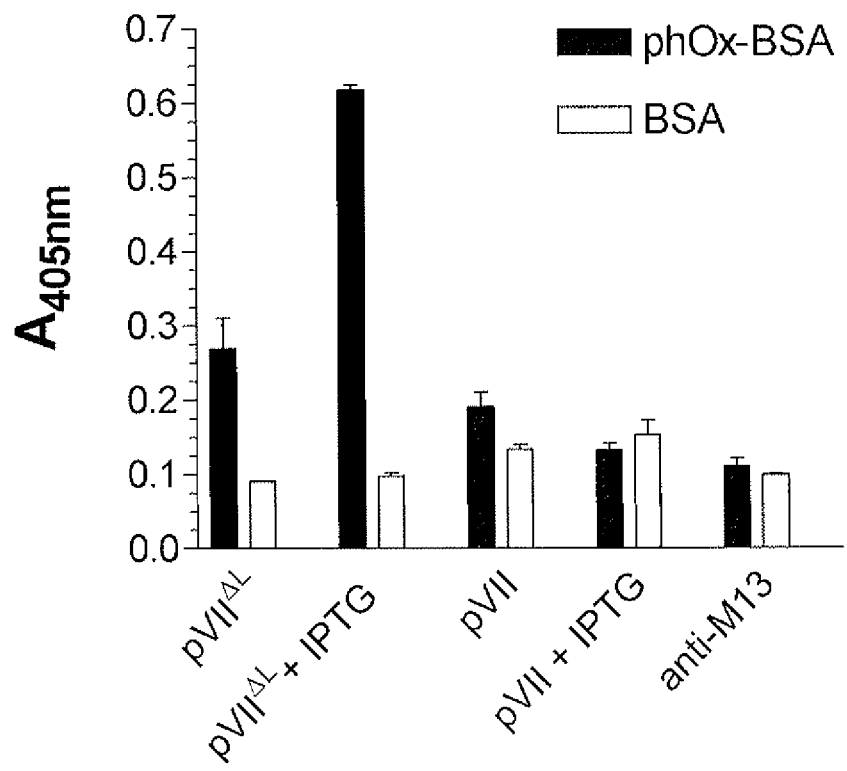

The phagemid titers again showed that the signal sequence-less pVII display (pGALD7ΔL) exhibited superior performance as compared with signal sequence-directed pVII display (FIG. 21A). This was indeed true for both the scTCR and the scFv anti-NIP, but the difference was less obvious than with the titers observed for the scFv anti-phOx (see FIGS. 6 and 8). When comparing the phagemid-to-helper phage ratios, the pGALD7ΔL again showed excellent performance with ratios in strong favior of the phagemid both in the case of the scTCR and the scFv anti-NIP (SEQ ID NO: 27) (FIG. 21B). The severe loss of the genotype-phenotype linkage seen with the scFv anti-phOx (SEQ ID NO:26) was not observed for the scTCR and the scFv anti-NIP (SEQ ID NO:27), from these ratios (FIG. 18 versus FIG. 21B). However, the pGALD7ΔL was clearly superior.

Figure 22:
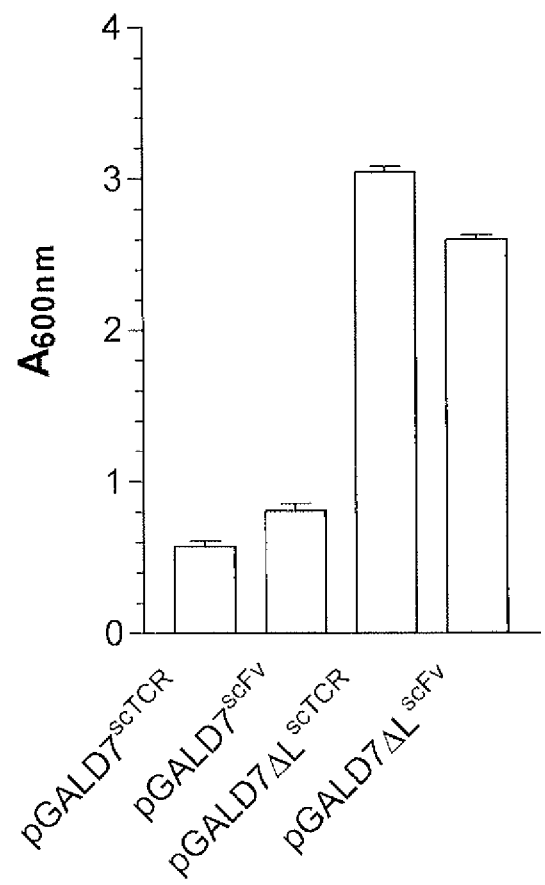

In light of the results above, it was noteworthy the see that there was a quite distinct difference between the scTCR and scFv anti-NIP with respect to host cell proliferation during virion packaging (FIG. 22).

What is evident from FIG. 22 is that whereas the pGALD7ΔL containing cultures only have a minor effect on host cell proliferation, the growth is significantly inhibited by the clones containing the pGALD7 phagemid. This is strongly indicative of host toxicity from the signal sequence-directed pVII display phagemid, whereas no or little such toxicity is observed as soon as the signal sequence is removed.

Example 5

Construction of the E. coli strain AVB100FmkII

Reagents and Bacterial Strain

All media and buffers were prepared essentially as described in Sambrook et al (Molecular cloning: a laboratory manual (Cold Spring Harbor Laboratory Press)). The *E. coli* strains XL1-Blue and AVB100 (based on MC1061) were purchased from Stratagene (LaJolla, Calif., USA) and Avidity (Denver, Colo., USA), respectively.

Results

To obtain F plasmid positive *E. coli* AVB100 (chromosomal $Str^R$) the cells were mated with XL1-Blue (F plasmid $Tet^R$) as follows. Single colonies of each strain was inoculated into 5 ml LB medium supplemented with the appropriate antibiotic and incubated over night at 37° C. with rigorous shaking. The next day, fresh 5 ml cultures were initiated at an $A_{600nm}$ of 0.1 and grown to mid log phase at 37° C. with rigorous shaking before 1 ml of each were mixed and incubated stationary at 37° C. for 1 h. Thereafter, 10 μl of this mixture was transferred to 5 ml fresh LB medium containing 100 μg/ml Str and 30 μg/ml Tet and incubated over night at 37° C. with rigorous shaking. The next day, dilutions of this culture was spread on agar dishes containing 100 μg/ml Str and 30 μg/ml Tet and the resulting colonies used as source of the new F plasmid positive AVB100 strain, termed AVB100FmkII.

REFERENCES

1. Endemann, H. & Model, P. Loccoation of Filamentous Phage Minor Coat Proteins in Phage and in Infected Cells. Journal of Molecular Biology 250, 496-506 (1995).
2. Gao, C. et al. Making artificial antibodies: A format for phage display of combinatorial heterodimeric arrays. PNAS 96, 6025-6030 (1999).
3. Kwanikowski P, Kristensen P, Markiewicz W T. Multivalent display system on filamentous bacteriophage pVII minor coat protein. J Immunol Methods. 2005 Dec. 20; 307(1-2):135-43. Epub 2005 Oct. 28.
4. Khalil A S, Ferrer J M, Brau R R, Kottmann S T, Noren C J, Lang M J, Belcher A M. Single M13 bacteriophage tethering and stretching. Proc Natl Acad Sci USA. 2007 Mar. 20; 104(12):4892-7. Epub 2007 Mar. 13.
5. Baneyx F, Mujacic M. Recombinant protein folding and misfolding in *Escherichia coli*. Nat. Biotechnol. 2004 November; 22(11): 1399-408.
6. Simons G F, Konings R N, Schoenmakers J G. Genes VI, VII, and IX of phage M13 code for minor capsid proteins of the virion. Proc Natl Acad Sci USA. 1981 July; 78(7): 4194-8.
7. Scott J K, Smith G P. Searching for peptide ligands with an epitope library. Science. 1990 Jul. 27; 249(4967):386-90.
8. Koch J, Breitling F, Dübel S. Rapid titration of multiple samples of filamentous bacteriophage (M13) on nitrocellulose filters. Biotechniques. 2000 December; 29(6):1196-8, 2002.
9. Kipriyanov S M, Moldenhauer G, Little M. High level production of soluble single chain antibodies in small-scale *Escherichia coli* cultures. J Immunol Methods. 1997 Jan. 15; 200(1-2):69-77.
10. Welschof M, Terness P, Kipriyanov S M, Stanescu D, Breitling F, Dörsam H, Dübel S, Little M, Opelz G. The antigen-binding domain of a human IgG-anti-F(ab')2 autoantibody. Proc Natl Acad Sci USA. 1997 Mar. 4; 94(5): 1902-7.
11. Michaelsen T E, Aase A, Westby C, Sandlie I. Enhancement of complement activation and cytolysis of human IgG3 by deletion of hinge exons. Scand J Immunol. 1990 November; 32(5):517-28.
12. Näkelä O, Kaartinen M, Pelkonen J L, Karjalainen K. Inheritance of antibody specificity V. Anti-2-phenyloxazolone in the mouse. J Exp Med. 1978 Dec. 1; 148(6): 1644-60.
13. Løset G A, Lunde E, Bogen B, Brekke O H, Sandlie I. Functional phage display of two murine alpha/beta T-cell receptors is strongly dependent on fusion format, mode and periplasmic folding assistance. Protein Eng Des Sel. 2007 September; 20(9):461-72. Epub 2007 Oct. 9.
14. Norderhaug L, Olafsen T, Michaelsen T E, Sandlie I. Versatile vectors for transient and stable expression of recombinant antibody molecules in mammalian cells. J Immunol Methods. 1997 May 12; 204(1):77-87.
15. Bradbury A R, Marks J D. Antibodies from phage antibody libraries. J Immunol Methods. 2004 July; 290(1-2): 29-49.
16. de Haard H J, van Neer N, Reurs A, Hufton S E, Roovers R C, Henderikx P, de Bruïne A P, Arends J W, Hoogenboom H R. A large non-immunized human Fab fragment phage library that permits rapid isolation and kinetic analysis of high affinity antibodies. A large non-immunized human Fab fragment phage library that permits rapid isolation and kinetic analysis of high affinity antibodies.
17. Hoogenboom H R. Selecting and screening recombinant antibody libraries. Nat. Biotechnol. 2005 September; 23(9):1105-16.
18. Marks J D, Hoogenboom H R, Bonnert T P, McCafferty J, Griffiths A D, Winter G. By-passing immunization. Human antibodies from V-gene libraries displayed on phage. J Mol. Biol. 1991 Dec. 5; 222(3):581-97.
19. Altschul S F, Gish W, Miller W, Myers E W, Lipman D J. Basic local alignment search tool. J Mol. Biol. 1990 Oct. 5; 215(3):403-10.

The invention claimed is:

1. A phage genome or a phagemid comprising a nucleic acid encoding a fusion protein comprising the filamentous phage minor coat protein pVII fused to an exogenous peptide, wherein the fusion protein does not comprise an N-terminal signal sequence,
   wherein the filamentous phage minor coat protein pVII comprises a sequence selected from the group consisting of pos. 1-33, 2-33, 3-33, 4-33 and 5-33 of SEQ ID NO:1 (MEQVADFDTIYQAMIQISVVLCFALGIIAGGQR),
   wherein the exogenous peptide of the fusion protein is fused directly to the N-terminal end of the pVII sequence.

2. The phage genome or the phagemid of claim 1, wherein the exogenous peptide of the fusion protein is selected from the group consisting of Avitag (SEQ ID NO:4), FLAG tag (SEQ ID NO:9), HIS tag (SEQ ID NO:12), HAT tag, HA tag, c-Myc tag, Strep tag, V5 tag, antibody fragment, T cell receptor fragment, MHC class I fragment, MHC class II fragment, Ankyrin, IgNAR fragment, fibronectin or fragment thereof, Z domain of protein A, CTLA4 or fragment thereof, ImmE7, GFP and biological gene-encoded fluorophores.

3. The phage genome or the phagemid of claim 1, wherein the exogenous peptide of the fusion protein is a library member.

4. A filamentous phage comprising the phage genome or the phagemid of claim 1.

5. The filamentous phage of claim 4, further comprising a gene encoding wild-type pVII and/or the wild-type pVII protein.

6. The filamentous phage of claim 4, wherein the phage does not comprise a gene encoding wild-type pVII or the wild-type pVII protein.

7. The filamentous phage of claim 4, further comprising a filamentous phage minor coat protein pIII fusion protein or a filamentous phage major coat protein pVIII fusion protein.

8. A library of filamentous phage comprising the filamentous phage of claim 7, wherein the exogenous peptide fused to the filamentous phage minor coat protein pVII is a library member.

9. The filamentous phage library of claim 8, wherein the exogenous peptide fused to the filamentous phage minor coat protein pVII is displayed simultaneously at pVII and either pIII, pVIII, or both.

10. A phage display system comprising a phagemid and a helper phage, wherein the helper phage comprises the nucleic acid of claim 1.

11. A phage display system comprising a phagemid and a helper phage, wherein the phagemid comprises the nucleic acid of claim 1.

12. A kit comprising the phage display system of claim 10.

* * * * *

UNITED STATES PATENT AND TRADEMARK OFFICE
CERTIFICATE OF CORRECTION

Page 1 of 2

PATENT NO. : 8,735,330 B2
APPLICATION NO. : 12/673649
DATED : May 27, 2014
INVENTOR(S) : Geir Åge Løset It is certified that error appears in the above-identified patent and that said Letters Patent is hereby corrected as shown below:

In the Specification,

In column 1 at line 2, Below "Title" insert --CROSS REFERENCE TO RELATED APPLICATIONS This application claims the benefit and priority to and is a U.S. National Phase Application of PCT International Application Number PCT/EP2008/060908, filed on Aug. 20, 2008, designating the United States of America and published in the English language, which is an International Application of and claims the benefit of priority to U.S. Provisional Application No. 60/956,871, filed on Aug. 20, 2007, and Danish Patent Application No. PA 2007 01673, filed on Nov. 26, 2007. The disclosures of the above-referenced applications are hereby expressly incorporated by reference in their entireties.--.

In column 4 at line 50, Change "preaparations" to --preparations--.
In column 5 at line 18, Change "trypsine" to --trypsin--.
In column 5 at line 35, Change "adsorbsion" to --adsorption--.
In column 9 at line 20, Change "periplasmatic" to --periplasmic--.
In column 9 at lines 65-66, Change "g8 pss" to --g8pss--.
In column 12 at line 29, Change "matrixes," to --matrixes.--.
In column 14 at line 44, Change "ligand" to --ligand.--.
In column 16 at line 50, Change "form" to --from--.
In column 16 at line 53, Change "resepectively." to --respectively.--.
In column 16 at line 54, Change "Chalbiochem." to --Calbiochem.--.
In column 18 at line 47, Change "biotinlylation" to --biotinylation--.
In column 19 at line 1, Change "A405nm" to --$A_{405nm}$--.
In column 20 at line 14, Change "kanamycine" to --kanamycin--.
In column 20 at line 19, Change "7)" to --7).--.

Signed and Sealed this
Seventeenth Day of March, 2015

Michelle K. Lee
*Director of the United States Patent and Trademark Office*

CERTIFICATE OF CORRECTION (continued)
U.S. Pat. No. 8,735,330 B2

In column 21 at line 32, Change "A405nm" to --$A_{405nm}$--.

In column 22 at line 58, Change "Normay" to --Norway--.

In column 24 at line 11, Change "A405nm" to --$A_{405nm}$--.

In column 25 at line 14, Change "strech" to --stretch--.

In column 26 at line 19, Change "conjucate" to --conjugate--.

In column 26 at line 21, Change "interefere" to --interfere--.

In column 26 at line 26, Change "16)" to --16).--.

In column 26 at line 52, Change "perplasmic" to --periplasmic--.

In column 27 at line 28, Change "with out" to --without--.

In column 28 at line 49, Change "favior" to --favor--.

In column 29 at line 37, Change "Loccoation" to --Location--.

UNITED STATES PATENT AND TRADEMARK OFFICE
CERTIFICATE OF CORRECTION

PATENT NO. : 8,735,330 B2  
APPLICATION NO. : 12/673649  
DATED : May 27, 2014  
INVENTOR(S) : Geir Åge Løset Page 1 of 1

It is certified that error appears in the above-identified patent and that said Letters Patent is hereby corrected as shown below:

In the specification,

In column 4 at line 35, Change "scTcR" to --scTCR--.

In column 5 at line 53, Change "pVIIΔL" to --pVII$^{\Delta L}$--.

In column 13 at line 25, Change "coatproteins" to --coat proteins--.

In column 14 at line 7, Change "coatproteins" to --coat proteins--.

In column 14 at line 43, Change "coatprotein" to --coat protein--.

In column 20 at line 8, Change "scTcR" to --scTCR--.

In column 21 at line 20, Change "scTcR" to --scTCR--.

In column 21 at line 45, Change "coatproteins" to --coat proteins--.

In column 26 at line 29, Change "pVIIΔL" to --pVII$^{\Delta L}$--.

Signed and Sealed this  
First Day of March, 2016

Michelle K. Lee  
*Director of the United States Patent and Trademark Office*